US010426429B2

(12) United States Patent
Kruse et al.

(10) Patent No.: US 10,426,429 B2
(45) Date of Patent: Oct. 1, 2019

(54) ACOUSTIC ORTHOPEDIC TRACKING SYSTEM AND METHODS

(71) Applicant: Decision Sciences Medical Company, LLC, Poway, CA (US)

(72) Inventors: Dustin Kruse, Grand Island, NY (US); Evan Freiburg, San Diego, CA (US); James J. Hayes, San Diego, CA (US)

(73) Assignee: Decision Sciences Medical Company, LLC, Poway, CA (US)

( * ) Notice: Subject to any disclaimer, the term of this patent is extended or adjusted under 35 U.S.C. 154(b) by 0 days.

(21) Appl. No.: 15/289,013

(22) Filed: Oct. 7, 2016

(65) Prior Publication Data

US 2017/0100092 A1 Apr. 13, 2017

Related U.S. Application Data

(60) Provisional application No. 62/239,169, filed on Oct. 8, 2015.

(51) Int. Cl.
*A61B 8/08* (2006.01)
*A61B 8/00* (2006.01)
(Continued)

(52) U.S. Cl.
CPC ............ *A61B 8/0875* (2013.01); *A61B 8/085* (2013.01); *A61B 8/4227* (2013.01); *A61B 8/4477* (2013.01); *A61B 8/5223* (2013.01); *A61B 34/20* (2016.02); *G01S 7/5202* (2013.01); *G01S 15/899* (2013.01); *G01S 15/8922* (2013.01); *G01S 15/8997* (2013.01); *A61B 8/14* (2013.01); *A61B 8/15* (2013.01); *A61B 8/4263* (2013.01); *A61B 8/4281* (2013.01); *A61B 8/4422* (2013.01);
(Continued)

(58) Field of Classification Search
CPC ... A61B 8/0875; A61B 8/4455; A61B 8/4494; A61B 8/5223; A61B 34/10; A61B 8/4263; A61B 8/085; A61B 8/145
See application file for complete search history.

(56) References Cited

U.S. PATENT DOCUMENTS

| | | | |
|---|---|---|---|
| 4,821,206 | A | 4/1989 | Arora |
| 5,284,143 | A | 2/1994 | Rattner |

(Continued)

FOREIGN PATENT DOCUMENTS

| | | | | |
|---|---|---|---|---|
| CA | 2 427 186 | A1 | 5/2001 | |
| CA | 2852801 | A1 * | 5/2013 | ............. A61B 8/145 |
| CN | 102258399 | B | 11/2012 | |
| EP | 1 707 124 | A2 | 4/2006 | |
| EP | 1 854 406 | B1 | 11/2007 | |
| EP | 1 955 668 | B1 | 8/2008 | |
| EP | 2 033 579 | A1 | 3/2009 | |
| GB | 2472066 | A | 1/2011 | |

(Continued)

OTHER PUBLICATIONS

International Search Report and Written Opinion dated Dec. 29, 2016 for International Application No. PCT/US2016/056159, filed on Oct. 7, 2016 (7 pages).

(Continued)

*Primary Examiner* — Bo Joseph Peng
(74) *Attorney, Agent, or Firm* — Perkins Coie LLP

(57) ABSTRACT

Systems, devices, and methods are disclosed for acquiring and providing information about orthopedic features of a body using acoustic energy. In some aspects, an acoustic orthopedic tracking system includes portable acoustic transducers to obtain orthopedic position information for feeding the information to an orthopedic surgical system for surgical operations.

20 Claims, 28 Drawing Sheets

(51) Int. Cl.
*A61B 34/20* (2016.01)
*G01S 7/52* (2006.01)
*G01S 15/89* (2006.01)
*A61B 34/10* (2016.01)
*A61B 90/00* (2016.01)
*A61B 8/14* (2006.01)
*A61B 8/15* (2006.01)

(52) U.S. Cl.
CPC ........... *A61B 8/4455* (2013.01); *A61B 8/4472* (2013.01); *A61B 8/4494* (2013.01); *A61B 2034/105* (2016.02); *A61B 2034/2048* (2016.02); *A61B 2034/2051* (2016.02); *A61B 2090/378* (2016.02); *G01S 15/8959* (2013.01)

(56) References Cited

U.S. PATENT DOCUMENTS

| | | | |
|---|---|---|---|
| 5,329,944 | A | 7/1994 | Fabian et al. |
| 5,417,218 | A * | 5/1995 | Spivey ..................... A61B 8/13 600/448 |
| 5,445,144 | A | 8/1995 | Wodicka et al. |
| 5,608,690 | A * | 3/1997 | Hossack ............ G01N 29/2456 367/11 |
| 5,800,356 | A | 9/1998 | Criton et al. |
| 5,803,089 | A | 9/1998 | Ferre et al. |
| 5,806,518 | A | 9/1998 | Mittelstadt |
| 5,829,444 | A | 11/1998 | Ferre et al. |
| 5,873,830 | A * | 2/1999 | Hossack ............ G01S 7/52046 600/447 |
| 5,967,980 | A | 10/1999 | Ferre et al. |
| 6,106,464 | A | 8/2000 | Bass et al. |
| 6,110,114 | A * | 8/2000 | Nock ...................... A61B 8/06 128/916 |
| 6,205,411 | B1 | 3/2001 | DiGioia, III et al. |
| 6,322,567 | B1 | 11/2001 | Mittelstadt et al. |
| 6,340,363 | B1 | 1/2002 | Bolger et al. |
| 6,341,231 | B1 | 1/2002 | Ferre et al. |
| 6,402,707 | B1 | 6/2002 | Ernst |
| 6,445,943 | B1 | 9/2002 | Ferre et al. |
| 6,620,101 | B2 | 9/2003 | Azzam et al. |
| 6,626,916 | B1 | 9/2003 | Yeung et al. |
| 6,687,531 | B1 | 2/2004 | Ferre et al. |
| 6,725,082 | B2 | 4/2004 | Sati et al. |
| 6,757,582 | B2 | 6/2004 | Brisson et al. |
| 6,785,571 | B2 | 8/2004 | Glossop |
| 6,796,988 | B2 | 9/2004 | Melkent et al. |
| 6,934,575 | B2 | 8/2005 | Ferre et al. |
| 7,226,456 | B2 | 6/2007 | O'Neil et al. |
| 7,291,119 | B1 | 11/2007 | de Guise et al. |
| 7,395,181 | B2 | 7/2008 | Foxlin |
| 7,473,250 | B2 | 1/2009 | Makin et al. |
| 7,532,201 | B2 | 5/2009 | Quistgaard et al. |
| 7,678,049 | B2 | 3/2010 | Tsoref et al. |
| 7,763,035 | B2 | 7/2010 | Melkent et al. |
| 7,806,823 | B2 | 10/2010 | Sakai et al. |
| 7,826,889 | B2 | 11/2010 | David et al. |
| 7,835,778 | B2 | 11/2010 | Foley et al. |
| 7,835,784 | B2 | 11/2010 | Mire et al. |
| 7,837,625 | B2 | 11/2010 | Abe |
| RE42,194 | E | 3/2011 | Foley et al. |
| 7,938,777 | B2 | 5/2011 | Amiot et al. |
| 7,938,778 | B2 | 5/2011 | Sakai |
| 8,105,339 | B2 | 1/2012 | Melkent et al. |
| 8,126,533 | B2 | 2/2012 | Lavallee |
| 8,152,726 | B2 | 4/2012 | Amiot et al. |
| 8,165,658 | B2 | 4/2012 | Waynik et al. |
| 8,251,908 | B2 | 8/2012 | Vortman et al. |
| 8,311,611 | B2 | 11/2012 | Csavoy et al. |
| 8,374,674 | B2 | 2/2013 | Gertner |
| 8,409,099 | B2 * | 4/2013 | Vitek ...................... A61B 8/4281 600/439 |
| 8,444,564 | B2 | 5/2013 | Mahfouz et al. |
| 8,556,834 | B2 | 10/2013 | Gertner |
| 8,565,860 | B2 | 10/2013 | Kimchy et al. |
| 8,626,267 | B2 | 1/2014 | Lavallee |
| 8,675,939 | B2 | 3/2014 | Moctezuma de la Barrera |
| 8,771,188 | B2 | 7/2014 | Schers et al. |
| 8,774,900 | B2 | 7/2014 | Buly et al. |
| 8,814,810 | B2 | 8/2014 | Roche et al. |
| 8,864,686 | B2 | 10/2014 | Roche et al. |
| 8,880,152 | B2 | 11/2014 | Lavallee |
| 8,909,325 | B2 | 12/2014 | Kimchy et al. |
| 8,939,909 | B2 | 1/2015 | Wegner |
| 9,060,794 | B2 | 6/2015 | Kang et al. |
| 9,101,394 | B2 | 8/2015 | Arata et al. |
| 9,174,065 | B2 | 11/2015 | Gertner |
| 9,196,046 | B2 | 11/2015 | Meyer |
| 9,220,571 | B2 | 12/2015 | Lavallee |
| 9,244,169 | B2 | 1/2016 | Fan et al. |
| 9,248,001 | B2 | 2/2016 | Colombet et al. |
| 9,352,171 | B2 | 5/2016 | Gertner |
| 9,387,276 | B2 | 7/2016 | Sun et al. |
| 9,572,548 | B2 | 2/2017 | Moctezuma de la Barrera |
| 9,597,058 | B2 | 3/2017 | Kanayama et al. |
| 2002/0122536 | A1 | 9/2002 | Kerrien et al. |
| 2003/0036702 | A1 * | 2/2003 | Davidsen ................ A61B 8/00 600/437 |
| 2004/0236223 | A1 * | 11/2004 | Barnes ................ A61B 5/0048 600/459 |
| 2006/0004290 | A1 * | 1/2006 | Smith .................. A61B 8/4483 600/459 |
| 2007/0265690 | A1 | 11/2007 | Lichtenstein et al. |
| 2008/0200810 | A1 | 8/2008 | Buchalter |
| 2008/0208055 | A1 | 8/2008 | Bertram et al. |
| 2009/0124871 | A1 | 5/2009 | Arshak et al. |
| 2009/0306497 | A1 | 12/2009 | Manzke et al. |
| 2010/0268072 | A1 | 10/2010 | Hall et al. |
| 2010/0286518 | A1 | 11/2010 | Lee et al. |
| 2011/0092862 | A1 | 4/2011 | Chivers |
| 2012/0029345 | A1 | 2/2012 | Mahfouz et al. |
| 2012/0238875 | A1 | 9/2012 | Savitsky et al. |
| 2013/0060121 | A1 | 3/2013 | Patwardhan et al. |
| 2013/0144135 | A1 | 6/2013 | Mahfouz et al. |
| 2013/0150863 | A1 | 6/2013 | Baumgartner |
| 2013/0218013 | A1 | 8/2013 | Barthe et al. |
| 2014/0163377 | A1 | 6/2014 | Kang et al. |
| 2015/0018682 | A1 | 1/2015 | Schers et al. |
| 2015/0038613 | A1 | 2/2015 | Sun et al. |
| 2015/0080725 | A1 | 3/2015 | Wegner |
| 2015/0133787 | A1 | 5/2015 | Wegner |
| 2015/0133788 | A1 | 5/2015 | Mauldin, Jr. et al. |
| 2015/0164467 | A1 | 6/2015 | Suetoshi et al. |
| 2015/0182191 | A1 | 7/2015 | Caluser et al. |
| 2016/0000409 | A1 | 1/2016 | Bruder et al. |
| 2016/0100821 | A1 | 4/2016 | Eggers et al. |
| 2016/0242736 | A1 | 8/2016 | Freiburg et al. |
| 2016/0270763 | A1 | 9/2016 | Hayes et al. |
| 2018/0126677 | A1 | 5/2018 | Zhao et al. |

FOREIGN PATENT DOCUMENTS

| | | |
|---|---|---|
| JP | 2011-177461 A | 9/2011 |
| JP | 2013-056156 A | 3/2013 |
| WO | 2002/024094 A2 | 3/2002 |
| WO | 2007/023477 A2 | 3/2007 |
| WO | 2009/063421 A1 | 5/2009 |
| WO | 2014/150780 A2 | 9/2014 |
| WO | 2014/150961 A1 | 9/2014 |
| WO | 2014/186904 A1 | 11/2014 |
| WO | 2016/044830 A1 | 3/2016 |
| WO | 2016/149427 A1 | 9/2016 |

OTHER PUBLICATIONS

Choe, J.W., et al., "Volumetric real-time imaging using a CMUT ring array," IEEE Transactions on Ultrasonics, Ferroelectrics, and Frequency Control, 59(6):1201-1211, Jun. 2012.

(56) References Cited

OTHER PUBLICATIONS

Extended Search Report dated Jun. 18, 2019 for European Application No. 16854507.7, filed on Oct. 7, 2016 (11 pages).

\* cited by examiner

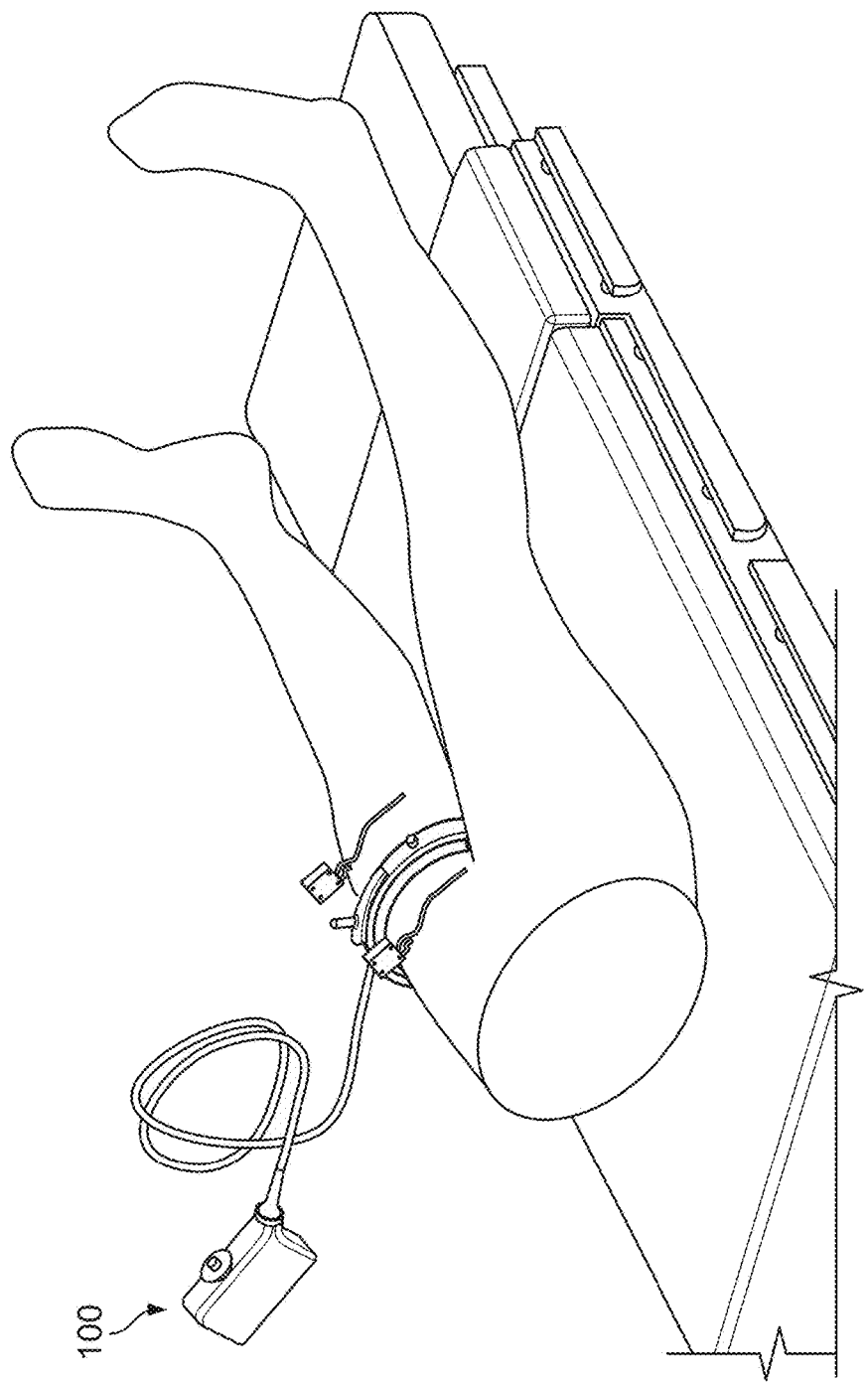

PISTON DESIGN
- Basic Design Equations
  - Fresnel Distance $FD = a^2/\lambda$ (4-6 cm)
  - Depth-of-Field $DOF = 4/3\, FD$ (5.3-8 cm)
  - Attenuation 1.0 dB/cm/MHz two-way (0-40 dB)

Some COTS Candidates:
2.25 MHz, 0.50"
5.0 MHz, 0.33"
7.5 MHz, 0.25"

| Frequency (MHz) | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 0.001 | FALSE | FALSE | FALSE | FALSE | FALSE | FALSE | FALSE | FALSE | FALSE | FALSE | FALSE | FALSE | FALSE | FALSE | FALSE |
| 0.002 | FALSE | FALSE | FALSE | FALSE | FALSE | FALSE | FALSE | FALSE | FALSE | FALSE | FALSE | FALSE | FALSE | FALSE | FALSE |
| 0.003 | FALSE | FALSE | FALSE | FALSE | FALSE | FALSE | FALSE | FALSE | FALSE | FALSE | FALSE | FALSE | FALSE | FALSE | FALSE |
| 0.004 | FALSE | FALSE | FALSE | FALSE | FALSE | FALSE | FALSE | FALSE | FALSE | FALSE | FALSE | FALSE | FALSE | FALSE | FALSE |
| 0.005 | FALSE | FALSE | FALSE | FALSE | FALSE | FALSE | FALSE | FALSE | FALSE | FALSE | FALSE | FALSE | FALSE | FALSE | FALSE |
| 0.006 | FALSE | FALSE | FALSE | FALSE | FALSE | FALSE | FALSE | TRUE | FALSE | FALSE | FALSE | FALSE | FALSE | FALSE | FALSE |
| 0.007 | FALSE | FALSE | FALSE | FALSE | FALSE | FALSE | TRUE | TRUE | FALSE | FALSE | FALSE | FALSE | FALSE | FALSE | FALSE |
| 0.008 | FALSE | FALSE | FALSE | FALSE | FALSE | TRUE | TRUE | FALSE | FALSE | FALSE | FALSE | FALSE | FALSE | FALSE | FALSE |
| 0.009 | FALSE | FALSE | FALSE | FALSE | TRUE | TRUE | FALSE | FALSE | FALSE | FALSE | FALSE | FALSE | FALSE | FALSE | FALSE |
| 0.01  | FALSE | FALSE | FALSE | TRUE | TRUE | FALSE | FALSE | FALSE | FALSE | FALSE | FALSE | FALSE | FALSE | FALSE | FALSE |
| 0.011 | FALSE | FALSE | TRUE | TRUE | FALSE | FALSE | FALSE | FALSE | FALSE | FALSE | FALSE | FALSE | FALSE | FALSE | FALSE |
| 0.012 | FALSE | TRUE | TRUE | FALSE | FALSE | FALSE | FALSE | FALSE | FALSE | FALSE | FALSE | FALSE | FALSE | FALSE | FALSE |
| 0.013 | FALSE | TRUE | FALSE | FALSE | FALSE | FALSE | FALSE | FALSE | FALSE | FALSE | FALSE | FALSE | FALSE | FALSE | FALSE |
| 0.014 | FALSE | FALSE | FALSE | FALSE | FALSE | FALSE | FALSE | FALSE | FALSE | FALSE | FALSE | FALSE | FALSE | FALSE | FALSE |
| 0.015 | FALSE | FALSE | FALSE | FALSE | FALSE | FALSE | FALSE | FALSE | FALSE | FALSE | FALSE | FALSE | FALSE | FALSE | FALSE |
| 0.016 | TRUE | FALSE | FALSE | FALSE | FALSE | FALSE | FALSE | FALSE | FALSE | FALSE | FALSE | FALSE | FALSE | FALSE | FALSE |
| 0.017 | TRUE | FALSE | FALSE | FALSE | FALSE | FALSE | FALSE | FALSE | FALSE | FALSE | FALSE | FALSE | FALSE | FALSE | FALSE |
| 0.018 | TRUE | FALSE | FALSE | FALSE | FALSE | FALSE | FALSE | FALSE | FALSE | FALSE | FALSE | FALSE | FALSE | FALSE | FALSE |
| 0.019 | TRUE | FALSE | FALSE | FALSE | FALSE | FALSE | FALSE | FALSE | FALSE | FALSE | FALSE | FALSE | FALSE | FALSE | FALSE |
| 0.02  | FALSE | FALSE | FALSE | FALSE | FALSE | FALSE | FALSE | FALSE | FALSE | FALSE | FALSE | FALSE | FALSE | FALSE | FALSE |
| 0.021 | FALSE | FALSE | FALSE | FALSE | FALSE | FALSE | FALSE | FALSE | FALSE | FALSE | FALSE | FALSE | FALSE | FALSE | FALSE |
| 0.022 | FALSE | FALSE | FALSE | FALSE | FALSE | FALSE | FALSE | FALSE | FALSE | FALSE | FALSE | FALSE | FALSE | FALSE | FALSE |
| 0.023 | FALSE | FALSE | FALSE | FALSE | FALSE | FALSE | FALSE | FALSE | FALSE | FALSE | FALSE | FALSE | FALSE | FALSE | FALSE |
| 0.024 | FALSE | FALSE | FALSE | FALSE | FALSE | FALSE | FALSE | FALSE | FALSE | FALSE | FALSE | FALSE | FALSE | FALSE | FALSE |
| 0.025 | FALSE | FALSE | FALSE | FALSE | FALSE | FALSE | FALSE | FALSE | FALSE | FALSE | FALSE | FALSE | FALSE | FALSE | FALSE |

Fresnel distance, DOF, and attenuation all satisfied

FIG. 4

(Side View)

(Isometric Projection)

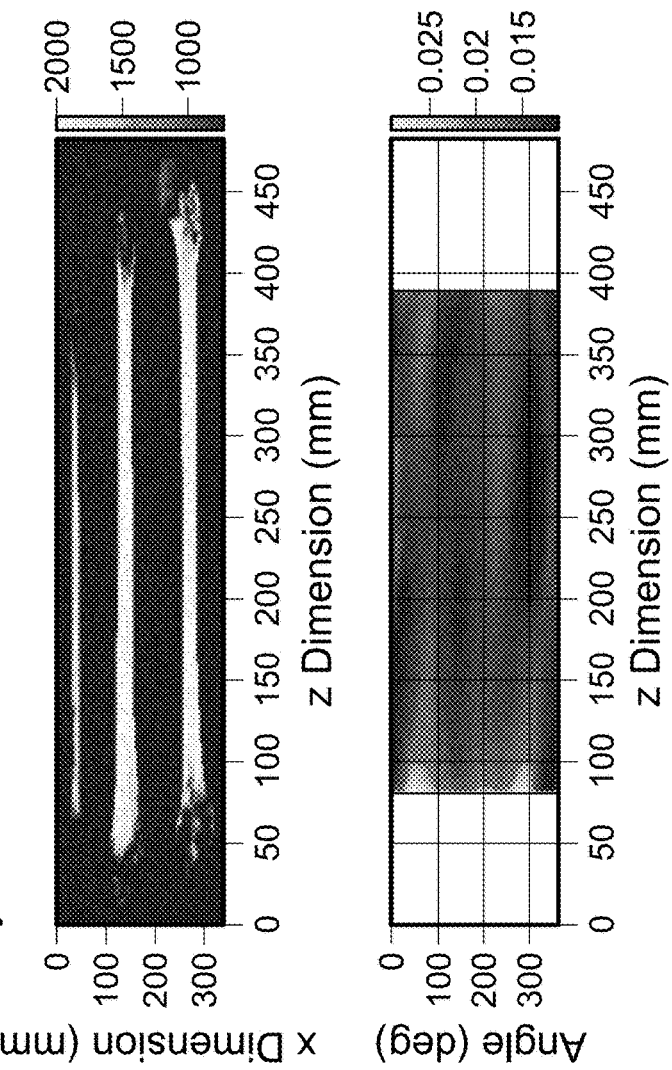
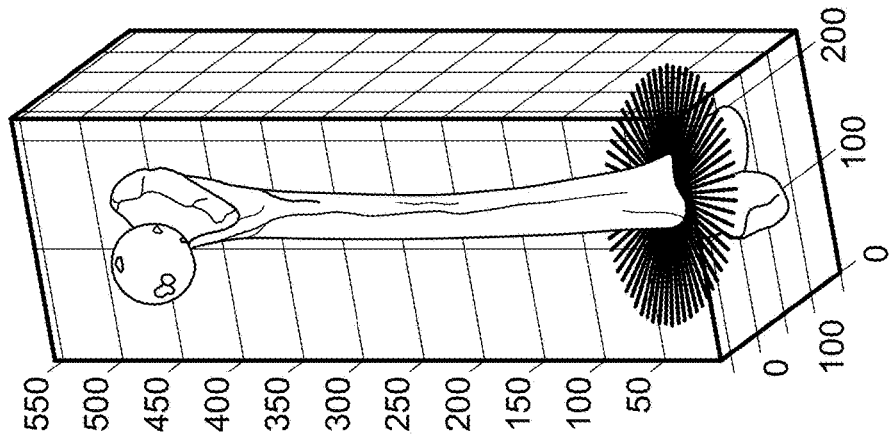
- High rate ultrasound specular bone response to locate bone surface w.r.t. array
- Correlate Surface Features with US echoes to determine US array position w.r.t. CT coordinate system
Bones have unique features
6DOF CT Pattern Generator
FIG. 7B

RTT Implementation Thoughts

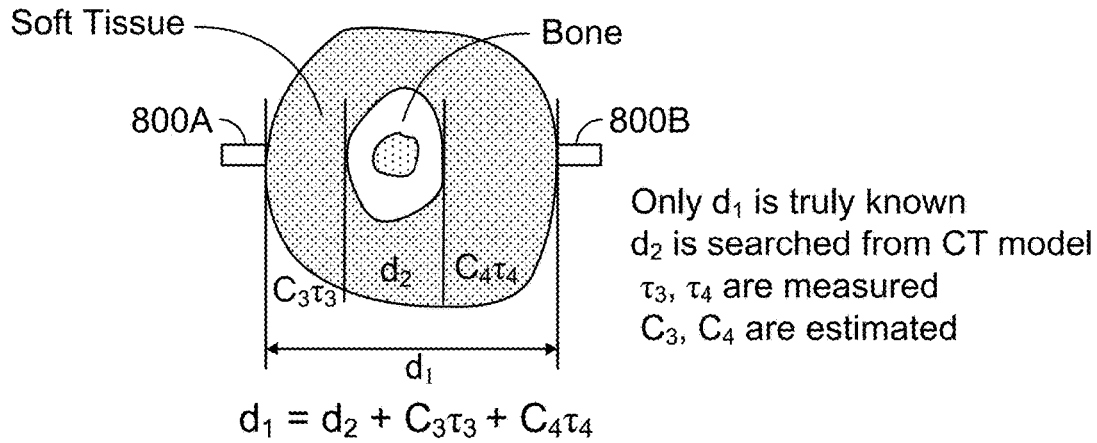

Only $d_1$ is truly known
$d_2$ is searched from CT model
$\tau_3, \tau_4$ are measured
$C_3, C_4$ are estimated $$d_1 = d_2 + C_3\tau_3 + C_4\tau_4$$

Basis of Objective Function

FIG. 8A

$n^{th}$ Objective Function for N Pairs of Elements

$$f_n = d_{n,1} - d_{n,2}(x,y,z,\phi,\theta,\psi) - C_{n,3}\tau_{n,3} - C_{n,4}\tau_{n,4}$$

Actually 6 unknowns in CT model orientation
Constrain unknowns so solver can make a lock

FIG. 8B

ACOUSTIC ORTHOPEDIC TRACKING SYSTEM AND METHODS

CROSS REFERENCE TO RELATED APPLICATIONS

This patent document claims the benefit of U.S. Provisional Patent Application No. 62/239,169, filed Oct. 8, 2015. The entire content of the before-mentioned patent application is incorporated by reference as part of the disclosure of this application.

TECHNICAL FIELD

This patent document relates to systems, devices, and processes that use acoustic energy for diagnostics and therapy.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Fundamentally, ultrasound imaging operates the same principle as sound navigation and ranging (SONAR) in which a transmission of one or more acoustic waves results in one or more echoes from structures that are received and processed to form an image. Some factors, including inadequate spatial resolution and tissue differentiation, can lead to less than desirable image quality using conventional techniques of ultrasound imaging, which can limit its use for many clinical indications or applications. Compared to other imaging modalities, the real-time, non-ionizing, portable, and relatively low-cost features of ultrasound imaging make it attractive for biomedical applications.

SUMMARY

Systems, devices, and methods are disclosed for acquiring and providing information about orthopedic features of a body using acoustic energy. In some aspects, an acoustic orthopedic tracking system includes portable acoustic transducers to obtain orthopedic position information for feeding the information to an orthopedic surgical system for surgical operations.

In some aspects of the present technology, an acoustic orthopedic tracking system (OTS) includes an engineered acoustic array and supporting structure, in which the acoustic array provides an acoustic coupling medium as it relates to the transducer structure and the body part of interest. For example, a plurality of ultrasound transducers of the acoustic array structure transmit and receive ultrasound waves that are used to track the shape, location, and movement of bone in real-time. The received ultrasound echoes are processed to estimate the six degrees of freedom (6 DoF) location coordinates of the bone, which in some implementations may be combined with 3D tomographic imaging information. Information provided by the acoustic OTS may be used in medical treatment planning, medical procedures, surgical procedures, fully automated surgery, surgery assisted by robots, and biometrics.

In some aspects, a method for orthopedic tracking includes transmitting ultrasound pulses from a plurality of ultrasound transducers, e.g., sequentially one-at-a-time, simultaneously, or in a time-staggered or time-delayed pattern. Each transmission is accompanied by receptions of acoustic echoes on one or more transducer elements corresponding to a single transmission. The received echoes are amplified, filtered, and temporally sampled sufficiently to retain all relevant spectral information corresponding to the echoes from soft tissue and bone as is dictated by the Nyquist sampling theorem. Received echoes are digitally sampled and stored for processing. In some embodiments, the waveforms used include spread-spectrum waveforms, which are highly robust waveforms to deleterious factors such as frequency and depth-dependent attenuation, electronic noise, cross-talk between adjacent channels, and acoustic reverberation. Due to the specular nature of bone reflections, echoes from the tissue-bone interface will present a different and identifiable echo signature compared to echoes from soft tissue and from within the bone itself All bones, for example, the femur and tibia, have unique cross-sectional patterns over the length of the bone. The specular acoustic echo pattern from bone sampled at one or more points on the bone are matched to a library of patterns sampled according to the array geometry to determine the topography of the bone, and thus, estimate the orientation of the bone in 6 DoF coordinate space according to the location of the transducers relative to a fixed point in space. Signal processing is applied to the amplitude and phase information present in the received radio-frequency (RF) echoes to determine a pattern match and identify 6 DoF coordinates of the bone being tracked, estimates of the tissue and bone velocity and acceleration along the axis of each transducer, as well parameters associated with the pattern match, and estimates of the uncertainty in the identified 6 DoF coordinates.

In some applications, for example, the present technology can be used to track the tibia and femur bones in the leg during computer assisted surgery (CAS) of the knee, including, but not limited to, total knee arthroplasty (TKA) and total knee replacement (TKR). Current state-of-the-art TKA and TKR procedures require surgical placement of an alignment rod into both the tibia and femur for rigidly tracking both bones using external optical trackers. For example, to place the alignment rod, a small incision is made in the skin, a hole is drilled into the bone, and the rod is screwed into the hole. The procedure is invasive, resulting in unsightly scarring on the skin. It potentially compromises the integrity of the bone, particularly for elderly patients. It is a site of potential infection, which can lead to post-surgical complications. The disclosed technology is envisioned to replace this invasive tracking with non-invasive tracking.

BRIEF DESCRIPTION OF THE DRAWINGS

FIG. 3B is another view of components shown in FIG. 3A.

FIG. 4 shows a trade study diagram to explore element diameters and center frequencies that can be used for a particular set of constraints for an example acoustic OTS.

FIG. 7B shows another view of radial patterns for a human femur.

FIG. 8A shows a simple arrangement of two transducers transmitting and receiving echoes though soft tissue that contains a bone.

FIG. 8B shows an example objective function associated with each transducer or beam or collection of transducers of collections of beams.

DETAILED DESCRIPTION

Figure 1A:
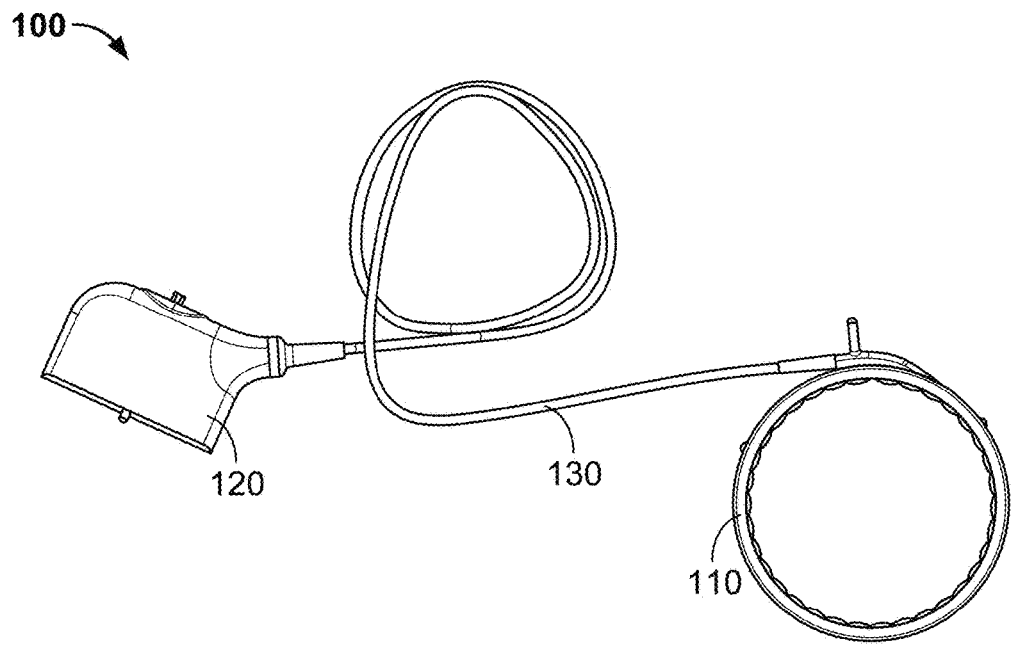
FIG. 1A shows a diagram of an exemplary acoustic orthopedic tracking system (OTS) of the present technology including an acoustic transducer array and supporting structure used for acquiring acoustic imaging data.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). Propagation of the acoustic waveform in the medium toward the target volume can encounter structures that cause the acoustic waveform to become partly reflected from a boundary between two mediums (e.g., differing biological tissue structures) and partially transmitted. The reflection of the transmitted acoustic waveform can depend on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

Acoustic imaging system transducers may employ an array of piezoelectric elements to transmit an acoustic pulse toward the target VOI (e.g., target biological tissue) and receive the returned acoustic signals (echoes) that return from scattering structures within. In such systems, the transducer array functions as the aperture of the imaging system. The acoustic waveforms (e.g., ultrasound pulses) can be electronically steered and focused through a plane or volume and used to produce a 1D, 2D and/or 3D map of the returned echoes used to form an image of the target. Beamforming can occur both in transmit and receive. In transmit, for example, beamforming can include the utilization of phase differences between channels to form, focus and steer the beam. In some implementations, the ultrasound pulse and the returned echoes transmitted and received at the transducer array can be individually delayed in time at each transducer of the array to act as a phased array.

For example, acoustic wave speed and acoustic impedance differences can exist at the interface between the transducer and the medium to receive the acoustic waveform, e.g., referred to as the receiving medium, for propagation of the acoustic waveform toward the target volume. These differences disrupt the transmission of the acoustic signal and reception of the returned echoes, diminishing the quality of results or ability to perform acoustic imaging, range-Doppler measurement, or therapeutic applications. Acoustic impedance differences are caused by differing material properties (e.g., material density) of the two mediums and the acoustic wave velocity, such that a substantial amount of the emitted acoustic energy will be reflected at the interface, rather than transmitted in full across the interface.

In conventional real aperture ultrasound imaging systems, the quality of images directly depends on the acoustic field generated by the transducer of the ultrasound system, and the image is typically acquired sequentially, one axial image line at a time (i.e., scan of the target area range slice by slice). This sets limits on the frame rate during imaging that may be detrimental in a variety of real-time ultrasound imaging applications, e.g., including the imaging of moving targets.

To address limitations with conventional real aperture ultrasound imaging, synthetic aperture ultrasound imaging can be used to improve the quality of ultrasound images. A "synthetic aperture" is the concept in which the successive use of one or more smaller, real apertures (sub-apertures) to examine a VOI, whose phase centers are moved along a known one-dimensional (1D), two-dimensional (2D), and/or three-dimensional (3D) path of a particular or arbitrary shape, to realize a larger effective (non-real) aperture for acquiring an image. The synthetic aperture can be formed by mechanically altering the spatial position of the electroacoustic transducer (e.g., transducer array) to the successive beam transmission and/or receiving locations, by electronically altering the phase center of the successive beam transmission and/or receiving locations on the electroacoustic transducer array, or by a combination of any of above. Synthetic aperture-based imaging was originally used in radar systems to image large areas on the ground from aircraft scanning the area of interest from above. Synthetic aperture focusing in ultrasound imaging is based on the geometric distance from the ultrasound transmitting elements to the VOI location and the distance from that location back to the ultrasound receiving element. In ultrasound imaging, the use of the synthetic aperture enables the focusing on a point in the target region by analyzing the received amplitude and phase data of the returned echoes (e.g., mono-static and bi-static echoes), recorded at each of a plurality of transmitter and receiver positions from all directions, to provide information about the entire area. Since the direction of the returned echoes cannot be determined from one receiver channel alone, many receiver channels are used to determine the information contained in the returning echoes, which are processed across some or all of the channels to ultimately render information used to produce the image of the target region.

The disclosed systems, devices, and methods for acoustic orthopedic tracking may also include techniques for synthetic aperture acoustic imaging and/or range-Doppler measurements. In some implementations, the disclosed technology includes an architecture designed for generating, transmitting, receiving, and processing coherent, spread-spectrum, instantaneous-wideband, coded waveforms in synthetic aperture ultrasound (SAU) applications. Examples of such pertaining to the generation, transmission and data processing of coherent, spread-spectrum, instantaneous-wideband, coded waveforms and synthetic aperture ultrasound are described in the U.S. Pat. No. 8,939,909 and U.S. Patent Application Publication No. 2015/0080725, which are incorporated by reference as part of this patent document.

For example, the use of coherent waveforms in implementations of the SAU systems can permit the complex correlation of a portion of, or the entire, echo return with a selected reference signal, such as, for example, the transmitted waveform. Such coherent complex correlations permit the reduction of image and signal artifacts and the extraction of data at lower signal-to-noise ratios and in the presence of interference.

The use of spread-spectrum signals in implementations of the SAU systems can allow the definitive design of acoustic waveforms that have deliberate and explicit amplitude and phase frequency content. For example, by explicitly defining the amplitude and/or phase of each frequency component of the spread-spectrum composite acoustic waveforms can be constructed such that signal and information processing techniques can be employed to extract the maximal amount of information from the echo returns, e.g., approaching mathematical limits.

The use of instantaneous coherent, wideband, spread-spectrum, coded waveforms in implementations of the SAU systems can enable the capture of all available information during each transmit-receive interval, e.g., thereby minimizing the corruption of the returned signal by the inhomogeneous, dynamic nature of living biological specimens, and by motion induced artifacts of the collection process. Additionally, for example, fundamental physical parameters (e.g., such as bulk modulus, density, attenuation, acoustic impedance, amplitude reflections, group delay, or other) can be extracted by using signal and information processing methods of the disclosed technology to enable differentiation and classification of the tissue in the VOI. For example, some signal and information processing methods of the disclosed SAU technology may include inverse mathematical techniques operating on the received frequency and angular dependent wideband, spread-spectrum, synthetic aperture received signal echoes for differentiating and/or classifying tissue in the VOI, as well as expert system techniques, e.g., deterministic, support vector network and neural network techniques.

Explicit amplitude and/or phase coding of each frequency component of waveforms in implementations of the disclosed SAU systems can provide multiple benefits. For example, amplitude coding allows for the explicit compensation of the frequency-dispersive properties of the transducer array and of the acoustic propagation channel. The amplitude and/or phase coding of each frequency component permits deterministic beamforming and steering of wide-instantaneous waveforms. Explicit amplitude and phase coding of each frequency component of an exemplary transmitted signal permits the minimization of the peak-to-average power ratio (PAPR), and the spreading of the acoustic power over a wide band, e.g., to minimize deleterious biological effects. For example, by explicitly defining the amplitude and/or phase of each frequency component of spread-spectrum signals, waveforms can be constructed that may be transmitted simultaneously, which exhibit minimal interference with each other, such that signal and information processing techniques can be employed to recover the received signal associated with each individual transmitted waveform. Further, the coded, spread-spectrum acoustic waveforms of the disclosed SAU technology can allow for motion compensation due to particular ambiguity properties of these waveforms.

Systems, devices, and methods are disclosed for acquiring and providing information about orthopedic features of a body using acoustic energy. In some aspects, an acoustic orthopedic tracking system includes portable device including an acoustic transducer array that conforms to the subject's body part to obtain orthopedic position information and a signal and data processing unit to produce a data set identifying shape, location, and movement information of bone, e.g., for feeding the information in real-time to an external device for a diagnostic or therapeutic application, e.g., such as an orthopedic surgical system for surgical operations.

While the disclosed embodiments are described herein primarily pertaining to tracking orthopedic anatomical structures using the acoustic tracking systems of the present technology to facilitate understanding of the underlying concepts, it is understood that the disclosed embodiments can also include tracking of other anatomical or non-anatomical structures from which specular information can be obtained, which may include, but are not limited to, pliable regions of a body, a body wall, or organs (e.g., kidneys, bladder, etc.).

Exemplary Embodiments of the Disclosed Acoustic OTS

Figure 1B:
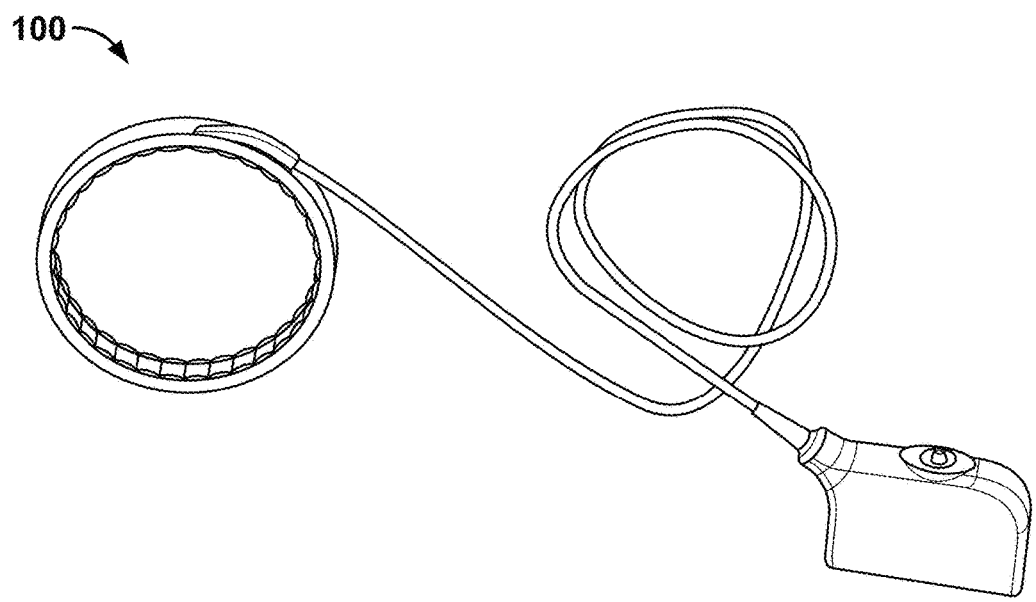
FIG. 1B shows an image of an example acoustic OTS.

FIGS. 1A and 1B show a diagram and an image of an exemplary acoustic orthopedic tracking system (OTS) 100, respectively. The acoustic OTS 100 includes an acoustic transducer array and supporting structure 110, also referred to as the "structure", configured to conform to a user's body, including an arm or leg extremity, head, neck, breast, torso or other body part, and used by the acoustic OTS 100 for acquiring acoustic imaging data, e.g., for producing an acoustic image, range-Doppler measurements, and/or feed into a therapeutic systems such as an orthopedic surgical system for affecting surgical operations. The acoustic OTS 100 includes a signal interface module 120 to provide an interface between the acoustic transducer array structure 110 and a signal generator and processing device 140 (shown in FIG. 1C). The signal interface module 120 can include a signal processing circuitry and components to amplify, multiplex, convert analog-to-digital (A/D) and/or convert digital-to-analog (D/A), or otherwise condition the electrical signals to be transmitted by and received from the acoustic transducer elements of the array for signal transmission and reception with the signal generator and processing device 140.

Figure 1C:
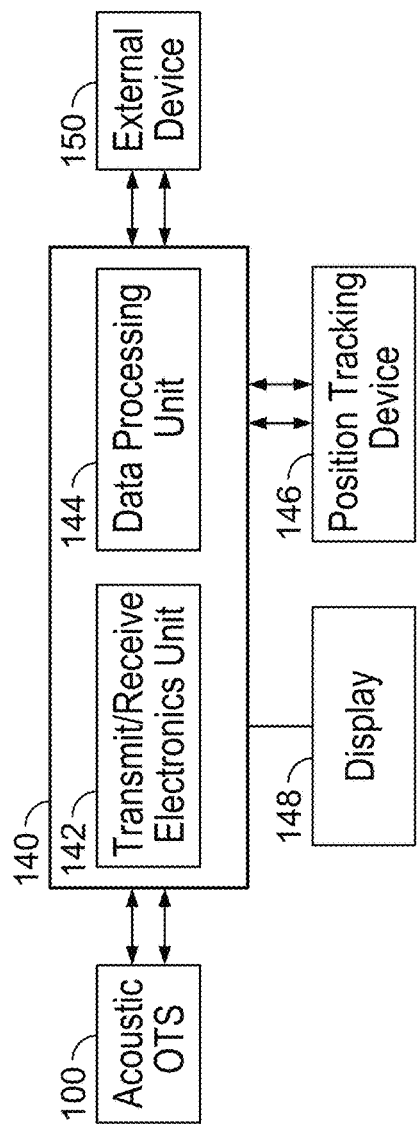
FIG. 1C shows a block diagram of an example embodiment of an acoustic OTS implemented in conjunction with an external device or system.

The signal generator and processing device 140 includes a transmit and receive electronics unit 142, and a data processing unit 144, as shown in the block diagram of FIG. 1C. Some examples of the transmit and receive electronics unit 142 (of the generator and processing device 140) of the present technology are described in International (PCT) Application Publication No. WO 2016/149427, which is incorporated by reference in this patent document. One example includes a synthetic aperture ultrasound/acoustic (SAU) system 100 shown in FIG. 1 of the above PCT Publication (reproduced as FIG. 1E in this document), in which the SAU system 100 includes a transmit/receive electronics module (TREM) 110E in electrical communication with an acoustic probe device 120E and with a data processing unit resident on the TREM 110E or an external computer device 130E. The TREM 110E is configured to generate the individual coded waveforms on multiple channels transferred to the probe device for transmitting and receiving one or more composite waveforms (e.g., coherent, spread-spectrum, instantaneous-wideband, coded waveforms) based on the individual generated coded waveforms. In implementations of the acoustic OTS 100, the probe device can include the acoustic transducer array structure 110. The TREM 110E includes a waveform generator unit that includes a function generator and an arbitrary waveform generator (AWG). The TREM 110E includes a system control unit to control the waveform generator unit for the synthesis of individual coded waveforms. The TREM includes signal conditioning and processing circuitry to amplify, select, and/or convert analog and digital signals, e.g., which can include analog/digital converters, multiplexers, amplifiers, etc. The TREM 110E includes a data processing unit (e.g., processor or microcontroller, and memory) is configured to transfer data with a central processing unit (CPU) of the computer 130E, e.g., such as executable instructions on waveform synthesis or probe control, and/or acquired or processed data.

Referring back to FIG. 1A, the acoustic OTS 100 includes a connector 130 (e.g., cable) in communication with the acoustic transducer array structure 110 and the signal interface module 120 to provide data communications (e.g., transfer the electrical signals) between the structure 110 and module 120. In some implementations of the connector 130, for example, the connector 130 is strain relieved and includes attachable and detachable termini to be coupled to the structure 110 with one or more seals to prevent contaminants from intruding. In some embodiments, for example, the outer covering material of the connector 130 can be configured of autoclavable material to allow for sterilization. In some embodiments, for example, the connector 130 can be permanently attached to the structure 110, e.g., which may include the autoclavable material on the outer covering, or be configured of materials compatible with being disposed (e.g., for one-time use).

FIG. 1C shows a block diagram of an example embodiment of a system of the present technology that may be implemented in conjunction with an external device or system 150, e.g., such as an orthopedic surgical system for surgical operations. The system includes the acoustic OTS 100 and the signal generator and processing device 140. The acoustic transducer array structure 110 is connected (e.g., via the signal interface module 120) to the transmit and receive electronics unit 142 of the signal generator and processing device 140, e.g., through a bi-directional analogic and/or digital signal lines. The transmit and receive electronics unit 142 can include circuitry and electronic components including, but not limited to, power amplifiers, RF amplifiers, variable gain amplifiers, diplexers, multiplexers, digital to analog converters, analog to digital converters, ASICs, FPGAs, DSPs, RF transformers, analog filters, digital filters, Ethernet circuitry, PCI circuitry, digital buffers, RAM, non-volatile memory, communication components, and power supply electronics. The transmit and receive electronics unit 142 is in communication with a data processing unit 144 of the signal generator and processing device 140 to process and store data of the device 140.

In some embodiments of the device 140, the data processing unit 144 may be resident on one or more computers (e.g., desktop computer, laptop computer, a network of computer devices in data communication with each other via the Internet (e.g., in the 'cloud'), or other computing device including, but not limited to, a smartphone, tablet, or wearable computing/communications device). In some embodiments of the device 140, the data processing unit 144 may be resident in a device structure (e.g., housing) that includes the transmit and receive electronics unit 142. The transmit and receive electronics unit 142 is in communication with a data processing unit 144 via a digital interface, e.g., which may be any interface or collection of interfaces including but not limited to USB, FireWire, Ethernet, PCI, IEEE 1394 Serial, Wi-Fi, Fiber Channel, fiber optics, a wireless bus, a serial bus, or a parallel bus.

The data processing unit 144 may include a programmable processing unit and storage device that may include, but is not limited to, the following components, e.g., one or more processors, serial processors, parallel processors, math co-processors, general purpose graphical processing units (GPUs), FPGAs, ASICSs, DSPs, nonvolatile memory, RAM, digital buffers, storage devices, hard drives, USB, FireWire, Ethernet, PCI, IEEE 1394 Serial, Wi-Fi, Fiber Channel, fiber optics, a wireless bus, a serial bus, external display adaptor, external display driver, a parallel bus, communications components, and power supply electronics. In some embodiments, for example, the device 140 may also include a display device 148, e.g., such as a monitor, speaker, or other device to produce a combination of visual, audio or haptic output. For example, in some embodiments, the display device 148 may be incorporated together with the data processing unit 144 when the data processing unit 144 is resident on a computer, e.g., such as in a single unit or separately through cabling to an external display.

The data processing unit 144 is configured to process the acquired acoustic data from the acoustic OTS 100 to produce a data set of the orthopedic structure (e.g., bone) or feature of the subject including biological and positional information, e.g., such as bone shape, density, location, orientation, and/or structural movement of features and the overall bone. The data processing unit 144 can provide the produced data set to the external device 150. For example, in some implementations, the system produces the data set for providing the information in real-time to the external device 150 for a diagnostic or therapeutic application.

Figure 1D:
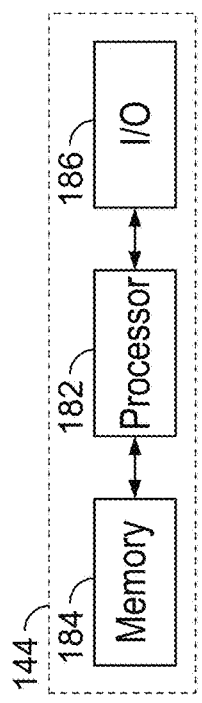
FIG. 1D shows a block diagram of an example embodiment of the data processing unit.
Figure 1E:
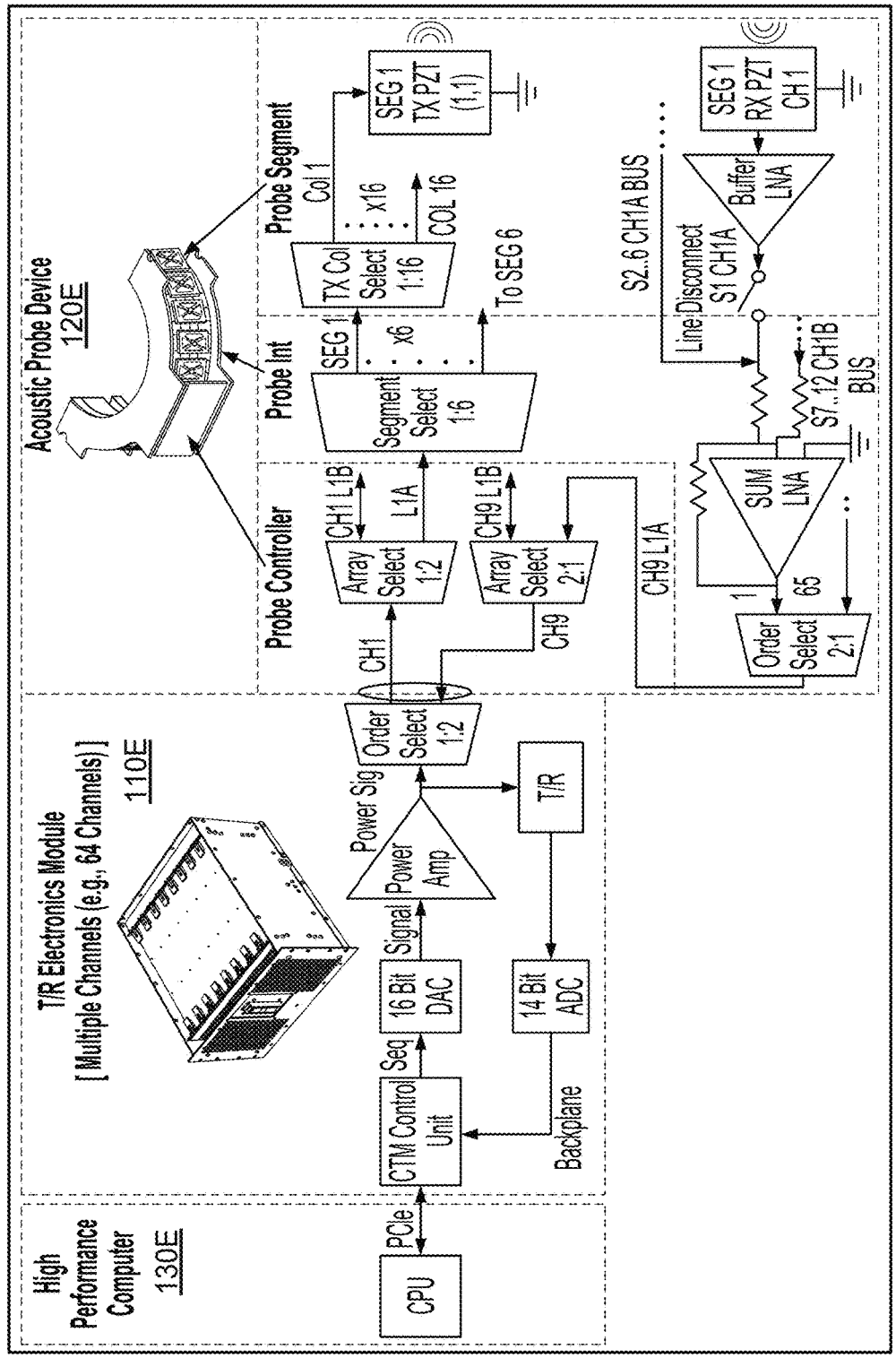
FIG. 1E shows an example synthetic aperture ultrasound/acoustic (SAU) system.

FIG. 1D shows a block diagram of an example embodiment of the data processing unit 144. In this example, the data processing unit 144 include a processor 182 to process data and a memory 184 in communication with the processor 182 to store data. For example, the processor 182 can include a central processing unit (CPU) or a microcontroller unit (MCU). For example, the memory 184 can include processor-executable code, which when executed by the processor 182, configures the data processing unit 144 to perform various operations, such as receiving information, commands, and/or data, processing information and data, and transmitting or providing information/data to another entity (e.g., external device 150). To support various functions of the data processing unit 144, the memory 184 can store other information and data, such as instructions, software, values, images, and other data processed or referenced by the processor 182. Various types of Random Access Memory (RAM) devices, Read Only Memory (ROM) devices, Flash Memory devices, and other suitable storage media can be used to implement storage functions of the memory 184. The memory 184 can store data and information of the data processing unit 144 and other units of the device 140. For example, the memory 184 can store device unit parameters, and hardware constraints, as well as software parameters and programs for operation on the device 140. In this example, the data processing unit 144 includes an I/O unit 186 that can allow communicative connectability of the data processing unit 144 to other units of the device 140. For example, I/O unit 186 can provide the data processing unit 144 to be in communications with other devices or systems, e.g., using various types of wired or wireless interfaces compatible with typical data communication standards, for example, including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O unit 186 can also provide communicative connectability of the data processing unit 144 to an external interface (e.g., the external device 150), source of data storage, or display device (e.g., the display device 148). The I/O unit 182 of the data processing unit 144 can also interface with other external interfaces, sources of data storage, and/or visual or audio display devices, etc., to retrieve and transfer data and information that can be processed by the processor 182, stored in the memory 184, or exhibited on an output unit of the device 140 (e.g., display device 148).

Referring back to FIG. 1C, in some embodiments, the system includes a position tracking device 146 to provide data to the data processing unit 144 used to determine the location coordinates, orientation, and other position and motion information of orthopedic structures of the body part with 6 DoF. The data processing unit 144 is in communication with the position tracking device 146, e.g., which can be configured through a digital interface. The position tracking device 146 is operable to track the position of the acoustic transducer array structure 110 of the acoustic OTS 100, e.g., including the position data of individual array elements 111 disposed in the structure 110. In some implementations for example, the position tracking device 146 can measure the position of the acoustic transducer array structure 110 by employing a non-contact sensor of the device 146 to obtain data of the structure 110 and/or body part to which the structure 110 is attached. Examples of the sensor of the position tracking device 146 can include, but is not limited to, an optical sensor (e.g., video camera, CCD, LED, etc.), a magnetic sensor (e.g., magnetometer, Hall effect sensor, MEMS-based magnetic field sensor, etc.), rate sensor (e.g., gyro sensor, accelerometer, etc.), and/or electromagnetic, radio-frequency, and/or microwave sensors, or other detectors. The position tracking device 146 is configured to provide the data processing unit 144 with processed coordinate information or with the raw sensor data for the data processing unit 144 to process to produce the coordinate information of the structure 111 and/or body part. The data processing unit 144 is operable to process the coordinate information with the received acoustic echoes obtained from the acoustic OTS 100 to generate 6 DoF coordinate estimates of the bone location, error estimates, acoustic images, and other relevant parameters of the orthopedic feature of the subject, e.g., with an update rate of 1 kHz or higher. The data-processed 6 DoF bone coordinates, orientation and/or other information (e.g., relevant to a specific application) may be communicated by the data processing unit 144 of the device 140 to the external device 150 for use by the external device 150.

One example of the position tracking device 146 can include the Stryker Surgical Navigation System (SNS), e.g., such as the Stryker NAV3i Platform. The Stryker NAV3i Platform includes digital camera technology, positional data processing devices, and multiple visual display monitors for tracking in real time. For example, the Stryker NAV3i Platform includes a navigation camera arm with one or more cameras (e.g., Built-in LiveCam) for imaging over a large range of motion, e.g., to accommodate various procedures and approaches. For example, the data processing devices of the Stryker NAV3i Platform include an industrial computer (e.g., with high-end processing speed and RAM) and IO Tablet user interface with touch capability, e.g., with wireless integration (e.g., DICOM query/retrieve and DICOM client functionality for smooth integration into a hospital network) and various I/O outputs (e.g., HDMI, etc.) to other data processing devices, e.g., such as the data processing unit 144 of the device 140.

Figures 1, 2A:
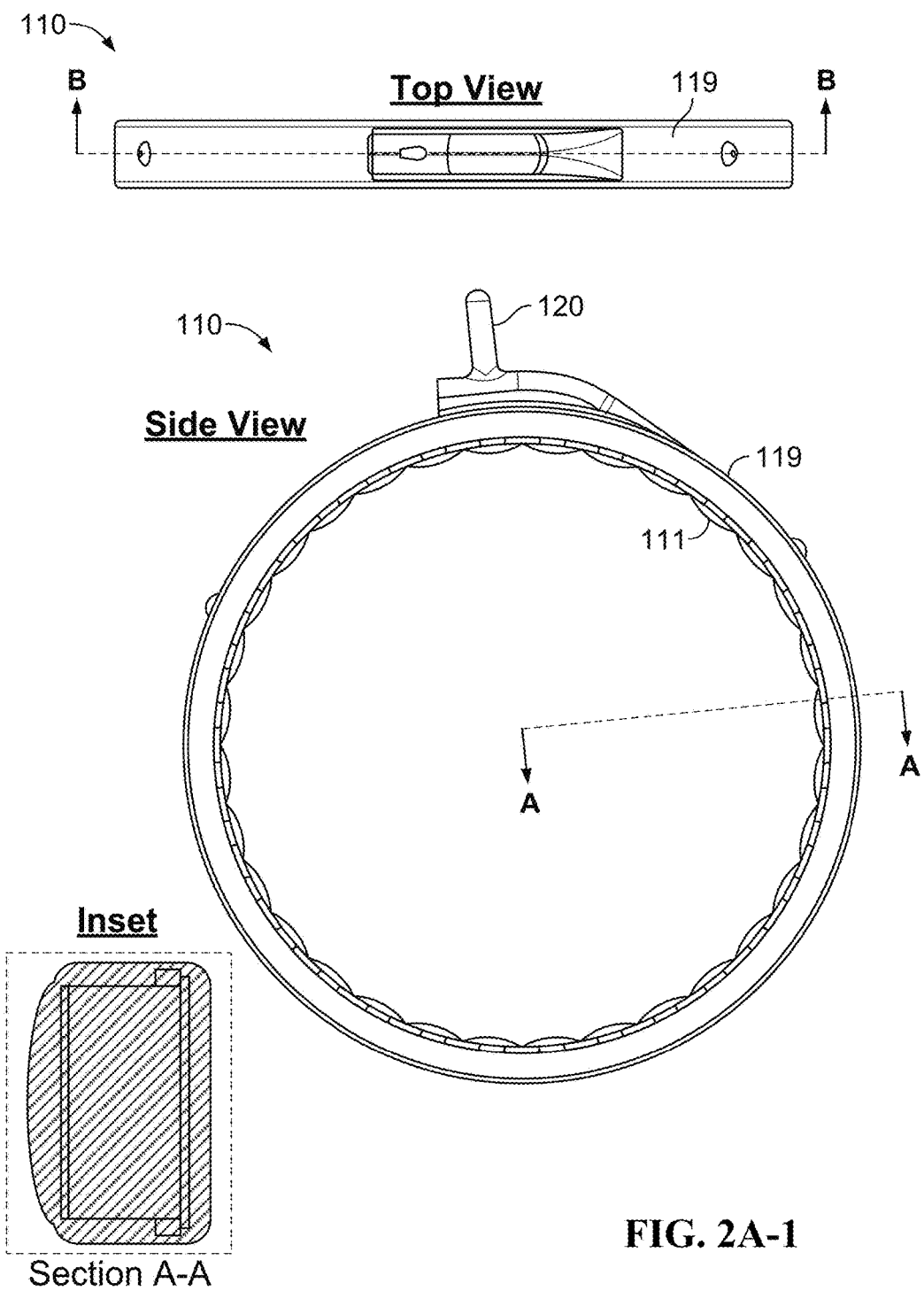
FIG. 2A shows a schematic of an exemplary acoustic transducer array structure of the present technology, showing top, side and cross-sectional views of the structure.
Figures 2, 2A:
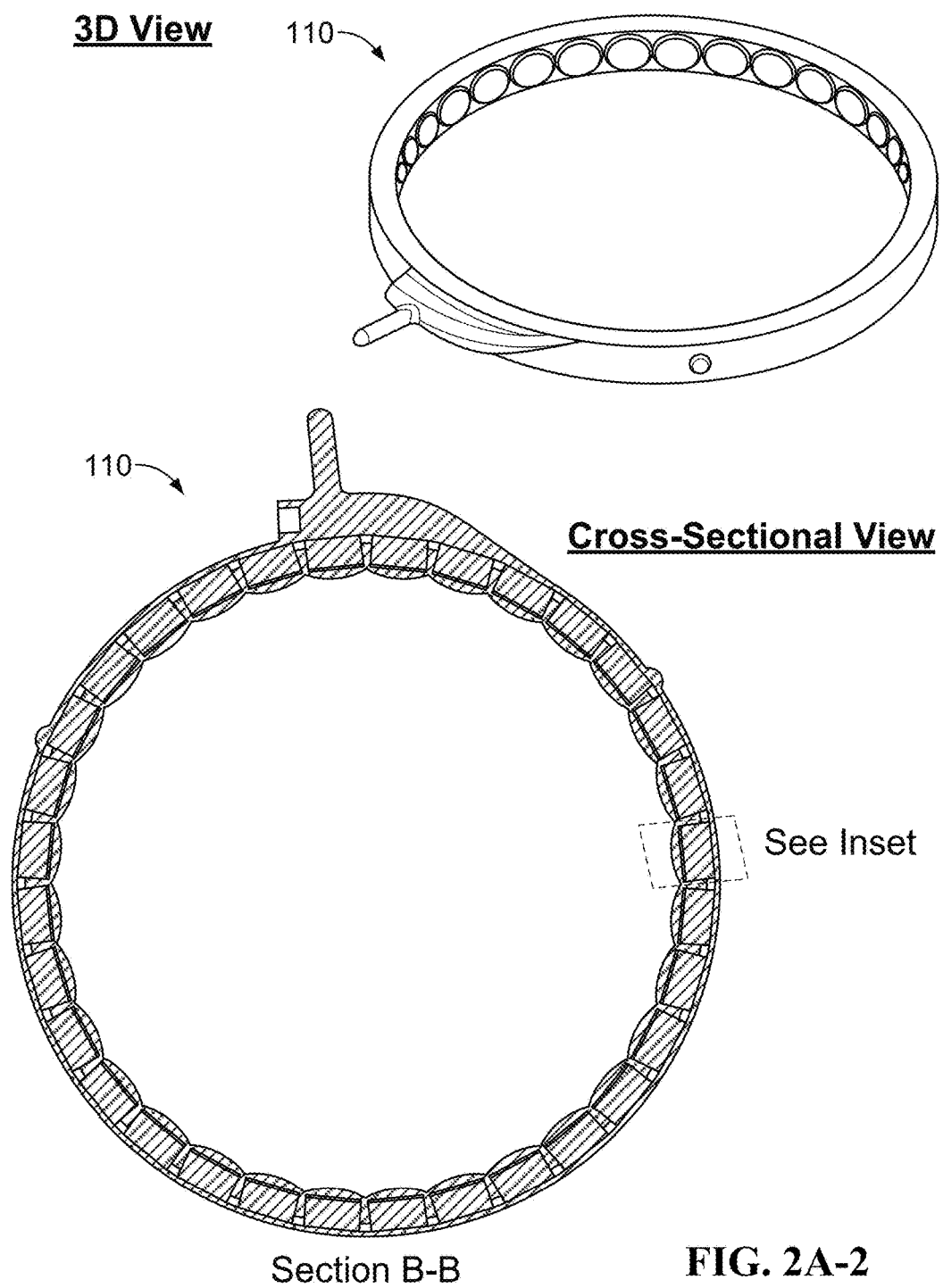

FIG. 2A shows a schematic of an exemplary acoustic transducer array structure 110, showing top, side and cross-sectional views of the structure. The acoustic transducer array structure 110 includes an array of transducer elements and a housing body 119 to contain and position the transducer elements 111 for transmitting and receiving acoustic signals to/from a mass to which the acoustic transducer array structure 110 is applied. The housing body 119 includes a curved section where the transducer elements 111 of the acoustic transmit and/or receive transducer array are positioned, where the curved section of the housing body 119 can be configured to various sizes and/or curvatures tailored to a particular body region or part where the structure 110 is to be applied in acoustic imaging, measurement, or other implementations. For example, the length, depth, and arc of the curved housing body 119 can be configured to make complete contact with a region of interest on an anatomical structure, e.g., such as a breast, arm, leg, neck, throat, knee joint, hip joint, ankle, waist, shoulder, or other anatomical structure of a human or animal (e.g., canine) subject to image or apply ultrasonic treatment to target volumes within such structures, such as splenic masses, cancerous or non-cancerous tumors, legions, sprains, tears, bone outlines and other signs of damage or maladies.

Figure 2B:
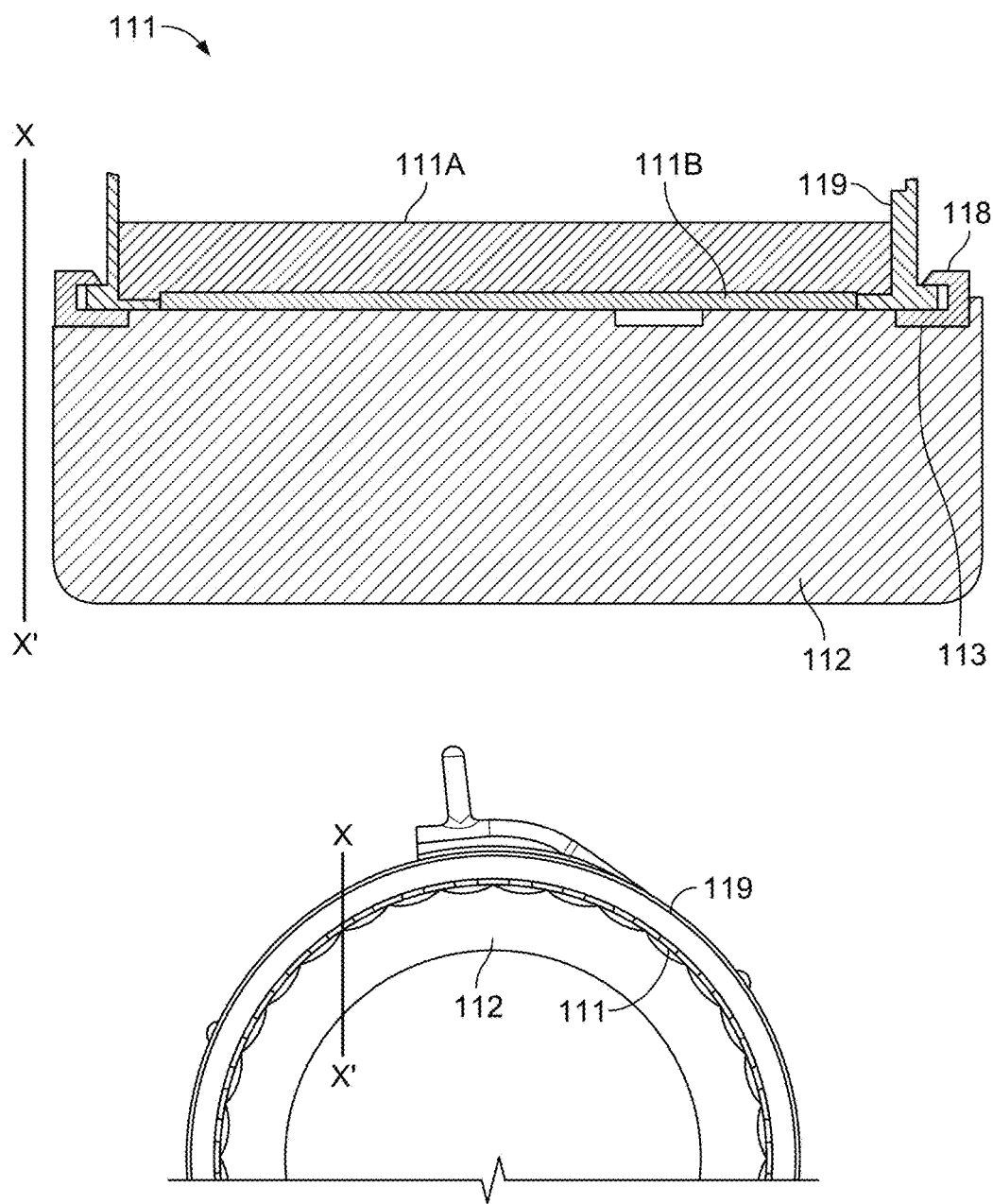
FIG. 2B shows a diagram of the exemplary acoustic transducer array structure, including an acoustic coupler to interface with a receiving body for acoustic signal transmission and reception.

FIG. 2B shows a diagram of the acoustic transducer array structure 110 coupled to the acoustic coupler 112 to interface with a receiving body for acoustic signal transmission and reception. The acoustic coupler 112 is coupled to the transducer elements 111 of the acoustic transducer array structure 110 creating an acoustic signal transmission interface between the structure 110 and the receiving body (e.g., subject's body part). The transducer elements 111 are attached to the housing body 119 via a flexible bracket 118. The acoustic coupler 112 is able to conform directly onto the face of the transducer element 111, as illustrated in the diagram. In this example, the acoustic coupler 112 is attached to clip components of the flexible bracket 118 by an adhesive 113 on the external surface of the clips, e.g., to align in contact with the 'tacky regions' of the hydrogel and/or outer lining of the acoustic coupler 112. The clips are configured to attach around the lip of the housing body 119 to provide direct contact between the acoustic coupler 112 and the face 111B of the transducer element 111. The transducer element 111 can include a transducer acoustic backing portion 111A that interfaces with electrical communication elements for transduction of electrical to/from acoustic energy.

Figure 3A:
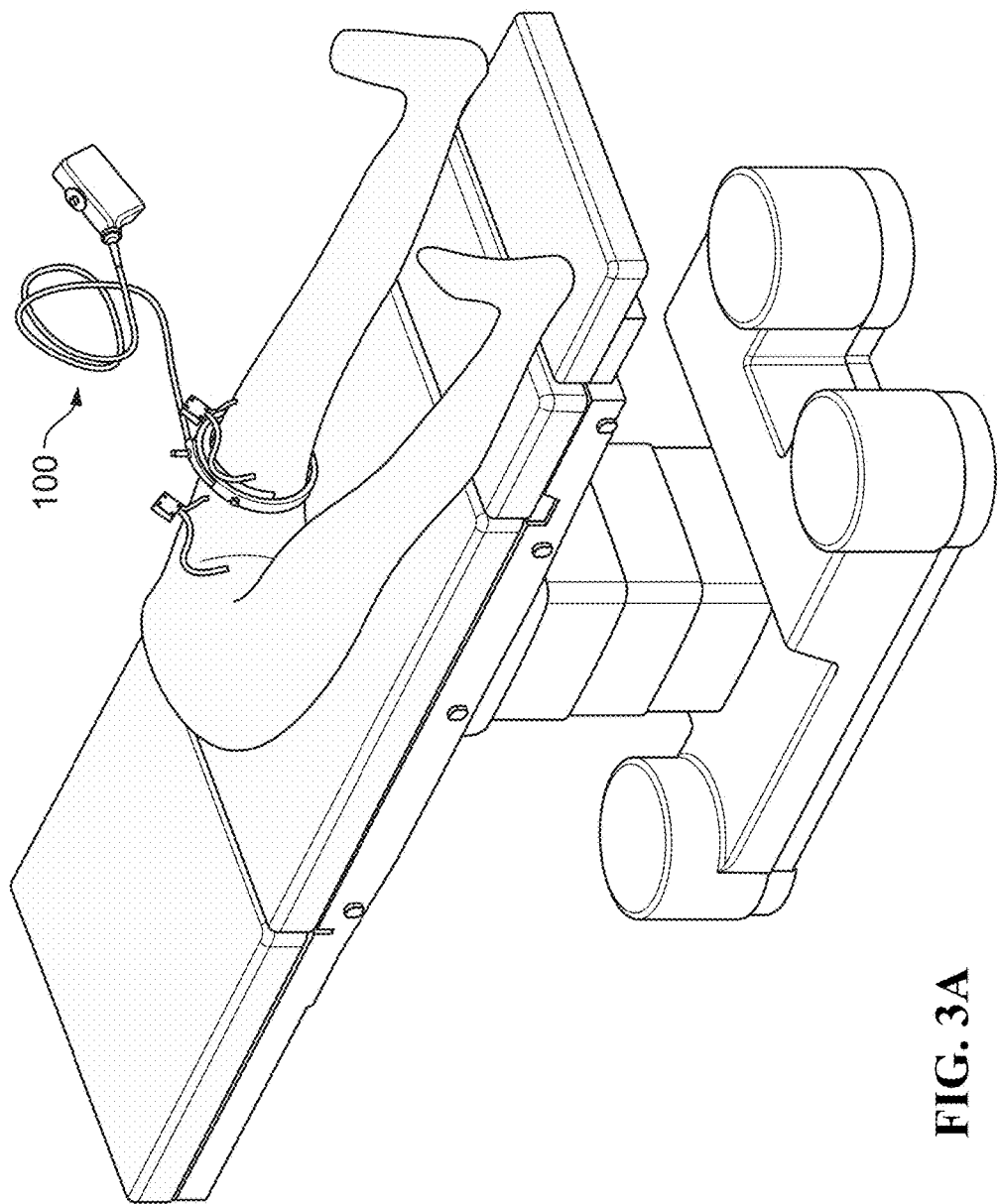
FIG. 3A shows various three dimensional views of the acoustic OTS 100 attached to the femur of a subject.
Figure 3C:
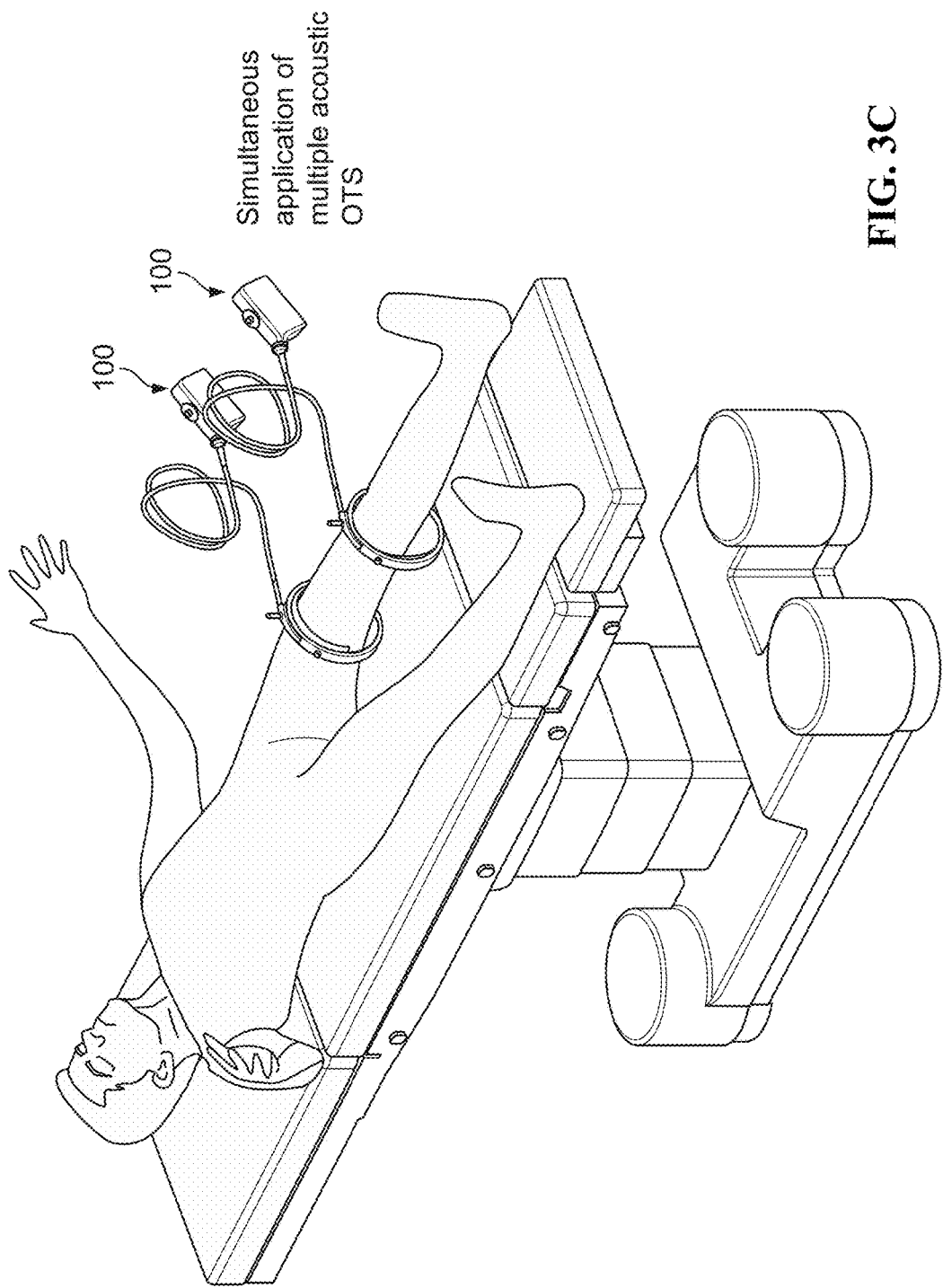
FIG. 3C shows a three-dimensional view of a portion of the disclosed system employing two arrays of transducers per leg.
Figure 3D:
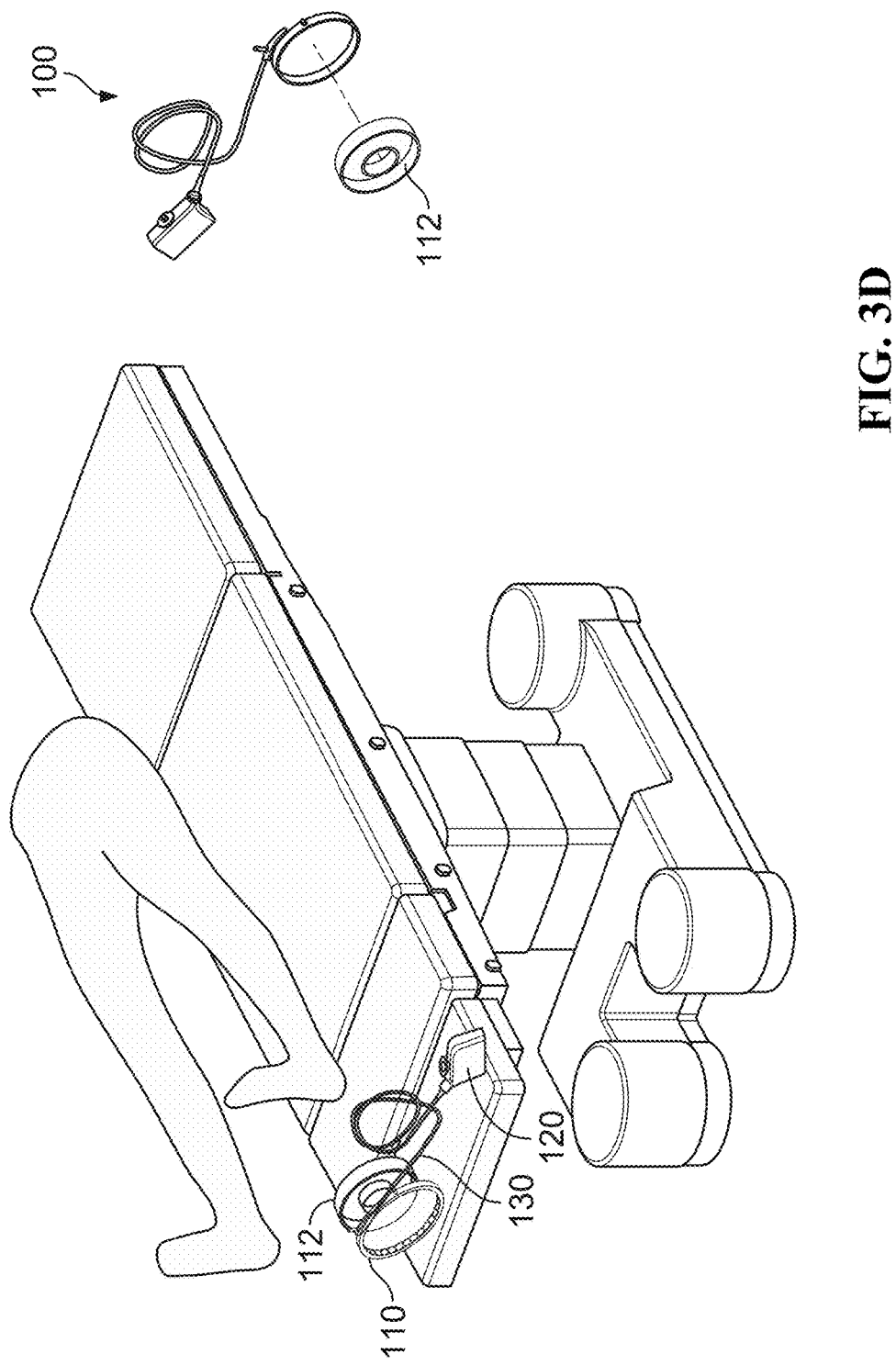
FIG. 3D is a three-dimensional view of a break-out diagram depicting the example acoustic OTS 100 and the acoustic coupler 112 with respect to the subject.

FIGS. 3A-3D show diagrams illustrating the exemplary acoustic OTS or multiple acoustic OTSes donned around a patient's leg to determine the topography of the bone, orientation of the bone in space, or other anatomical parameters of the patient's leg extremity. FIGS. 3A and 3B show various three dimensional views of the acoustic OTS 100 attached to the femur of a subject, which could be during a diagnostic and/or therapeutic procedure. FIG. 3C shows 3D view of a portion of the disclosed system employing two arrays of transducers per leg, including attaching two acoustic transducer array structures 110 on the leg: one for tracking the tibia and one for tracking the femur. FIG. 3D shows a 3D view of a break-out diagram depicting the example acoustic OTS 100 and the acoustic coupler 112 with respect to the subject.

Example features of the disclosed system, including the acoustic transducer array structure 110, the signal generator and processing device 140, and/or the position tracking device 146, are further described for various embodiments and implementations of the present technology.

The acoustic transducer array structure 110 includes ultrasound transducers that are affixed to a frame or housing body 119 (shown in FIG. 2B, for example), and is configured to fully or partially surround a body part containing one or more bones. The structure 110 can be configured to be curved or approximately curved, for example, as in the shape of a circle or ellipsoid. The curved structure may be open, for example, to cover 120 or 270 degrees around the body part. The opening may provide utility for accessing specific regions of the body, for example, for accessing a hip bone. In some embodiments, for example, the structure 110 is circular and covers 360 degrees around the bone. The structure 110 may be flexible, semi-flexible or rigid.

In a flexible embodiment, the structure 110 conforms arbitrarily to the body part, for example, like a sleeve. Transducers attached to a flexible material enable this embodiment. The flexible materials may include, but are not limited to rubbers such as, latex rubber, nitrile rubber, neoprene rubber, silicone rubber, and combinations thereof. Flexible materials may also include polymers, plastics, and resins. Flexible circuits and flexible coaxial cables enable flexible electrical connections to the transducers.

In a semi-flexible embodiment, for example, the structure 110 may contain hinges or pivot points between rigid sections that contain transducers, similar to chain links in a chain. The degrees of freedom provided by the semi-flexible design allow the structure 110 to conform to a variety of shapes. Position encoders located on each pivot point enable measurement of relative or absolute angle between adjacent sections. It is noted that 6 DoF refers to a Cartesian coordinate system with three dimensional spatial coordinates according to 3 orthogonal axes, e.g., commonly referred to x, y, and z axes, plus a rotation angle about each respective axis, commonly referred to as roll, pitch, and yaw, respectively.

In a rigid embodiment, for example, the structure 110 may be a fixed shape, such as a circular or elliptical ring or an approximately circular or elliptical polygon. The rigid embodiment of the structure 110 is structurally inflexible in all dimensions.

In some embodiments, for example, the structure 110 supports ultrasound transducers such that the 6 DoF position of all transducers are either a known, measured, or calibrated quantity relative to one or more designated points on the support structure. In other embodiments, for example, the 6 DoF location of each transducer is measured dynamically with respect to one or more external spatial reference points.

Particularly in the flexible embodiment, but notwithstanding the rigid and semi-rigid embodiments, the distance from an external reference point to points on the transducers 111 or the housing body 119 of the structure 110 can be measured dynamically, for example, using one or more, but not limited to, optical imaging cameras (e.g., CCD), optical sensors (e.g., photodiodes), optical patterns (e.g., QR codes), light emitting diodes, fiber optics, quantum dots, florescent particles, magnetic sensors (e.g., magnetometers, Hall effect sensors, MEMS-based magnetic sensors, etc.), magnetic particles, magnets, electromagnets, magnetic nanoparticles, gold nanoparticles, MEMS sensors, capacitive sensors, electromagnetic sensors, microwave sensors, and combinations thereof. For such measurements, distances are measured to the structure from one or more common spatial reference points with known 6 DoF coordinates. The 6 DoF coordinates corresponding to each measurement point on the structure are triangulated from three or more distance measurements. For example, measurement uncertainties for each transducer or structure are approximately reduced in proportion to the square root of the total number independent measurements made per transducer or structure, if for example, each transducer has multiple sensors or measurement points in order to enable triangulation of the 6 DoF coordinates. Coordinate transformations from one or more spatial reference points to one or more measurement points on the structure to each individual transducer are computed in real-time and stored for determining the position of the bone relative to one or more spatial reference points. The order of the coordinate transformations may follow several methods or formalisms to reach the same result, e.g., using direction cosines, Euler angles, or quaternions.

The shape of the structure 110 may be optimized to accommodate specific body parts. The structure 110 may embody ergonomic shapes and sizes specific to various populations, e.g., females or males. In some embodiments, for example, the body part slips through the inner diameter region of the structure 110 up to the point where the bone will be tracked. For example, an acoustic transducer array structure to measure the tibia slips over the foot, ankle, past the calf muscle to a region approximately 3-6 inches below the knee joint. The structure may be sized to accommodate specific size ranges of certain body parts, for example (e.g., calf muscles ranging from 6 to 10 inches in diameter).

The structure 110 may be fabricated from a variety of materials, e.g., including but not limited to combinations or composites of aluminum, titanium, stainless steel, polymers, fiberglass, plastics, rubbers, glass, or resins.

The structure 110 is designed to move with the body part as the body part is moved. For example, when the structure 110 is positioned around the thigh and hamstring region containing a femur bone, and as the leg is manipulated, the structure 110 is able to move with the leg such that angular excursions will not cause a detrimental effect on the acoustic data acquisition. For example, the structure 110 can be configured to be of lightweight in order to minimize mechanical momentum as the body part containing the bone is moved.

The structure 110 has freedom of motion with respect to the bone contained within the body part. The range of motion of the structure 110 with respect to the bone may be limited by the method of attachment of the structure 110 to the body part. For example, if the structure 110 is taped to the body part, the structure 110 approximately follows the body part as it is moved, but the flexibility in the tape and flexibility of the skin and underlying soft tissue allows for motion of the structure 110, although limited motion. In some embodiments, for example, the structure 110 is designed to have at least a limited freedom of motion with respect to the bone (contained within the body part), but the structure 110 is not rigidly coupled to the motion of the body part or bone contained within the body part. In operations, for example, the time dependent 6 DoF coordinates of the bone can be estimated relative to the structure 110, and the 6 DoF coordinates of the structure 110 transform the 6 DoF coordinates of the bone to a fixed point in space at each instant in time. Such operations can be implemented, which are in contrast to obtaining through static or time-independent transformations applied to the time dependent 6 DoF coordinates of the structure 110. Also, for example, the motion of the structure 110 relative to the bone can be operated such that such motions are limited, e.g., to prevent the structure 110 from detaching from of the body part. The structure 110 may be attached to a body part in a specific region where the bone contains features that are more easily tracked compared to another region.

The non-rigid coupling of the structure 110 relative to the bone has advantages over other means of rigid coupling. Most importantly, for example, the coupling is non-invasive. Also, for example, the non-rigid coupling of the structure 110 does not require methods associated with surgery, such as incisions, drilling, injections, metal screws, metal rods, temporary implants, permanent implants, and sutures. Non-rigid coupling of the structure 110 also protects the body from damage, e.g., such as bruising, infections, bleeding, blood clots, contusions, and scar tissue. The non-rigid coupling of the structure 110 is also naturally ergonomic and is configured to automatically find the lowest mechanical stress to both the structure 110 and the body part to which it is to be attached, where a mechanical system referred to here includes the structure 110, the acoustic coupler 112, the body part, the bone, and the component of the structure 110 used to affix the structure 110 to the body part and allow limited movement. For example, coupling acoustic energy from the structure 110 into an irregularly-shaped body part uses an acoustic coupling material, for example, such as a hydrogel that is flexible, elastic, and deformable.

In some embodiments, for example, the structure 110 may be cylindrical, with a variable or fixed height so as to accommodate different body parts and for affixing the structure 110 containing the transducer to the body part. The structure 110 may be temporarily affixed to the body part. For example, the acoustic transducer array structure 110 can include a securement component to affix the structure 110 to the body part, in which the securement component can include, but is not limited to, tape, adhesives, straps, buckles, snaps, buttons, Velcro, and cuffs, and combinations thereof.

Flexible cylindrical extensions from a circular ring structure, e.g., rubber cuffs, may be used to hold the structure 110 to the body part. The inner diameter of the cuffs may be slightly smaller than the circumference of the body part so as to slip over the body part and hold it firmly around the entire circumference. The rubber cuff may form a seal around the entire body part so that the void between the patient and the structure containing the transducers may be filled with a liquid or semi-liquid acoustic coupling medium. The cuff may be made from pure or composite elastic materials, including, but not limited to rubber elastomers, silicone, polyurethane, latex, neoprene, natural rubber, fabrics, nylon, silk, or cotton. Said cuff may be autoclavable for reuse or disposable for one use only. Materials compatible with autoclaving and chemical sterilization are well known in the field of medical devices.

An acoustic coupling medium is necessary to couple acoustic energy through the skin and soft tissue between the transducers and the bone. The acoustic coupling medium 112 of the disclosed technology may include several materials, e.g., including but not limited to water, polymers, organic solvents, organic chemical compounds, inorganic chemical compounds, and combinations thereof. The acoustic coupling medium 112 may specifically contain water, acrylamide, bisacrylamide, PVA, PVP, DMSO, propylene glycol, sodium benzoate, sodium alginate, sodium borate, sodium chloride, ammonia persulfate, calcium sulfate, magnesium sulfate, tetramethylethylenediamine (TMED), chitosan, acetic acid, ethanol, polyethylene glycol, sorbitol, dextrose, and aloe vera, and combinations thereof. The acoustic coupling medium 112 may contain organic or inorganic chemical compounds or particles to render it bacteriostatic.

The acoustic coupling medium 112 may be liquid or a gel with a sound speed and acoustic impedance similar to that of soft tissue. In some embodiments, for example, the sound speed provided by the acoustic coupling medium 112 ranges from 1450 to 1590 m/s to accommodate soft tissues, e.g., ranging from fat to muscle, respectively. In some embodiments, for example, the acoustic impedance ranges from 1.3 to 1.7 MRayl (kg/(sec·m$^2$)×10$^6$) to accommodate soft tissues ranging from fat to muscle, respectively.

The acoustic coupling medium 112 may include a preformed gel material, for example, a cylinder of hydrogel. In some embodiments, for example, the hydrogel may primarily include PVA and water subjected to several freeze thaw temperature cycles in order to crosslink the polymer and form a gel.

Prior to temperature cycling, the PVA solution is poured into a mold. As the mold is customizable using 3D printing technology, the shape of the exemplary hydrogel acoustic coupling medium 112 may be tailored to individual body parts and specific transducer structures. For example, the tibia presents a variable thickness of soft tissue around the leg where the tissue is thin at the shin and thick at the calf. A variable-thickness cylindrical hydrogel pad may be formed to provide a variable standoff path around the tibia so as to be thick at the shin and thin at the calf in order to place the acoustic focal region at the bone surface. Three-dimensional tomographic imaging information may be utilized to ergonomically tailor a gel pad to each patient.

In some embodiments, for example, the hydrogel adheres to the skin such that it may be removed with force, but not enough force to injure the skin or cause discomfort. The hydrogel has sufficient water and ionic content to keep the skin hydrated and flexible for long periods of time so as to minimize discomfort and acoustic artifacts at the gel-skin interface. The hydrogel has a groove or slot that accepts the ultrasound transducers and supporting structure with acoustic gel applied to the transducers. The structure is affixed to the body part by aforementioned temporary securement component.

Additional information and examples pertaining to the acoustic transducer array and structure device and acoustic signal transmission couplant devices of the present technology are described in the U.S. Patent Application Publication No. 2016/0242736, which is incorporated by reference in this patent document.

In some embodiments, for example, the acoustic transducer array structure is an integrated device including ultrasound transducers and a rigid supporting structure or frame and is enclosed in a casing portion that protects the electronics and transducer elements from mechanical damage. An acoustically compatible polyurethane or similar material may be employed as the outermost coating and to seal the enclosure up to where the cabling enters the device. The thickness, acoustic impedance, attenuation, and sound speed of the polyurethane coating on the transducers is controlled to optimize sound transmission as part of one or more acoustic matching layers present on each transducer. The connector 120 (e.g., cabling) can be configured to be strain relieved and captured into the device with one or more seals to prevent contaminants from intruding. The entire acoustic transducer array 110 up to the cabling may be autoclaved or chemically sterilized to allow for its reuse on multiple patients. Materials compatible with autoclaving and chemical sterilization are well known in the field of medical devices.

The transducers 111 convert electrical energy to acoustic pressure waves and acoustic pressure waves into electrical energy. Several piezoelectric materials may be used in the transducers 111, and are efficient electroacoustic transducers, e.g., including, but not limited to lead zirconate titanate (PZT), lead zinc niobate and lead titanate (PZN-PT), lead magnesium niobate and lead titanate (PMN-PT), lithium niobate, barium titanate, and lead metaniobate. The polymer polyvinylidene fluoride (PVDF) is also known to have good electroacoustic transduction properties. Some piezoelectric materials are formed as ceramics with a prescribed grain size, e.g., containing small crystals of the specific materials (e.g., PZT) that are sintered together. Other piezoelectric materials are formed from a single crystal of a piezoelectric material (e.g., PZN-PT, PMN-PT, etc.). To optimize acoustic properties, the transducers may be formed from one or more composites of the aforementioned materials combined with materials known to absorb or dampen acoustic energy (e.g., polyurethane, epoxy, etc.). Such composites may be formed by dicing and sub-dicing the transducers elements with cuts of various widths, lengths, and depths, which are filled with one or more attenuating materials, in order to isolate and/or attenuate specific vibrational modes. Transducers may be fabricated in multiple layers or stacks in order to increase bandwidth and efficiency.

In some embodiments, for example, each transducer 111 includes a circular element with a resonant frequency ranging from 1 to 10 MHz, and a −6 dB, half-amplitude fractional bandwidth ranging from 10 to 120% of the resonant frequency. In this example, the circular elements have a fixed focal depth and produce an acoustic beam with radial symmetry about the central axis perpendicular to the plane of the circular element. The circular elements have a preferred combination of center frequency of transmission, element diameter, and geometric focal depth, such that the range over which the acoustic field is focused, also known as the depth-of-focus or depth-of-field, includes the tissue-bone interface. The focal depth, also known as the Fresnel distance, and depth-of-focus also limit the center frequency and bandwidth due to expected frequency and depth-dependent attenuation, which may range from about 0.2 to over 1 dB/cm/MHz. For example, a bone located in shallow tissue is ideally located using a high center frequency such as 8 MHz, compared to a bone located deeply in tissue, which may be ideally located using a 2 MHz center frequency. Preferably, the attenuation at the maximum expected depth of the bone is not greater than 60 dB so as to accommodate a reasonable receiver gain. The circular elements are preferably matched to the impedance of the acoustic coupling medium 112 with one or more matching layers in order to maximize power transmission. Furthermore, the circular elements may be geometrically focused by either forming them into a concave shape or with the addition of a lens with a sound speed less than or greater than the acoustic coupling medium 112. For the purpose of maximizing the contact of the lens with the acoustic coupling medium, it is preferable to form the lens as a convex lens with sound speed less than the acoustic coupling medium such that the convex shape will make better contact with the acoustic coupling medium with less possibility of trapping air bubbles. For example, the purpose of lowering the side lobes of the spatial response of the circular element to below the standard first side lobe level of −17.5 dB, it is preferable, but not necessary, to include an apodization property to the acoustic lens or within one or more matching layers so as to reduce the side lobe level. The apodization is accomplished by including a material that has a variable attenuation as function of radius across the circular area of the transducer. Variable attenuation is accomplished by incorporating acoustic absorbing material with varying amounts as a function of radius. Such materials include, but are not limited to, micron-sized air bubbles, micron-sized microballoons of air, micron-sized particles of, but not limited to, rubber, plastic, glass, metal, and ceramic.

In some embodiments, for example, the number of circular transducer elements arranged on a circular ring structure is at least 16 (e.g., and in some embodiments, 32 or greater), as the standard error in determining the position of the bone is proportional to the square root of the number of independent measurements—thus 0.25 times the standard error for 16 elements and 0.125 times the standard error for 64 elements. The number of elements is largely dictated by the element diameters, as dictated by several relevant design parameters as discussed previously, and the circumference of the inner lumen of the ring. Using equations for circular ultrasonic transducer design, trade studies can be formulated to explore element diameters and center frequencies that can be used for a particular set of constraints. For example, to achieve a Fresnel distance ranging from 4 to 6 cm, a depth-of-field calculated as $\frac{2}{3}^{rds}$ the Fresnel distance ranging from 5.3 cm to 8 cm, and a two-way attenuation of less than 40 dB, assuming two-way attenuation of 1.0 dB/cm/MHz, the approximate element diameters and center frequency combinations that satisfy the aforementioned design constraints include, but are not limited to, 6 mm diameter at 8 MHz, 6-7 mm diameter at 7 MHz, 7 mm diameter at 6 MHz, 5 mm diameter at 5 MHz, 8-9 mm diameter at 4 MHz, 10-11 mm diameter at 3 MHz, 12-13 mm diameter at 2 MHz, 16-19 mm diameter at 1 MHz. FIG. 4 shows a diagram illustrating an example of the trade study.

As demonstrated in various example implementations of the present technology, several possibilities exist for element diameter and center frequency. The goal of the bone tracking approach is to maximize the potential for specular reflection from the bone and minimize the potential for Rayleigh scattering or Rayleigh-like scattering from within the bone itself. As the acoustic transmission coefficient for bone is greater than zero, and may be approximately 0.5, a substantial amount of acoustic energy enters the bone and can be scattered throughout the structure. As bone is a living tissue, albeit with much greater sound speed and acoustic impedance compared to soft tissue, scattering from within the bone is similar to Rayleigh scattering in soft tissue; however, bone has much greater frequency and depth-dependent attenuation ranging from 4-8 dB/cm/MHz. Thus, higher center frequencies are preferred to minimize the potential for Rayleigh scattering from within the bone.

Contrastingly, the potential for specular scattering is maximized for larger beam diameters, which cover a larger area over the bone surface, which increases the possibility of finding a flat or approximately flat region from which a specular reflection is received. The −6 dB beam diameter is approximately given by the f-number of the aperture times the wavelength, where f-number is approximately given by the Rayleigh distance or focal depth divided by the element diameter. For a constant focal depth of 5 cm, the aforementioned transducer diameter and center frequency combinations have beam widths ranging from approximately 4-4.7 mm for the 1 MHz designs to approximately 1.6 mm for the 8 MHz design.

For example, a trade exists for center frequency and element diameter versus specular scattering potential versus Rayleigh scattering potential. A preferable design based on aforementioned constraints would fall somewhere between the extremes, for example, a 5 mm diameter element at 5 MHz with a beam diameter of approximately 1.9 mm. In some cases, for example, it may be preferable to lean higher or lower in frequency. For example, in some cases, it may be preferable to have beams that approximately overlap at the surface of the bone, thus possibly requiring a lower frequency or smaller element to widen the beam.

The transducer elements 111 and configuration of the elements 111 are not limited to a single ring element placement within a single plane. For example, the elements may be placed along two or more rings such that the elements occupy two or more planes in a cylindrical arrangement, e.g., so as to track bone echoes along two or more planes along the length of a femur. The individual rings of elements occupying each plane may also be staggered with respect to the neighboring ring so as to distribute spatial samples more uniformly around the bone, for example, in a helical pattern or helical-like pattern such as a spiral. Likewise, the elements may be placed to achieve a periodic spatial sampling such that the angle between the elements is constant, for example, with 11.25 degrees separating 32 elements to span a full 360 degrees around the bone. Such a constant sampling arrangement would be applicable to tracking a femur bone, which is roughly circular. Applications where the optimal spatial sampling of the transducers is aperiodic or non-uniform or spatially diverse in three dimensions may be envisioned for tracking specific bones such as the hip bone, which does not conform to a circular geometry.

In some embodiments, for example, the transducer elements 111 are arranged in the same plane with each other such that all are pointing at the same point in space. In other embodiments, for example, the transducer elements 111 are fixed to point at angles determined to maximize specular reflections in the acoustic echoes from a particular bone. For example, the cross-section of the tibia is not round, but rather, approximately triangular. Transducer elements may be arranged to point along 3D vectors required to maximize the specular reflection from the surface of the tibia.

In some embodiments, for example, the location of the bone is maintained within the depth-of-focus with use of an acoustic coupling medium, e.g., a hydrogel. The elastic hydrogel coupling medium 112 may conform to irregularities in the body part and soft tissue surrounding the bone. The example hydrogel coupling medium 112 may be ergonomically designed and molded to fit a particular application.

Different transducer array configurations and geometries may be envisioned. Arrays may include hundreds or thousands of elements arranged in a circular or ellipsoidal or curved aperture that is either open or closed. For example, instead of using a single element to focus an acoustic beam, focusing may be achieved using suitably delayed transmissions from several small transducers elements arranged in one or more 1D, 1.25D, 1.5D, 1.75D, 2D, or 3D linear or phased arrays, as consistent with the current state-of-the-art in clinical ultrasound scanners. Linear arrays typically have a pitch or spacing between element centers of one wavelength or more, and phased arrays have a pitch of less than one wavelength, and preferably one-half wavelength or less to allow for steering the acoustic beam. The operating of linear or phased arrays can be either in full or partially synthetic aperture mode as commonly implemented in clinical ultrasound scanners. The disclosed system is not limited to a specific means or aperture dimension for transmitting or receiving acoustic energy. Moreover, the disclosed system is not limited to a particular diameter, shape, or size for the transducer array. The disclosed system is directly applicable to partially or fully beamformed ultrasound images from one or more aspects or views or angles or directions, tomographic ultrasound over angles ranging from 0 to 360 degrees, synthetic aperture ultrasound, and three dimensional ultrasounds data sets.

Specific embodiments utilizing an array or plurality of arrays of transducer elements apply specifically to high resolution and high speed orthopedic tracking with circumferential or tomographic coverage of a bone, e.g., a femur.

Figure 5A:
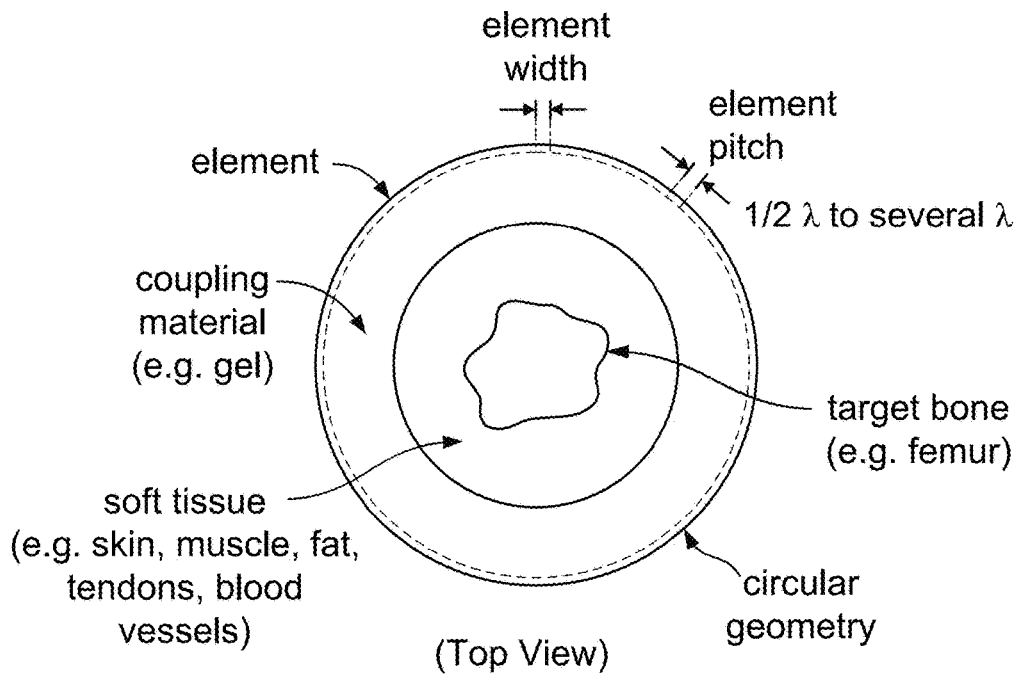
FIG. 5A shows a top view of an example tomographic array.

In one embodiment, a 1D array of transducer elements with pitch ranging from ½ wavelength to several wavelengths are arranged in a full circle to form a tomographic array. FIG. 5A shows a top view example of such a tomographic array. In this arrangement, depending on the electrical connectivity of the array with regards to both transmission and reception and the number of channels in each case, there are many possibilities for transmission and reception. Likewise, the target application of the array dictates the required spatial sampling around the circumference of the array. For example, in some cases it may be beneficial to utilize large elements with a narrow directivity so as to focus acoustic energy both on transmission and reception along specific directions or radial vectors defined by the vectors pointing from the center of the element to the geometric center of the circular array. In other cases, for example, it may be beneficial to utilize small elements with a wide directivity such that the array may operate with, for example, dynamic focusing and apodization on both transmission and reception.

Figure 5B:
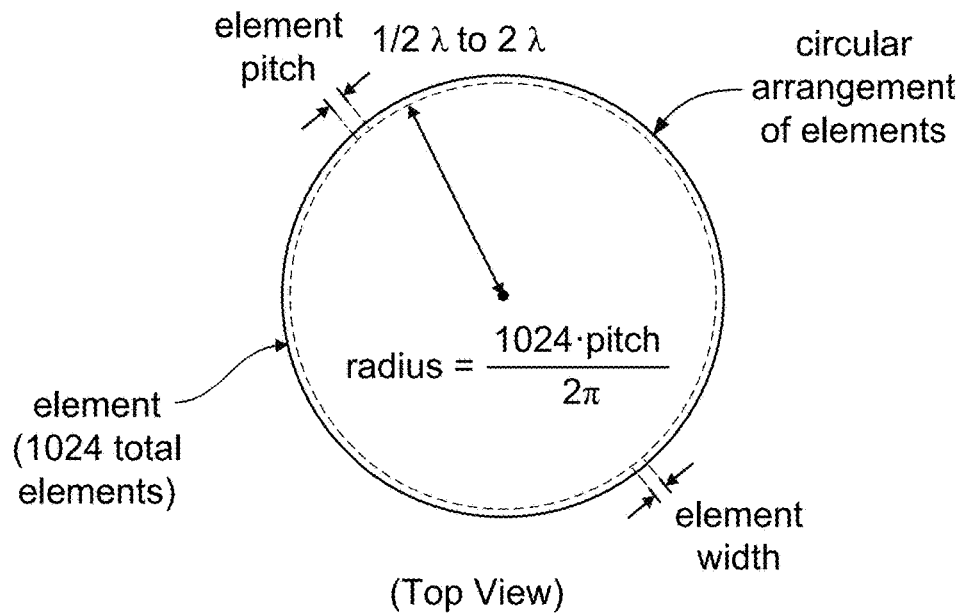
FIG. 5B shows a top view of an example tomographic array having specific parameters.
Figure 5C:
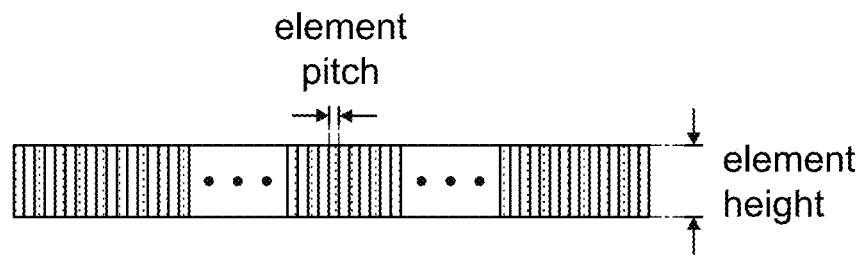
FIG. 5C shows a side view of the tomographic array of FIG. 5B.
Figure 5D:
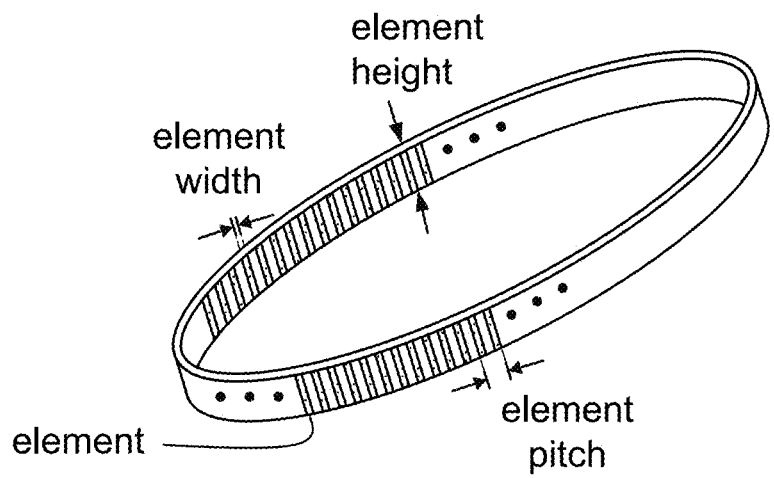
FIG. 5D shows an isometric view of the tomographic array of FIG. 5B.

Generally, the pitch or spacing of the elements must be limited in order to reduce or eliminate the potential for grating lobes on either transmission or reception in either real beam or synthetic aperture operation when steering is required in beam formation. Considering orthopedic tracking applications where steering is enabled, an example array can contain 1024 transducer elements arranged side-by-side with azimuthal pitch ranging from ½ wavelength to 2 wavelengths that comprise a tomographic aperture with radius equal to approximately 1024 times the element pitch divided by $2\pi$. FIG. 5B shows a top view examples of such an array, while FIGS. 5C and 5D show a side view and an isometric view of such an array. Accordingly, element widths range from ½ wavelength to 2 wavelengths minus the space between elements, i.e., the kerf. Element heights in the elevation dimension may span several wavelengths in order to provide both passive and geometric focusing ability in elevation, depending on the typical depth and depth-of-focus requirement for a particular application. The described tomographic aperture is provided for the purpose of illustrating specific transmission and reception patterns. The transmission and reception patterns are equally applicable to arrays that contain arbitrary element sizes and numbers of elements arranged in a tomographic configuration.

Figure 5E:
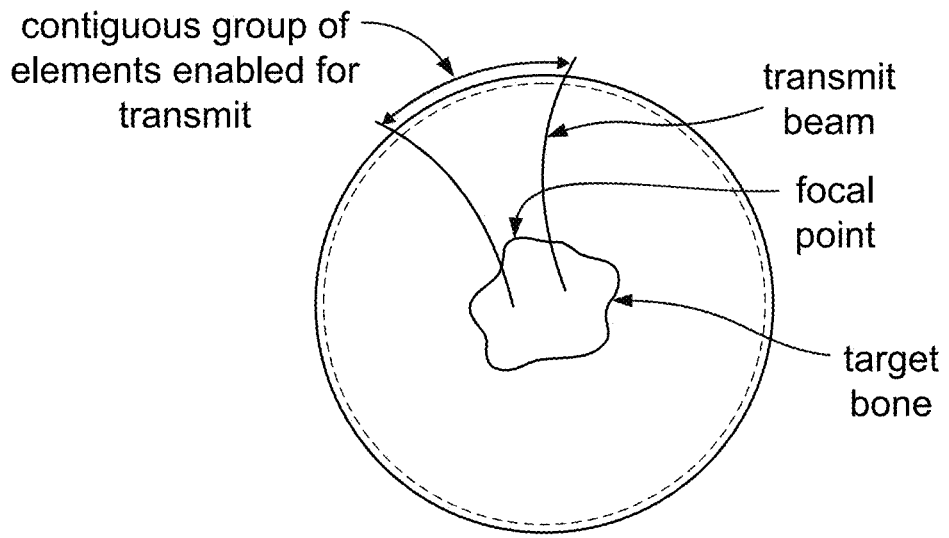
FIG. 5E shows an example tomographic array in which transmission is enabled on a contiguous group of elements.

In some embodiments, transmission is enabled on one or more transducer elements, preferably, in the case of more than one element, a contiguous group of elements, with electronic delays assigned to each to form a single focused acoustic beam, i.e., a real beam. FIG. 5E illustrates an example of such a configuration in which transmission is enabled on a contiguous group of elements. The case of transmission on one element is handled separately as further described below. The process of beam formation is well known in the art of ultrasound imaging, radar imaging, and signal processing.

Figure 5F:
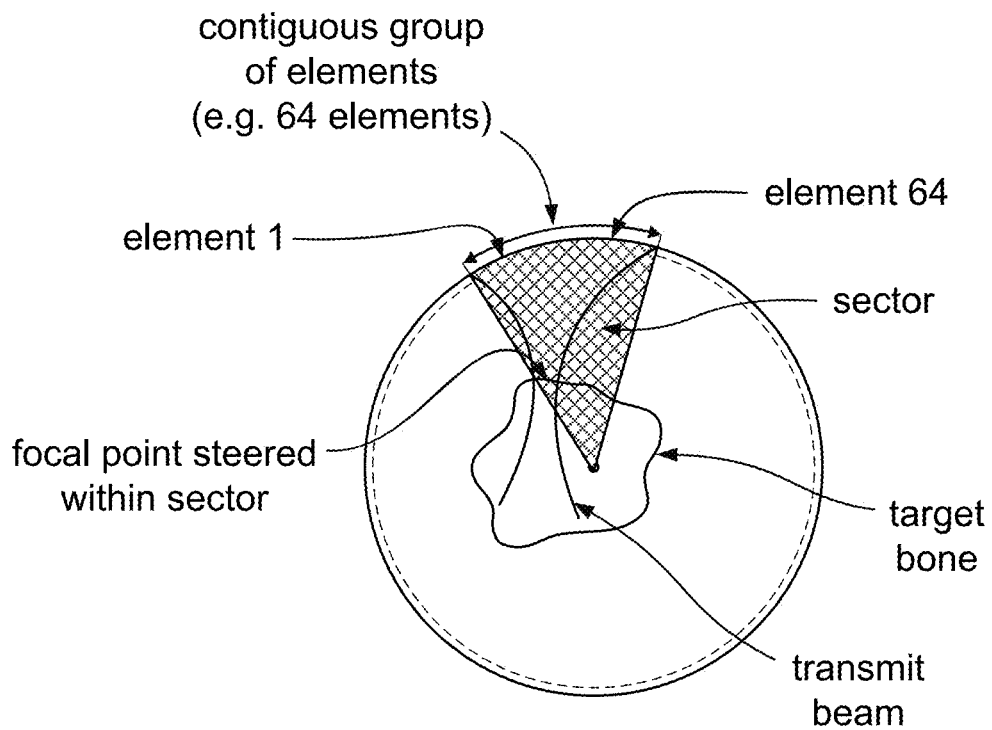
FIG. 5F shows an example tomographic array in which the focal point of the beam falls within the sector subtended by the arc length and angle spanned by contiguous array elements.
Figure 5G:
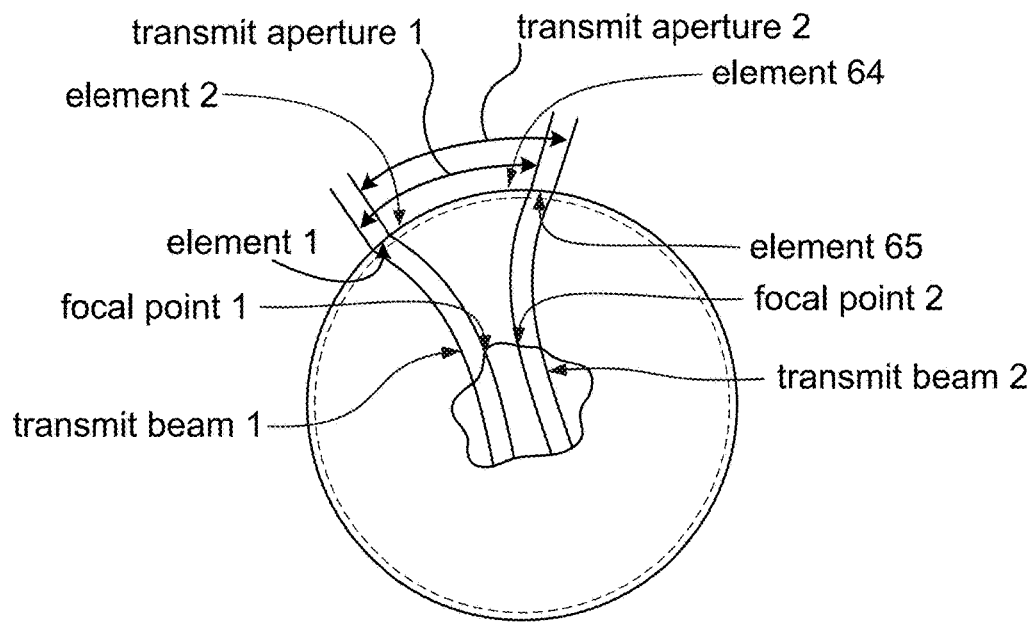
FIG. 5G shows a second beam transmission in the tomographic array of FIG. 5F.

In one example, the real transmit beam may result from transmission on 64 contiguous elements, e.g., elements 1 through 64, where the focal point of the beam falls somewhere within the sector subtended by the arc length and angle spanned by elements 1 through 64, as depicted in the exemplary diagram of FIG. 5F. In this example, transmission on elements 1 through 64 can be followed by transmission on elements 2 through 65, as shown in the exemplary diagram of FIG. 5G.

In some embodiments, the transmit beam may step arbitrary increments in element index, for example, transmission on elements 1 through 64 followed by transmission on elements 257 through 320.

In some embodiments, the real transmit beam may be steered arbitrarily in space by applying suitable delays to each participating transmit element.

In some embodiments, the real transmit beam may be arbitrarily fired from any contiguous group of elements with the virtual center of the transmit aperture, i.e., phase center, changing from one transmission to the next with spacing that changes in ways that include, but are not limited to, stationarily (e.g., 1 1 1 . . . ), incrementally (e.g., 1 2 3 . . . ), sequentially (e.g., 1 3 5 . . . ), periodically (e.g., 1 513 1 513 . . . ), randomly (e.g., 254 46 884 373 109 209 . . . ), repeatedly (e.g., 1 1 1 . . . ), cyclically (e.g., 1 2 3 1 2 3 . . . ), or deterministically (e.g., mod(transmit index, 128)=0).

In one embodiment, the real transmit beam is fired according to a sequence that repeats periodically with a defined cycle time.

Figure 5H:
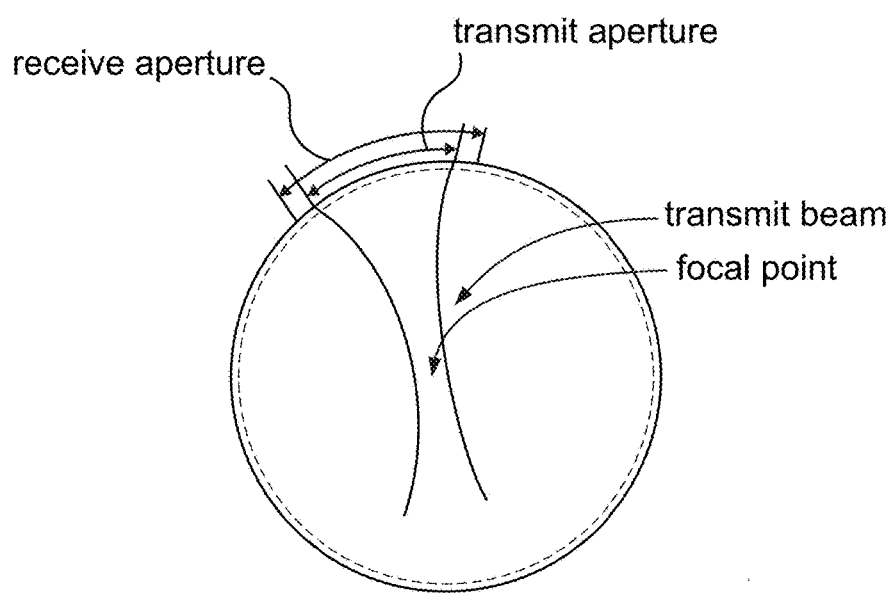
FIG. 5H shows an example configuration of a tomographic array in which receive aperture includes one or more elements centered or approximately centered with the transmit aperture.

Following transmission of the real beam, a plurality of elements comprising the receive aperture is enabled to receive acoustic echoes. In some embodiments, the receive aperture includes one or more elements centered or approximately centered with the transmit aperture, as depicted in FIG. 5H.

In some embodiments, the receive aperture follows the transmit aperture as it changes location between transmissions.

Parameters affecting the real beam, e.g., aperture size, apodization and delays, may be pre-determined according to a priori information, e.g., an MRI or CT image that gives measurements of distance from the expected location of the transducer elements to the surface of the bone. The a priori information may be used in determining the location of the beam relative to features on the bone, e.g., normal to a flat region or normal to the local apex of a curved region.

Additionally, an optimization process can determine the number of elements involved in a transmission, the transmission delays for each element, the transmission amplitudes for each element (e.g., a normalized per-element transmit apodization ranging from 0 to 1). In particular, the real beam may be manually or automatically tuned to place the focal point at the surface of a bone according to focusing metrics derived from coherently beamforming echoes received from the vicinity of the bone, e.g., echo intensity, echo power and image contrast in the vicinity of the bone. Likewise, transducer elements utilized for reception may also be optimized to determine the optimal number of elements involved in reception, the received delays for each element, and the weightings of each received echo (e.g., a normalized per-element receive apodization ranging from 0 to 1).

Figure 5I:
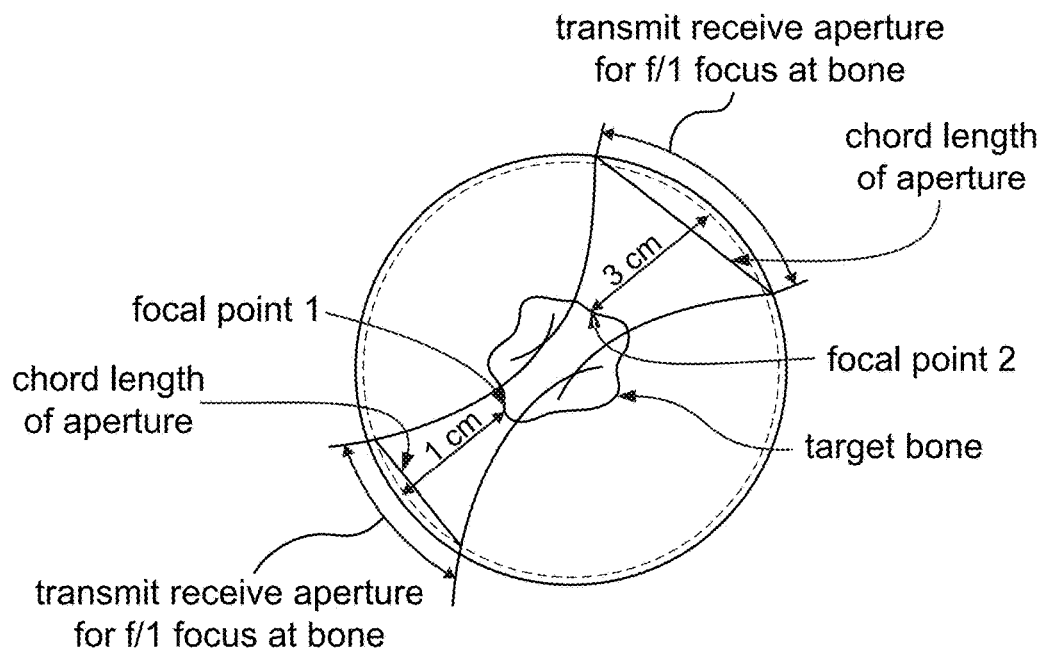
FIG. 5I shows an example configuration of a tomographic array in which f-number of 1 is maintained for two focal points.

In some embodiments, the f-number, e.g., the focal depth divided by the aperture size of the transmit and receive aperture is held approximately constant for each beam relative to the focal point aligned with the surface of the bone for a plurality of points insonified on the bone. For example, to maintain an f-number of 1 for two bone interfaces at 1 cm depth and 3 cm depth from points on the array, the aperture sizes must be approximately 1 cm and 3 cm, respectively. This can be seen with from the example diagram in FIG. 5I, where f-number of 1 is maintained for two focal points that are at 1 cm and 3 cm, respectively, from the transmit/receive apertures on two sides of the array. Here aperture size is defined by the linear distance measured to points on the most distant elements comprising the aperture, e.g., the chord length.

As an alternative to beamforming with real beams, synthetic aperture beamforming may be employed. In synthetic aperture embodiments, many possibilities exist for beam formation. For example, a synthetic transmit aperture may utilized with a non-synthetic receive aperture. Alternatively, a non-synthetic transmit aperture may be used with a synthetic receive aperture. In yet another alternative, a synthetic transmit aperture may be used with a synthetic receive aperture. In some applications, it may not be feasible to utilize a fully synthetic transmit and receive aperture due to the high number of transmit and receive combinations that need to be acquired independently.

The high degree of redundant echo information contained within full synthetic aperture beamformer samples combined with the limited directivity of transducer elements enables specific embodiments, some of which are further described below.

In one embodiment, transmission from the previously described example array is enabled on one transducer element at a time, e.g., in a synthetic transmit aperture format, followed by reception on one or more elements simultaneously that include the transmit element and elements to either side of the transmit element. This embodiment differs from the above described embodiment in that one transmit element is utilized instead of a group of transmit elements.

For example, transmission on element 1 is followed by reception on a contiguous group of 64 elements ranging from 993 to 32. Next, transmission on element 2 is followed by reception on 64 elements ranging from 994 to 33. Next, transmission on element 3 is followed by reception on 64 elements ranging from 995 to 34. This pattern is continued sequentially until all elements are used for transmission one time to complete a single cycle.

Without loss of generality, this embodiment also applies to smaller or larger receive apertures (e.g., 32 or 128 elements), where the transmit element is approximately centered within the receive aperture, and the receive aperture steps with the transmit element.

In another embodiment, a special case of synthetic aperture is implemented for transmission on one element and reception on the same element. This embodiment differs from the above described embodiment in that one transmit element is utilized instead of a group of transmit elements.

Referring to the previously described example array, for example, with a cycle starting with transmission on element 1 is followed by reception on element 1. Next, transmission on element 2 is followed by reception on element 2. Likewise, transmission on element 3 is followed by reception on element 3. The pattern ends with transmission on element 1024 and reception on element 1024 to complete one cycle, after which it is repeated.

In this embodiment, transmission and reception may proceed out of sequential order, for example, in sequential quadrants. Referring to the previously described example array, the cycle may start with transmission on element 1 followed by reception on element 1. Next, transmission on element 257 is followed by reception on element 257. Next, transmission on element 513 is followed by reception on elements 513. Next, transmission on element 769 is followed by reception on element 769. Next, transmission on element 2 is followed by reception on elements 2. Next, transmission on element 258 is followed by reception on elements 258. Next, transmission on element 514 is followed by reception on elements 514. Next, transmission on element 770 is followed by reception on elements 770. The pattern continues by increasing the element index for transmission and reception by one. The pattern ends with transmission on element 1024 followed by reception on element 1024. Each iteration is incremented by one element until all elements are used for transmission once to complete one cycle before it is repeated.

Similarly, transmission and reception may proceed out of sequential order in other divided manners, including, but not limited to sequentially in haves, quadrants and octants.

Alternatively, transmission may proceed according to a random or pseudorandom permutation of the elements, e.g., 328; 82; 119; 829; 130; 91; 848; 485; 4; 238 and so forth until all elements are used for transmission one time to complete a transmission cycle. For each transmission, reception occurs on the transmit element. For example, after transmission on element 328, a reception occurs on element 328.

An important feature of this embodiment is that only 1 transmit channel and 1 receiver channel is required per transmission event, thus dramatically reducing the hardware complexity and volume of data for this operating mode compared to full synthetic aperture modes that utilize many more elements on reception. A reduced data rate in turn reduces the time required to transfer echo samples and the time required to process the samples, and ultimately, reduces the time lag between the true physical location of a target, e.g., a bone, and the estimated location of the target. A high rate of position feedback with low lag is of critical importance in assisted surgery in order to prevent controller feedback errors due to inaccuracies, undersampling, and hysteresis.

In one embodiment, a second special case of synthetic aperture is implemented for transmission on one element and reception on two elements, specifically, reception on the transmit element and on one immediately adjacent element. For example, an array containing 1024 transducer elements arranged side-by-side with pitch ranging from ½ wavelength to 1 wavelength that comprise a tomographic aperture. In this configuration, transmission on element 1 is followed by reception on elements 1 and 2. Next, transmission on element 2 is followed by reception on elements 2 and 3. Likewise, transmission on element 3 is followed by reception on elements 3 and 4. The pattern ends with transmission on element 1024 and reception on elements 1024 and 1 to complete one cycle, after which it is repeated. Alternatively, the cycle may start with transmission one element 1 followed by reception on elements 1024 and 1. Next, transmission on element 2 followed by reception on elements 1 and 2, and so forth until ending with transmission on element 1024 and reception on elements 1023 and 1024. Reception on both elements preceding and following the transmission element is also possible and disclosed herein; however, the acoustic echo information is largely redundant for both cases.

In this embodiment, transmission and reception may proceed out of sequential order, for example, in sequential quadrants with transmission on element 1 followed by reception on elements 1 and 2. Next, transmission on element 257 is followed by reception on elements 257 and 258. Next, transmission on element 513 is followed by reception on elements 513 and 514. Next, transmission on element 769 is followed by reception on elements 769 and 770. Next, transmission on element 2 is followed by reception on elements 2 and 3. Next, transmission on element 258 is followed by reception on elements 258 and 259. Next, transmission on element 514 is followed by reception on elements 514 and 515. Next, transmission on element 770 is followed by reception on elements 770 and 771. Each iteration in incremented by one element until all elements are used for transmission once to complete one cycle before it is repeated.

Similarly, transmission and reception may proceed out of sequential order in other divided manners, including, but not limited sequentially in haves, quadrants and octants.

Alternatively, transmission may proceed according to a random or pseudorandom permutation of the elements, e.g., 72; 987; 63; 231; 546; 771; 9; 1021; 393; 20 and so forth until all elements are used for transmission one time to complete a transmission cycle. For each transmission, reception occurs on the transmit element, and on the preceding element or on the following element, e.g., for transmission on element 72, a reception occurs on elements 71 and 72 or on elements 72 and 73. Simultaneous reception on elements 71, 72 and 73 is also possible; however, the information contained in echoes recorded for elements 71 and 73 are largely redundant.

An important feature of this embodiment is that only 1 transmit channel and 2 receiver channels are required per transmission event, thus dramatically reducing the hardware complexity and volume of data required for this operating mode compared to full synthetic aperture modes that utilize many more elements on reception. A reduced data rate in turn reduces the time required to transfer echo samples and the time required to process the samples, and ultimately, reduces the time lag between the true physical location of a target, e.g., a bone, and the estimated location of the target. A high rate of position feedback with low lag is of critical importance in assisted surgery in order to prevent controller feedback errors due to inaccuracies, undersampling, and hysteresis.

Figure 5J:
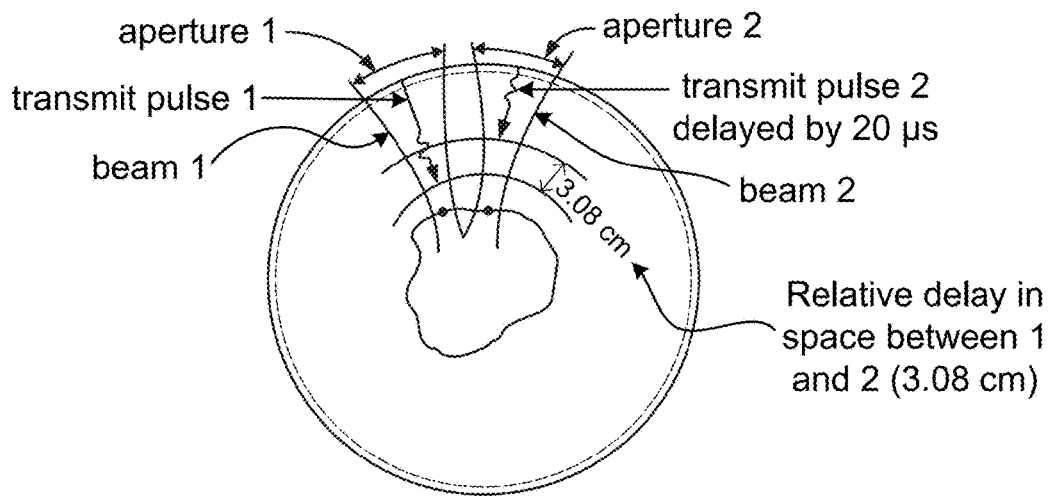
FIG. 5J shows an example configuration of a tomographic array in which multiple transmissions are staggered in time.
Figure 5K:
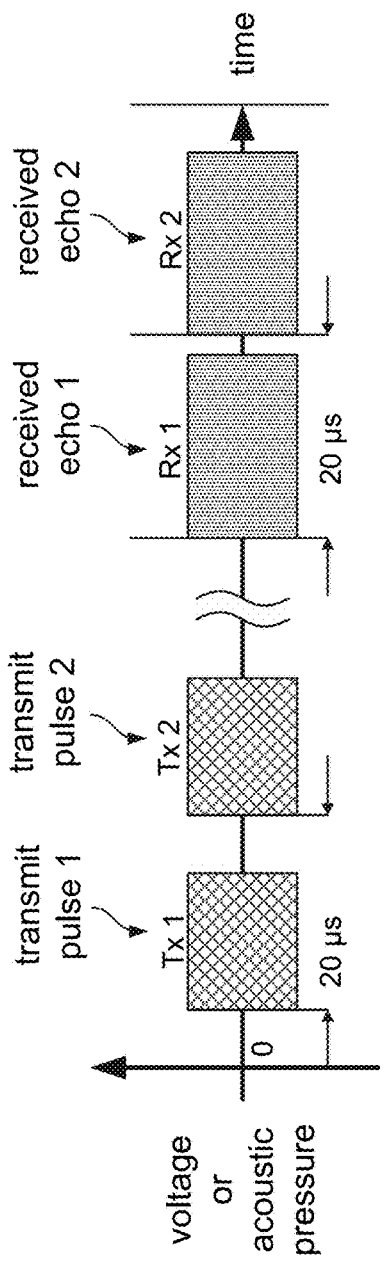
FIG. 5K shows an example sequence of transmit and receive signals as a function of time associated with the configuration in FIG. 5J.

In all real beam and synthetic aperture embodiments, it is only necessary to beamform echoes over a narrow range window that includes a bone interface. In this regard, multiple transmissions may be staggered in time in such a way that they are in flight at the same time, though spaced apart adequately to prevent overlapping echo samples in the beamformer, as illustrated in the example configuration of FIG. 5J. For example, a range window of 3 cm, is first insonified by a transmission on aperture 1 followed by a coherent transmission on aperture 2 after a prescribed delay, e.g., 20 microseconds or 3.08 cm in space at sound speed equal 1540 m/s, followed by reception on aperture 1, followed by reception on aperture 2. FIG. 5K illustrates an example sequence of transmit and receive signals as a function of time. A high speed multiplexer may be used to switch reception from apertures 1 and 2. Using this technique, the resulting cycle time required to cover all elements on transmission is divided by approximately a factor of 2. Likewise, additional reductions in cycle time are allowed for each additional staggered transmission. For example, 3 staggered transmissions reduces the cycle time by approximately a factor of 3. As an alternative to multiplexing, additional receive channels may be utilized.

The transmission delays utilized to stagger transmissions may be varied randomly in order to temporally decorrelate coherent echoes from previous transmissions, thus producing what is sometimes referred to as temporal dithering in fields such as ultrawideband communications.

In another embodiment, simultaneous transmissions are enabled using coded waveforms, specifically, waveforms that are orthogonal, e.g., their mutual cross correlations are zero or approximately zero for all delays.

In another embodiment, simultaneous transmissions are enabled using coded waveforms, specifically, waveforms that are partially orthogonal, e.g., their mutual cross correlations are zero or approximately zero for a range of delays.

Figure 5L:
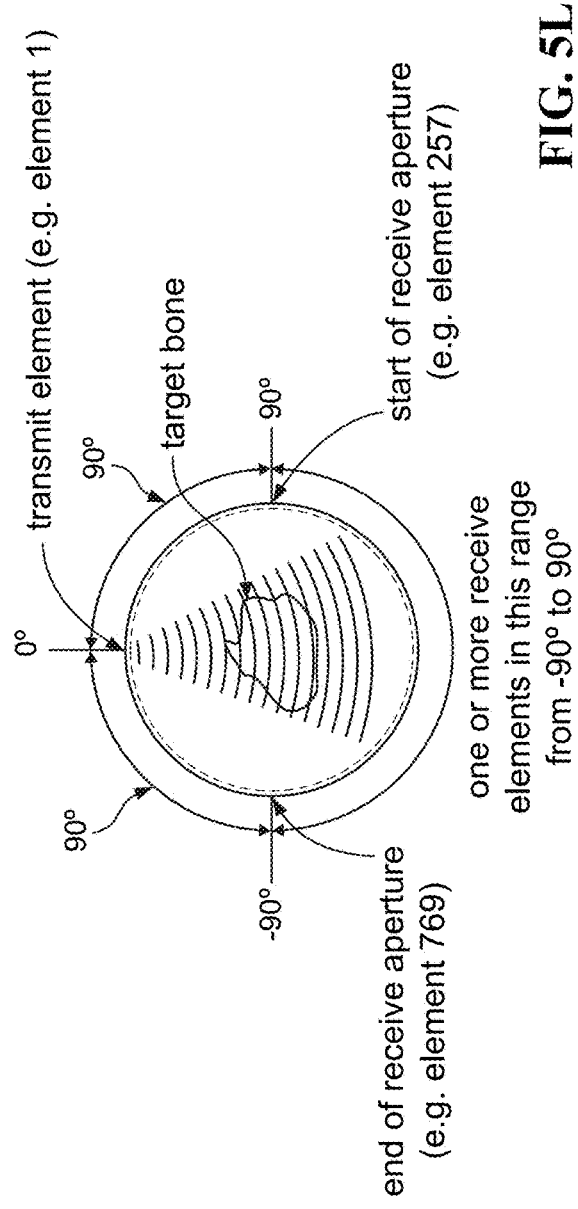
FIG. 5L shows an example configuration of a tomographic array in which one or more receptions occur on array elements that are between 90 degrees and −90 degrees away from the phase center of the transmitting aperture.

In another embodiment, one or more receptions occur on array elements that are between 90 degrees and −90 degrees away from the phase center of the transmitting aperture, e.g., in a pitch-catch transmit-receive fashion, for the purpose of measuring the time of flight and attenuation for a given propagation path. As illustrated in FIG. 5L, using the above described example array, for a transmission on element 1, there are one or more receptions on elements 257 through 769. A complete cycle of such transmissions and receptions comprises a transmission tomographic dataset from which sound speed and attenuation may be estimated and used for refining beamformer delays on both transmission and reception.

The disclosed technology includes methods for processing the data, e.g., using the data processing unit 144 (shown in FIG. 1C), to produce a data set identifying shape, location, and movement information of an orthopedic structure of a body part from which the acoustic signal data is acquired. Example features of the disclosed method are further described for various embodiments and implementations of the present technology.

The example methods for orthopedic tracking are described in general terms and are applicable to any possible array configuration of the acoustic OTS 100. Acoustic (e.g., ultrasound) pulses are transmitted from the plurality of acoustic transducer elements 111 of the structure 110, e.g., including sequentially one-at-a-time, simultaneously, or in a time-staggered or time-delayed pattern. Each transmission is accompanied by receptions of acoustic echoes on one or more of the transducer elements 111 corresponding to a single transmission. In the case of a circular fixed-focus piston transducer, for example, the echoes are received only on the same transducer. In the case of a linear or phased array, for example, reception occurs on one or more transducers simultaneously. The received echoes are amplified, filtered, and temporally sampled sufficiently, e.g., by the device 140, to retain all relevant spectral information corresponding to the echoes from soft tissue and bone as is dictated by the Nyquist sampling theorem. Received echoes are digitally sampled and stored for processing.

Preferably, the transmitted pulse contains the widest bandwidth possible, e.g., around 100% fractional bandwidth, which approximately corresponds to an impulse response of a single acoustic cycle. The reason for the high bandwidth being that the location of specular echoes from the bone will have a range uncertainly that is approximately inversely proportional to wavelength divided by fractional bandwidth. For example, an 80% fractional bandwidth system operating at 5 MHz has a wavelength of 0.308 mm. The range measurement uncertainty for this example pulse is approximately 0.308 mm divided by 0.8, which equals 0.385 mm. Other sources of measurement uncertainty may include, but are not limited to, spatial averaging caused by the finite beam size, electronic noise, temporal sampling, quantization noise, side lobes, grating lobes, attenuation, sound speed, and motion. Except in the case of very high velocities of motion of the array or patient, greater than 1 m/s, the bandwidth, wavelength, and sound speed are typically the largest sources of measurement uncertainty. Using transmitted waveforms with a large time-bandwidth (e.g., spread-spectrum waveforms) product enable deeper penetration at a higher transmitted frequency in order to compensate for loss in signal-to-noise ratio (SNR) due to frequency and depth-dependent attenuation.

In some embodiments, for example, the waveforms used belong to a class of waveforms known as spread-spectrum waveforms. Such waveforms are robust to deleterious factors including, but not limited to, frequency and depth-dependent attenuation, electronic noise, cross-talk between adjacent channels, and acoustic reverberation. For example, waveforms can be transmitted with a pulse-repetition-frequency (PRF) ranging arbitrarily up to about 100 kHz, with the upper end dictated by the sound speed, attenuation, the maximum depth from which the echoes contain useful information, degree of spatial and temporal overlap between neighboring transmitted beams (e.g., staggered transmissions), speed of transmit and receive multiplexer circuitry, electronic crosstalk, and potential tissue heating. The PRF and the number of transmissions per cycle to adequately insonify independent locations on the bone dictate the rate at which the OTS provides position feedback on the 6 DoF coordinates of the bone.

Figure 6A:
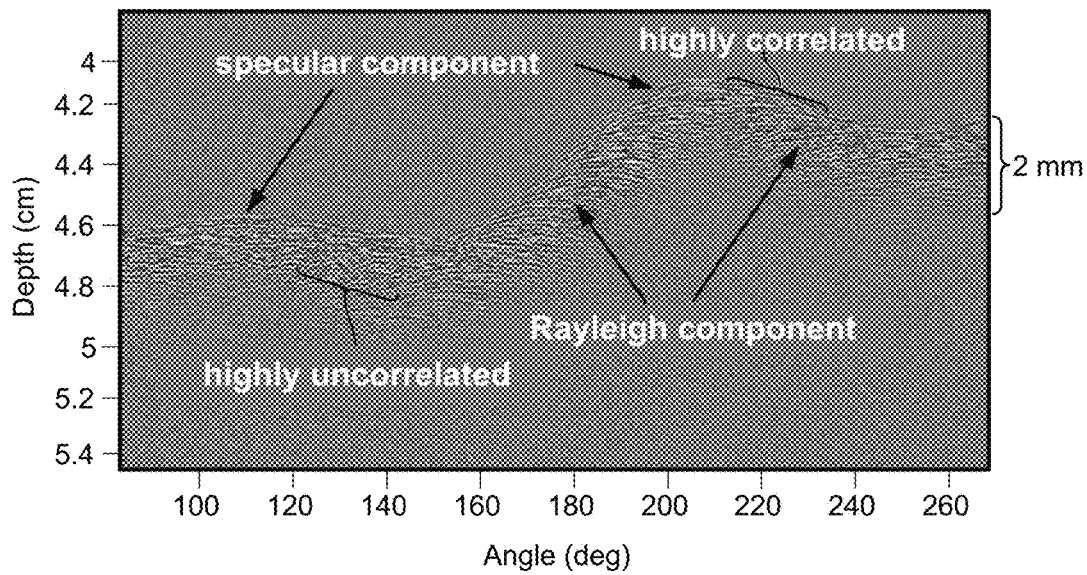
FIG. 6A shows a specular echo signature from a human femur bone suspended in water.
Figure 6B:
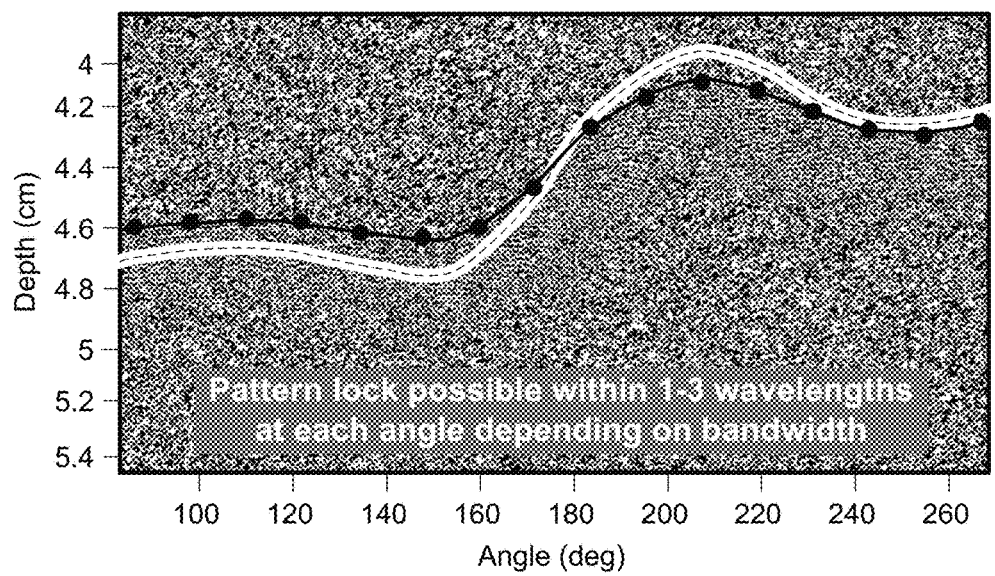
FIG. 6B is a specular echo signature showing patterns that match and do not match the specular component of the ultrasound echoes.

Due to the specular nature of bone reflections, echoes from the tissue-bone interface will present a different and identifiable echo signature compared to echoes from soft tissue and from within the bone itself. The specular echo signature from a human femur bone suspended in water is shown in FIG. 6A, in which these example results were measured and processed in example implementations of the disclosed system. Here, for example, echoes were recorded using a Philips L7-4 linear array operating at 5 MHz and approximately 80% FBW. The transmission occurred on a single element and echoes were received on the same element. Except for lensing in elevation, there was no focusing in azimuth. Echoes were recorded every 0.5 degree around the circumference of the bone. Here, a set of transmit angles were isolated over depth to zoom in on the echoes. It was observed that the specular component is approximately constant and remains highly correlated as a function of angle, whereas the Rayleigh component varies rapidly and decorrelates as a function of angle. It was also observed that the specular component forms a pattern as a function of angle. These observations were a key aspect of the disclosed technology. Patterns either match the specular component of the ultrasound echoes or they do not, for example, as depicted in FIG. 6B.

Figure 7A:
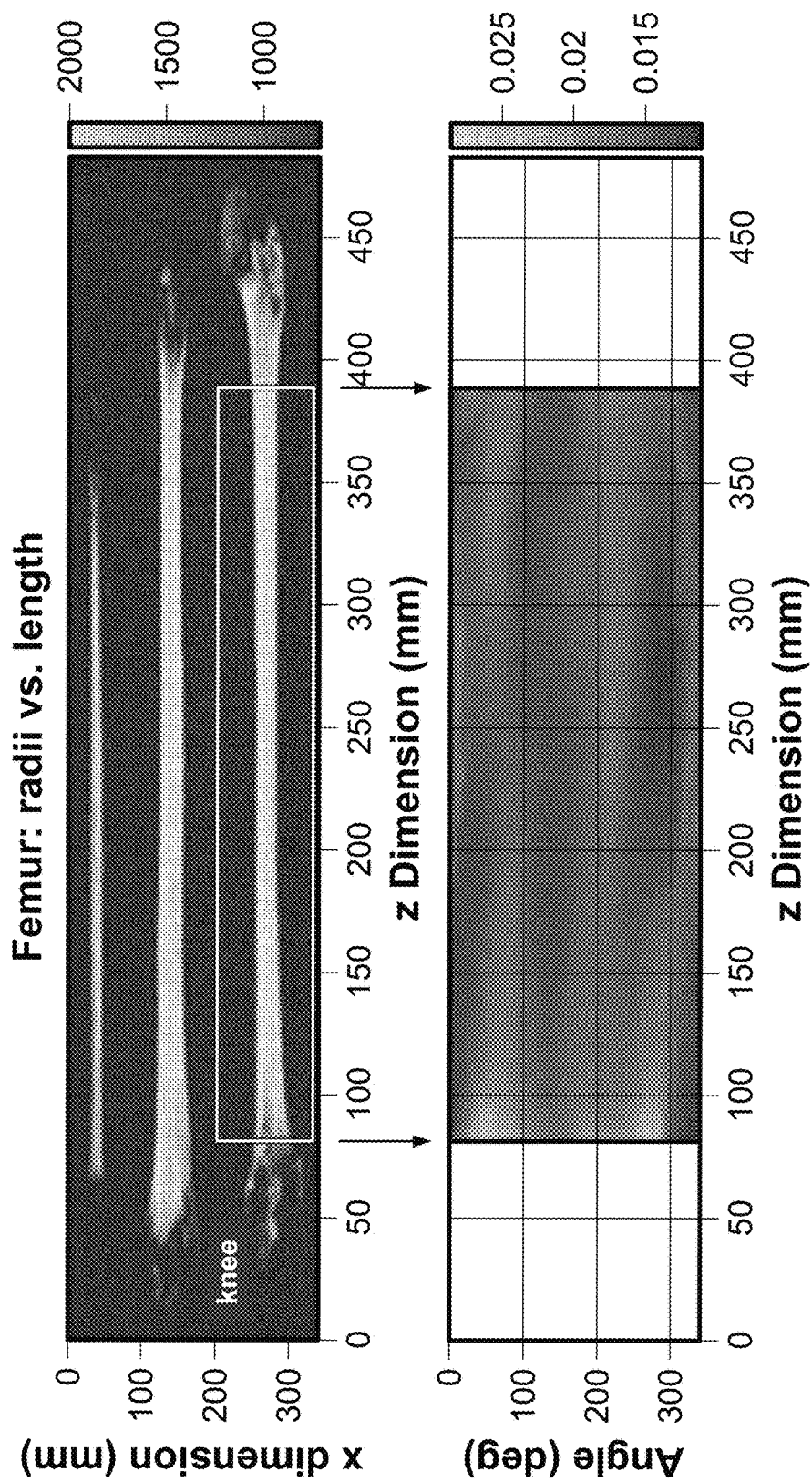
FIG. 7A shows an example radial patterns for a human femur.
Figure 7C:
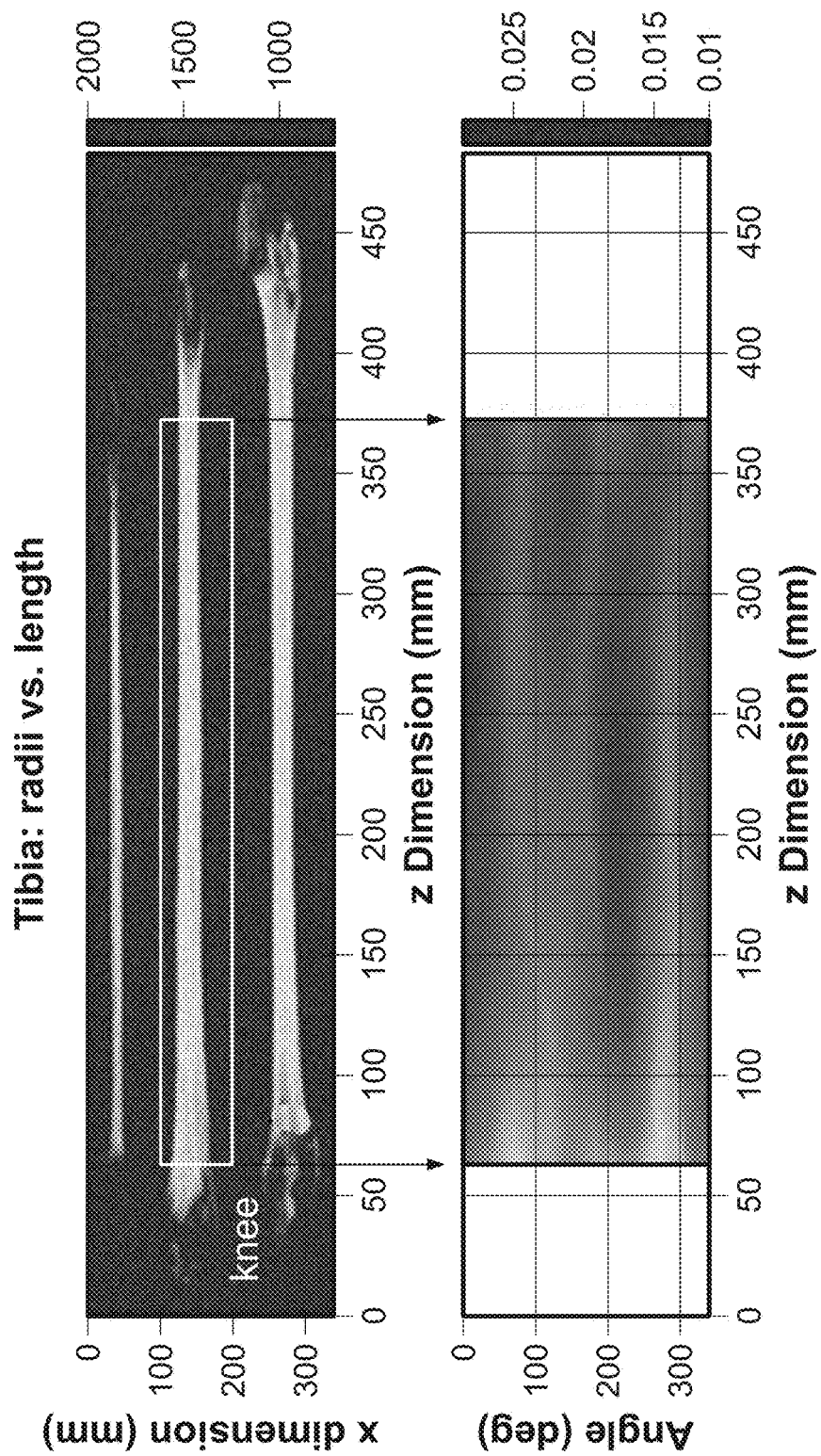
FIG. 7C shows an example radial pattern for a human tibia.
Figure 7D:
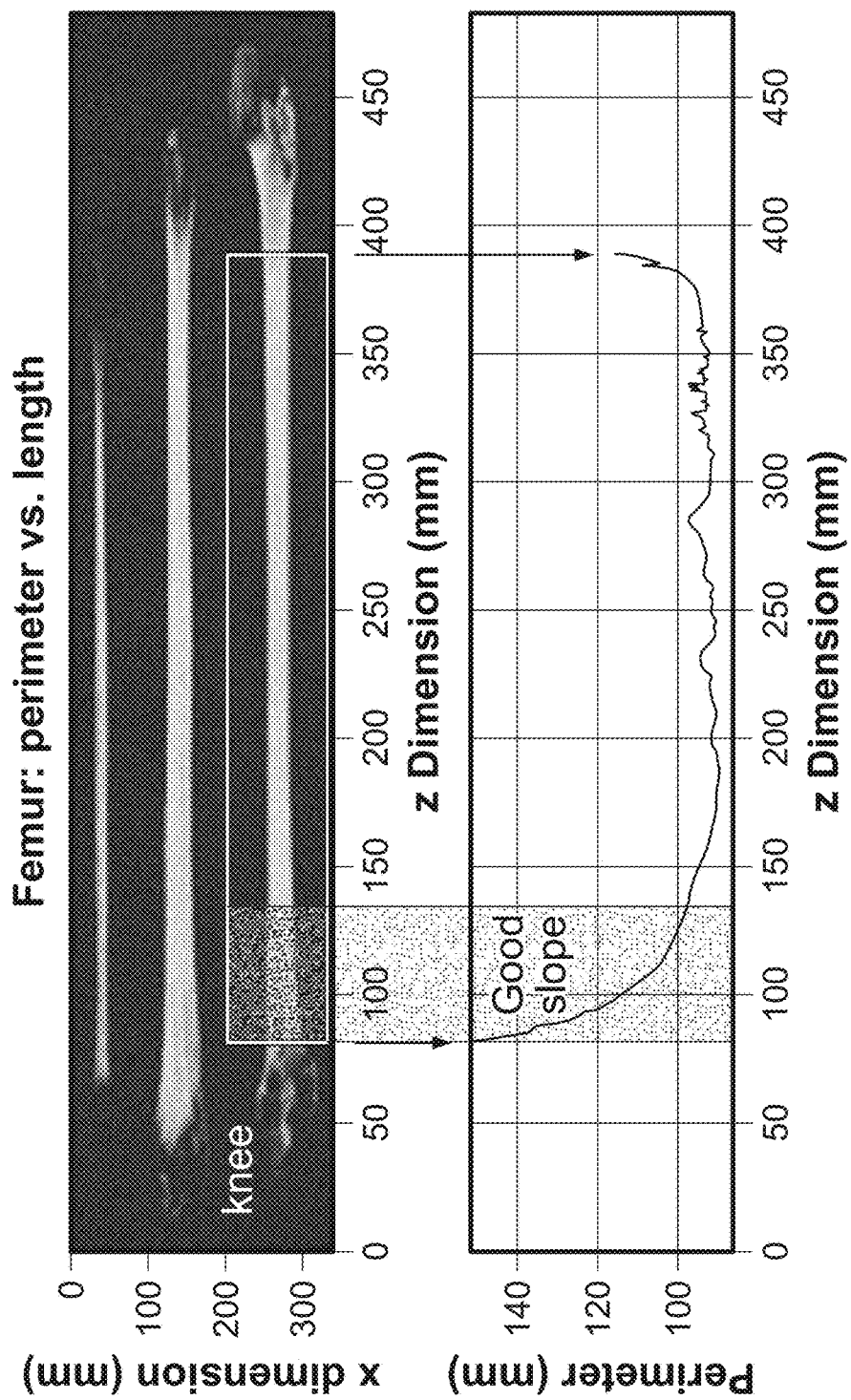
FIG. 7D shows the circumference or perimeter as a function of length for a femur.
Figure 7E:
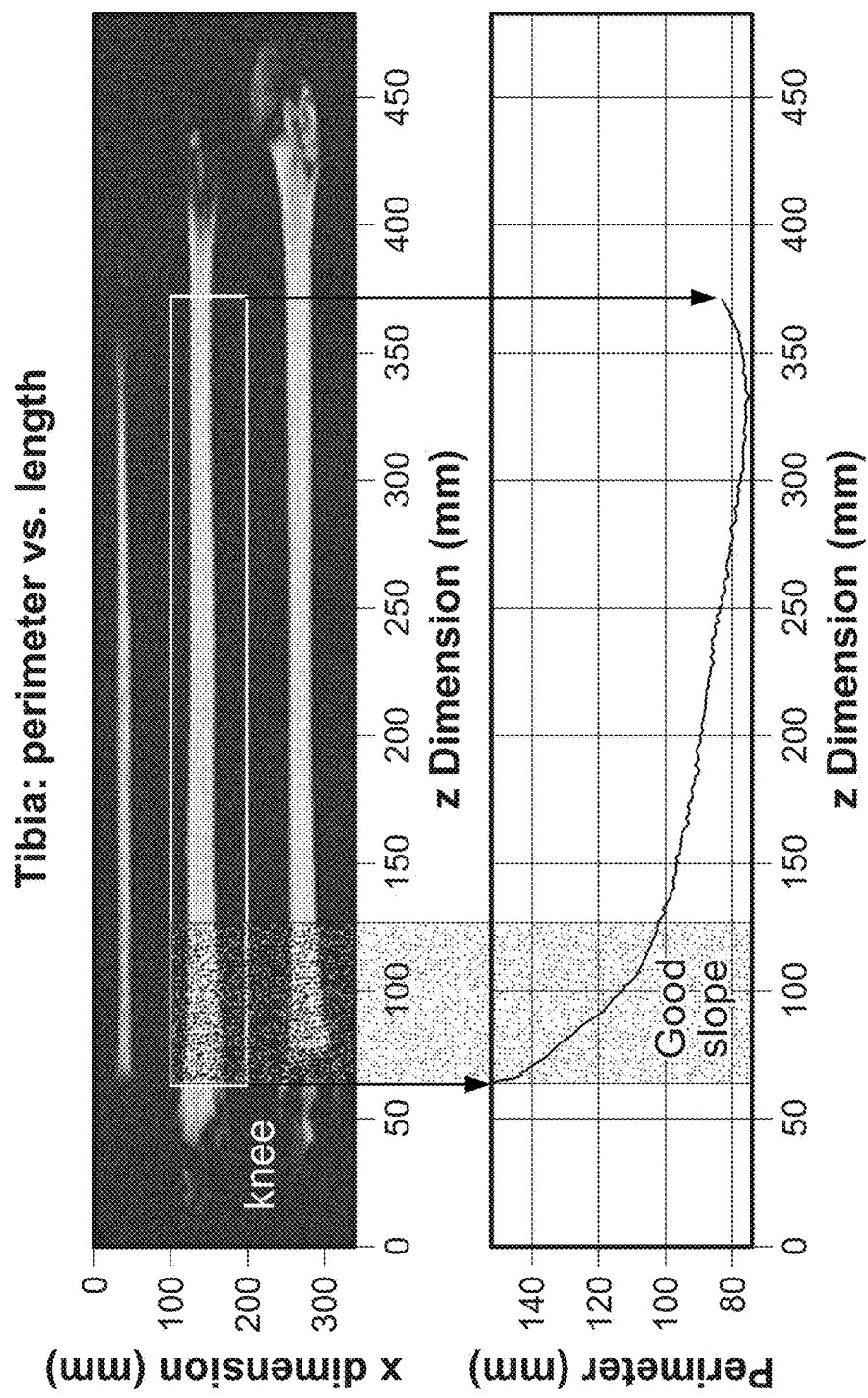
FIG. 7E shows the circumference or perimeter as a function of length for a tibia.

All bones, for example, the femur and tibia, have unique cross-sectional patterns over the length of the bone. FIGS. 7A and 7B show example radial patterns for a human femur, and FIG. 7C shows an example radial pattern for a human tibia, e.g., as obtained from CT volumes of both bones. Here, the radii measured to the centroid of the cross-sectional slice through bone along its length was quantified for 64 angles spanning 360 degrees. Additionally, the corresponding circumference (denoted perimeter in the original figures internally) of the bones as a function of length were quantified, as shown in FIG. 7D for the femur and FIG. 7E for the tibia. It was observed that some regions have more rapidly changing circumference than others, particularly close to the knee joint. It is in these regions that the cross-sectional patterns are the most sensitive and feature rich for bone tracking.

The pattern may be matched to a library of patterns determined from any means of tomographically imaging the bone, for example, as determined from a high resolution computed tomography (CT) image of the bone. The disclosed method includes a process for matching the specular acoustic echo pattern from bone sampled at one or more points on the bone to a library of patterns sampled according to the array geometry, e.g., in which the process can employ matching the pattern in order to match the topography of the bone, and thus, estimate the orientation of the bone in 6 DoF coordinate space according to the location of the transducers relative to a fixed point in space. It is important to note that the method is not "speckle tracking", as ultrasound speckle is due to random scattering, which is tracked using correlation between ultrasound images. "Specular" and "speckle" refer to different echo properties.

Signal processing is applied to the amplitude and phase information present in the received radio-frequency (RF) echoes to determine a pattern match against patterns automatically generated from a three dimensional library containing rigid bone information. Pattern matching can be achieved by statistically correlating information in the echo samples to patterns generated from the library. Penalty terms can be placed on each pattern sample to make the pattern matching robust to variable sound speed. Information about tissue types between the transducer and the bone surface can be used to inform the pattern matching algorithm for a more precise match, for example, sound speed information obtained from ultrasound tomography or inferred from MRI relaxation time information or CT Hounsfield unit information. Example algorithms may include, but are not limited to, linear cross correlation, circular cross correlation, sum-absolute-difference (SAD), linear regression, non-linear regression, first order statistics, second order statistics, higher-order statistics, Fourier transform, Mellin transform, Fourier-Mellin transform, Radon transform, Hankel transform, Eigenvalue decomposition, radial symmetry transform, singular value decomposition, pseudoinverse (e.g., generalized inverse, Moore-Penrose inverse, etc.), matrix inverse, pivot transformations, orthogonal transformations, wavelets, wavelet transform, matched filters, Hilbert transform, FIR filters, IIR filters, nonlinear filters, interpolators, and combinations thereof. The algorithms may operate on the amplitude, phase, or both amplitude and phase information contained within the echoes.

The inputs to the algorithm include, but are not limited to, a library of three dimensional information about the bone being tracked that is searchable through geometric projections (e.g., ray tracing), 6 DoF coordinate information about the transducer locations, a priori information about the sound speed of the coupling medium and expected sound speed through soft tissue, timing information about the acoustic echoes, amplitude scaling information about the acoustic echoes, and transmitted waveform information corresponding to each acoustic echo.

The outputs from the algorithm include, but are not limited to, the estimated 6 DoF coordinates of the bone being tracker, one or more confidence indicators of the pattern match, one or more estimates of the uncertainty in the estimated 6 DoF coordinates, and estimates of the tissue and bone velocity and acceleration along the axis of each transducer.

In some embodiments, for example, the algorithm may also contain a Kalman filter that models the physics of the array and bone movements. Inputs and outputs required of the Kalman filter will also be included, in addition to the aforementioned parameters.

In some embodiments, for example, the algorithm may also contain an optimizer that efficiently searches through potentially millions of patterns using a gradient decent or similar optimization approach.

In one example approach for bone tracking, the algorithm can include processes seeking to optimize several parameters simultaneously. FIG. 8A is an illustration depicting a simple arrangement of two transducers 800A and 800B transmitting and receiving echoes though soft tissue that contains a bone. For illustration purposes, the transducers 800A and 800B are arranged at 180 degrees with respect to each other; however, the concept is easily extended to multiple pairs of transducers at arbitrary multiple angles. The distance between the centers of the radiating apertures of the transducers given by $d_1$, which is the only known quantity. The distance from the left transducer to the bone is given by $d_3=c_3\tau_3$ and the distance from the right transducer to a different point on the bone is given by $d_4=c_4\tau_4$, where $c_3$ and $c_4$ are the respective average sound speeds and $\tau_3$ and $\tau_4$ are the respective echo times to the bone as estimated by the echo pattern match to the 3D bone model. The distance $d_2$ is the measured thickness of the bone as determined by the echo pattern match to the 3D bone model. The equation $d_1=d_2+d_3+d_4$ constitutes a conservation of distance such that the unknown sound speed parameters $c_3$ and $c_4$ are estimated. Additionally, as $d_2$ is determined from a rigid model and $d_1$ is rigidly known, $d_1-d_2$ is therefore a rigid distance, and $d_3+d_4$, though not rigidly known, are taken together as a rigid quantity. Thus, deviations in the estimated sum of $d_3+d_4$ from the rigid quantity $d_1-d_2$ may be assigned a penalty in an optimization cost function such that increasing deviations are assigned a linearly or nonlinearly increasing penalty. As $d_3+d_4$ are also functions of $c_3$ and $c_4$, respectively, linear or nonlinear penalties maybe assessed on $c_3$ and $c_4$ and included in the overall cost function. For example, if the average sound speed is known to be 1542 m/s, and the current echo pattern match calls for a sound speed of 1538 m/s, a penalty is assessed on the difference of 4 m/s as a linear or nonlinear function of the difference. It is also learned that a change in $d_3$ causes an equal and opposite change in $d_4$ due to the conservation of distance. This assumption is especially true over very short time scales of 1 millisecond or less, where the movement of the bone is likely bounded to be within 1 mm. Thus, the disclosed method, where the array surrounds the bone by at least 180 degrees, is especially robust to independent movement of the array with respect to the bone. The disclosed algorithm, for example, may be extended to an arbitrary number of pairs of transducers or acoustic beams, with each transducer or beam or collection of transducers of collections of beams having its own objective function as shown in FIG. 8B. Here, the goal is to minimize $f_n$ over N pairs. It is also seen that $f_n$ is a function of the 6 DoF coordinate of the bone as estimated from the pattern matching algorithm. The robustness increases as the number of transducers or beams increases. The method is not strictly limited to pairs of transducers or beams; however, the preferred embodiment consists of a collection of opposite pairs where the angle between each pair is 180 degrees.

In some embodiments, for example, the disclosed algorithm is as follows. Recorded echoes are processed and one or more pattern matching algorithms roughly matches the specular echo patterns to a 3D model of the bone of interest to initialize a set of objective functions. During this initial match, the sound speed of the tissue is assumed to be some value, for example, 1540 m/s. With the objective functions initialized, a multivariate optimizer determines the best fit to the 3D model by varying all parameters except for the known distance between each pair of transducer elements. At each iteration, the optimizer refines the search of the 3D model over a constrained set of 6 DoF coordinates according in order to minimize the set of objective functions that may include one or more penalty terms (not shown in FIG. 7B, but as described above), e.g., a penalty on the sound speed. The optimizer may also incorporate additional inputs such as velocity and acceleration measured from the acoustic echoes near the estimated location of the tissue-bone interface. The optimizer may also incorporate inputs from the real-time estimated velocity and acceleration of the acoustic structure as tracked externally. The optimizer may also incorporate outputs from a Kalman filter that filters multiple velocity and acceleration inputs to produce a filtered respective velocities and accelerations. At each iteration, the algorithm outputs parameters including, but not limited to, estimated 6 DoF coordinates of the bone, pattern match metrics, objective function values, penalty estimates, and estimated velocities and accelerations.

One example applications of the present technology is to track the tibia and femur bones in the leg during computer assisted surgery (CAS) of the knee, including, but not limited to, total knee arthroplasty (TKA) and total knee replacement (TKR). Current state-of-the-art TKA and TKR require surgical placement of an alignment rod into both the tibia and femur for rigidly tracking both bones using external optical trackers. To place the alignment rod, a small incision is made in the skin, a hole is drilled into the bone, and the rod is screwed into the hole. The procedure is invasive, resulting in unsightly scarring on the skin. It potentially compromises the integrity of the bone, particularly for elderly patients. It is a site of potential infection, which can lead to post-surgical complications. The disclosed system is envisioned to replace this invasive tracking with non-invasive tracking as described herein. FIG. 3C shows an example embodiment employing two arrays of transducers per leg, including attaching two acoustic transducer array structures 110 on the leg: one for tracking the tibia and one for tracking the femur.

According to the Anthropometric Reference Data for Children and Adults: United States, 2003-2006, National Health Statistics Reports, No. 10, Oct. 22, 2008, pp. 1-45, the maximum calf circumference is roughly 48 cm or 15 cm in diameter across all ages and races, and the maximum mid-thigh circumference is roughly 70 cm or 22 cm in diameter across all ages and races. Thus, a fixed, 15 cm diameter array accommodates the leg just above the knee for most of the population, and is large enough to slide over the calf and knee of the majority of the population. Such an array would operate preferably with a center frequency in the vicinity of 5 MHz.

In some embodiments, for example, the acoustic echoes are displayed on monitor similar to ultrasound echoes are displayed on a clinical ultrasound scanner. The echoes may be displayed in raw format as RF echoes or in grayscale as log compressed amplitude or B-mode images. The pattern match may be overlaid on the echoes so the user can observe positioning and pattern matching. A three dimensional rendering of the bone being tracked can also be displayed in real-time as the user manipulates the body part.

In some embodiments, for example, coordination of acoustic transmission, reception, echo processing, and output communication takes place on a non-transitory computer readable medium that includes a processor, a display, a means of digital communication, and electronics for acoustic transmission, electronics for reception of acoustic echoes, and electronics for recording and storing acoustic echoes.

Additional information pertaining to the disclosed technology is described in a later section of this document under the heading "A Specific Example An OTS System."

EXAMPLES

The following examples are illustrative of several embodiments of the present technology. Other exemplary embodiments of the present technology may be presented prior to the following listed examples, or after the following listed examples.

In one example of the present technology (example 1), an acoustic orthopedic tracking system includes an acoustic probe device structured to include a support frame having a curved shape to interface a body part of a biological subject, and an array of transducer elements arranged on the curved support frame and operable to transmit acoustic waveforms toward a target volume of an orthopedic structure in the body part and to receive returned acoustic waveforms that return from at least part of the target volume of the orthopedic structure; an acoustic coupling component coupled to the array of transducer elements and operable to conduct the acoustic waveforms between the transducer elements and the body part of the biological subject when in contact with the acoustic coupling component; a signal generation and processing device in communication with the acoustic probe device and structured to include (i) a transmit and receive electronics (TRE) unit, and (ii) a data processing unit including a memory to store data and a processor coupled to the memory to process data, in which the TRE unit includes a waveform generator in communication with the data processing unit and one or more waveform synthesizers in communication with the waveform generator to generate one or more waveforms according to waveform information provided by the data processing unit via the waveform generator, in which the transmittable acoustic waveforms correspond to the one or more waveforms generated by the signal generation and processing device; and a position tracking device in communication with the signal generation and processing device and operable to track the position of the transducer elements of the acoustic probe device, in which the data processing unit is operable to process the received returned acoustic waveforms to produce a data set including the information from the at least part of the target volume, the information including at least one of location coordinates, orientation, or motion of the orthopedic structure of the body part with 6 DoF.

Example 2 includes the system of example 1, in which the data processing unit is in communication with a surgical system and operable to transfer the produced data set to the surgical system such that the surgical system can perform an operation or procedure on the orthopedic structure based on the information contained in the data set.

Example 3 includes the system of example 1, in which the position tracking device includes an optical sensor including one or more of a camera, an image sensor including a charge-coupled device (CCD), or a light emitting diode (LED).

Example 4 includes the system of example 1, in which the acoustic coupling component includes a hydrogel including one or more polymerizable materials that form a network structured to entrap an aqueous fluid inside the hydrogel, in which the hydrogel is structured to conform to an outer surface of the body part and the transducer elements, in which, when the acoustic coupling component is in contact with the outer surface of the body part, the acoustic coupling component provides an acoustic impedance matching between the receiving medium and the acoustic signal transducer elements.

Example 5 includes the system of example 4, in which the hydrogel is structured to conform to the body part in complete contact with the surface, without packets of air or voids formed between acoustic coupling component and the body part.

Example 6 includes the system of example 1, in which the TRE unit includes an array of analog to digital (A/D) converters to convert the received returned acoustic waveforms received by the array of transducer elements of the acoustic probe device from analog format to digital format as a received waveform that includes information of at least part of the target volume, one or more amplifiers in communication with the one or more waveform synthesizers to modify the waveforms provided to the acoustic probe device for transmission, and one or more pre-amplifiers in communication with the acoustic probe device and the array of A/D converters to modify the received returned acoustic waveforms provided to the A/D converters.

Example 7 includes the system of example 1, in which the acoustic probe device includes a signal interface module connectable to the TRE unit of the signal generation and processing device, the signal interface module including a multiplexing unit in communication with the array of transducer elements to select one or more transducing elements of the array to transduce the waveforms into the corresponding acoustic waveforms, and to select one or more transducing elements of the array to receive the returned acoustic waveforms.

Example 8 includes the system of example 1, in which the signal generation and processing device is operable to generate arbitrary waveforms, in which the arbitrary waveforms include an arbitrary waveform describable mathematically.

Example 9 includes the system of example 8, in which the arbitrary waveforms include one or more of rectangular pulses, triangular pulses, impulse pulses, Gaussian pulses, sinusoidal pulses, sinc pulses, Mexican hat wavelet pulses, Haar wavelet pulses, linear FM chirped pulses, hyperbolic FM chirped pulses, coded pulses, binary coded pulses, ternary coded pulses, phase coded pulses, complementary binary coded pulses, amplitude coded pulses, phase and amplitude coded pulses, frequency coded pulses, stepped sine wave pulses, shaped spectrum pulses, or combinations thereof.

Example 10 includes the system of example 8, in which the signal generation and processing device is operable to arbitrarily delay, apodize, steer and beamform the arbitrary waveforms.

Example 11 includes the system of example 1, in which the signal generation and processing device is operable to generate a composite waveform including two or more of individual orthogonal coded waveforms corresponding to one or more frequency bands that are generated by the one or more waveform synthesizers according to the waveform information, in which the individual orthogonal coded waveforms are mutually orthogonal to each other and correspond to different frequency bands, such that each of the individual orthogonal coded waveforms includes a unique frequency with a corresponding phase.

Example 12 includes the system of example 11, in which each of the individual orthogonal coded waveforms includes a plurality of amplitudes and a plurality of phases that are individually amplitude weighted and individually phase weighted, respectively.

Example 13 includes the system of example 11, in which the signal generation and processing device is operable to determine a frequency band, an amplitude, a time-bandwidth product parameter, and a phase parameter of each individual orthogonal coded waveform.

Example 14 includes the system of example 13, in which the phase parameter is determined from a set of a pseudo-random numbers or from a set of deterministic numbers.

Example 15 includes the system of example 1, in which the target volume includes a tissue structure of the biological subject, and the shaped section of the probe device is in contact with the body part of the biological subject.

Example 16 includes the system of example 15, in which the body part includes an abdomen, a thorax, a neck including the throat, an arm, a leg, a knee joint, a hip joint, an ankle joint, an elbow joint, a shoulder joint, a wrist joint, a breast, a genital, or a head including the cranium.

Example 17 includes the system of example 15, in which the biological structure includes a cancerous or noncancerous tumor, an internal legion, a connective tissue sprain, a tissue tear, or a bone.

In one example of the present technology (example 18), a method for producing orthopedic data using acoustic waveforms includes transmitting acoustic signals from a plurality of acoustic transducer elements in an array of an acoustic probe device toward a target volume of an orthopedic structure of a body part of a biological subject to which the acoustic probe device is in contact; receiving acoustic echoes that return from at least part of the target volume at one or more of the transducer elements, in which the received acoustic echoes include at least some waveform components corresponding to the transmitted acoustic signals; determining positions of the acoustic transducer elements of the acoustic probe device during the transmitting of the acoustic signals and the receiving of the acoustic echoes; processing the received acoustic echoes to produce spatial information corresponding to returned acoustic echoes from the orthopedic structure including one or both of soft tissue and bone, in which the processing includes determining an echo signature including unique specular pattern data associated with the acoustic echoes returned from a tissue-bone interface of the orthopedic structure; and determining a location or an orientation, or both, of the orthopedic structure in a 6 DoF coordinate space based on the spatial information from the orthopedic structure by quantitatively comparing to sample patterns using the determined positions of the acoustic transducer elements.

Example 19 includes the method of example 18, including determining topography of the bone of the orthopedic structure in a 6 DoF coordinate space based on the spatial information from the orthopedic structure by quantitatively comparing to sample patterns using the determined positions of the acoustic transducer elements.

Example 20 includes the method of example 18, in which the determining the positions of the acoustic transducer elements includes determining location of the transducer elements relative to a fixed point in three dimensional space.

Example 21 includes the method of example 18, in which the transmitting the acoustic signals includes transmitting sequentially one-at-a-time, simultaneously, or in a time-staggered or time-delayed pattern.

Example 22 includes the method of example 18, in which the processing the received returned acoustic waveforms includes amplifying, filtering, and digitally sampling the acoustic echoes corresponding to the spatial information from the soft tissue and the bone of the orthopedic structure; and storing the spatial information as data.

Example 23 includes the method of example 18, in which the unique specular pattern data includes cross-sectional patterns over a length of the bone for the sampled spatial information.

Example 24 includes the method of example 18, in which the produced spatial information includes spectral information corresponding to the acoustic echoes from the orthopedic structure.

Example 25 includes the method of example 18, further including providing the location and/or orientation of the orthopedic structure in a data set to a surgical system operable to perform an operation or procedure on the orthopedic structure based on the information contained in the data set.

Example 26 includes the method of example 25, in which the providing the data set to the surgical system includes transferring the data set to the surgical procedure in real time during implementations of the method include the transmitting of the acoustic signals and the receiving of the acoustic echoes into and out of the biological subject during the operation or procedure by the surgical system.

In one example of the present technology (example 27), an acoustic orthopedic tracking device includes an acoustic probe including a support frame having a curved shape to interface a body part of a biological subject, and an array of transducer elements arranged on the curved support frame and operable to transmit acoustic waveforms toward a target volume of an orthopedic structure in the body part and to receive acoustic echoes that return from at least part of the target volume of the orthopedic structure; an acoustic coupling medium coupled to the array of transducer elements and operable to conduct the acoustic waveforms between the transducer elements and the body part of the biological subject when in contact with the acoustic coupling medium; and a signal generation and processing unit in communication with the transducer elements and structured to include a housing, a transmit and receive electronics (TRE) unit disposed in the housing, and a data processing unit disposed in the housing and including a memory to store data and a processor coupled to the memory to process data, in which the TRE unit includes a waveform generator in communication with the data processing unit and one or more waveform synthesizers in communication with the waveform generator to generate one or more waveforms according to waveform information provided by the data processing unit via the waveform generator, in which the acoustic waveforms correspond to the one or more waveforms generated by the signal generation and processing unit, and the returned acoustic echoes include at least some waveform components corresponding to the transmitted acoustic waveforms, and in which the data processing unit is configured to process the returned acoustic echoes to produce spatial information corresponding to the acoustic echoes from the orthopedic structure including one or both of soft tissue and bone by identifying specular pattern data associated with the acoustic echoes returned from a tissue-bone interface of the orthopedic structure, and to determine a location or an orientation, or both, of the orthopedic structure in a 6 DoF coordinate space based on the spatial information from the orthopedic structure by quantitatively comparing to sample patterns using positional data of the transducer elements during transmit and receive operations of the acoustic probe.

Example 28 includes the device of example 27, in which the signal generation and processing unit is operable to receive the positional data from a position tracking device in communication with the signal generation and processing unit to track the position of the transducer elements of the acoustic probe device during the transmit and receive operations of the acoustic probe.

Example 29 includes the device of example 27, in which the data processing unit is operable to generate a data set including the determined location, orientation, or location and orientation of the orthopedic structure of the body part in the 6 DoF coordinate space.

Example 30 includes the device of example 29, in which the data processing unit is in communication with a surgical system and operable to transfer the produced data set to the surgical system such that the surgical system can perform an operation or procedure on the orthopedic structure based on the information contained in the data set.

Example 31 includes the device of example 27, in which the acoustic coupling medium includes a hydrogel including one or more polymerizable materials that form a network structured to entrap an aqueous fluid inside the hydrogel, in which the hydrogel is structured to conform to an outer surface of the body part and the transducer elements, in which, when the acoustic coupling medium is in contact with the outer surface of the body part, the acoustic coupling medium provides an acoustic impedance matching between the body part and the acoustic signal transducer elements.

Example 32 includes the device of example 27, in which the TRE unit includes an array of analog to digital (A/D) converters to convert the returned acoustic echoes received by the array of transducer elements from analog format to digital format as a received waveform that includes information of at least part of the target volume, one or more amplifiers in communication with the one or more waveform synthesizers to modify the waveforms provided to the acoustic probe for transmission, and one or more pre-amplifiers in communication with the acoustic probe and the array of A/D converters to modify the returned acoustic echoes provided to the A/D converters.

Example 33 includes the device of example 27, in which the acoustic probe includes a signal interface module connectable to the TRE unit of the signal generation and processing unit, the signal interface module including a multiplexing unit in communication with the array of transducer elements to select one or more transducing elements of the array to transduce the waveforms into the corresponding acoustic waveforms, and to select one or more transducing elements of the array to receive the returned acoustic echoes.

Example 34 includes the device of example 27, in which the signal generation and processing unit is operable to generate arbitrary waveforms, in which the arbitrary waveforms include an arbitrary waveform describable mathematically.

Example 35 includes the device of example 34, in which the arbitrary waveforms include one or more of rectangular pulses, triangular pulses, impulse pulses, Gaussian pulses, sinusoidal pulses, sinc pulses, Mexican hat wavelet pulses, Haar wavelet pulses, linear FM chirped pulses, hyperbolic FM chirped pulses, coded pulses, binary coded pulses, ternary coded pulses, phase coded pulses, complementary binary coded pulses, amplitude coded pulses, phase and amplitude coded pulses, frequency coded pulses, stepped sine wave pulses, shaped spectrum pulses, or combinations thereof.

Example 36 includes the device of example 34, in which the signal generation and processing unit is operable to beamform and steer the arbitrary waveforms.

Example 37 includes the device of example 27, in which the signal generation and processing unit is operable to generate a composite waveform including two or more of individual orthogonal coded waveforms corresponding to one or more frequency bands that are generated by the one or more waveform synthesizers according to the waveform information, in which the individual orthogonal coded waveforms are mutually orthogonal to each other and correspond to different frequency bands, such that each of the individual orthogonal coded waveforms includes a unique frequency with a corresponding phase.

Example 38 includes the device of example 37, in which each of the individual orthogonal coded waveforms includes a plurality of amplitudes and a plurality of phases that are individually amplitude weighted and individually phase weighted, respectively.

Example 39 includes the device of example 37, in which the signal generation and processing unit is operable to determine a frequency band, an amplitude, a time-bandwidth product parameter, and a phase parameter of each individual orthogonal coded waveform.

Example 40 includes the device of example 39, in which the phase parameter is determined from a set of a pseudo-random numbers or from a set of deterministic numbers.

Example 41 relates a tomographic array for use in an acoustic orthopedic tracking system that includes a plurality of transducer elements arranged to form a curved array configurable to be positioned around a subject of interest that includes both soft tissue and a target bone, each transducer element capable of both transmitting and receiving an acoustic wave, each transducer element having a height, a width and being positioned at a distance from a neighboring element. The tomographic array also includes an acoustic coupler that forms an acoustic signal transmission interface between the plurality of transducer elements and the subject of interest.

Example 42 relates to configuration in which each transducer element is independently addressable to either transmit or receive an acoustic signal to or from the subject of interest.

Example 43 relates to a configuration in which the tomographic array is operable with an acoustic wave including a particular wavelength, and each transducer element is positioned at a distance from a neighboring element in a range 0.5 to 2 times the particular wavelength. In this example, the acoustic wave can include a range of wavelengths, and the distance between the neighboring elements can be selected to be in the range 0.5 to 2 times a wavelength that is selected or chosen from the range of wavelengths.

Example 44 relates to a configuration in which the tomographic array is configured to allow a contiguous first set of the transducer elements to be energized for transmission of a first acoustic signal.

Example 45 relates to a configuration in which a focal point of the acoustic signal is positioned within a sector subtended by an arc length and an angle spanned by the contiguous first set of the transducer elements.

Example 46 relates to a configuration in which the tomographic array is configured to allow a contiguous second set of the plurality of transducer elements to be energized for transmission of a second acoustic signal.

Example 47 relates to a configuration in which the first set and the second set have at least one transducer element in common.

Example 48 relates to a configuration in which the tomographic array is configured to include a receive aperture that includes a first set of transducer elements from the plurality of transducer elements, and a transmit aperture that includes a second set of transducer elements from the plurality of transducer elements, where the receive aperture is equal to or larger than the transmit aperture and the transmit aperture is positioned entirely within the receive aperture.

Example 49 relates to a configuration in which the tomographic array is configured to include a first and a second aperture positioned within the tomographic array to include non-overlapping transducer elements, each aperture capable of both receiving and transmitting an acoustic signal, and the first aperture includes a first number of transducer elements, the second aperture includes a second number of transducer elements, the first number and the second number having been selected to maintain the same f-number at a surface of the subject of interest (e.g., a target bone) for each of the first and the second aperture.

Example 50 relates to a configuration in which the tomographic array is configured to a first transmit aperture and a first receive aperture, and wherein the first receive aperture is positioned between 90 degrees and −90 degrees away from a phase center of the first transmit aperture.

Example 51 relates to a method for transmitting and receiving an acoustic signal in an imaging system that includes a plurality of transducer elements arranged to form a curved array configurable to be positioned around a subject of interest that includes both soft tissue and a target bone. Such method includes energizing a first set of transducer elements that form a transmit aperture for transmitting the acoustic signal to the subject of interest, receiving at a second set of transducer elements that form a receive aperture receiving at least a portion of the transmitted acoustic signal after interaction with the subject of interest. The first set of transducer elements includes at least one transducer element, and the second set of transducer elements includes a plurality of contiguous transducer elements each separated from a neighboring transducer element by a distance without an intervening transducer element.

Example 52 relates to energizing the first set of transducer elements that includes forming a first acoustic signal having a focal point that is positioned within a sector subtended by an arc length and an angle spanned by a plurality of transducer elements within the first set of transducer elements.

Example 53 relates to forming a second acoustic signal using a third set of transducer elements that has at least one transducer element in common with the first set.

Example 54 relates to a scenario in which the receive aperture is equal to or larger than the transmit aperture and the transmit aperture is positioned entirely within the receive aperture on an arc formed by the plurality of transducer elements.

Example 55 relates to a scenario in which the first set and the second set of transducer elements have no transducer elements in common, the first set and the second set of transducer elements each operate as either the receive aperture or as the transmit aperture, and the first set and the second set of transducer elements are selected to maintain the same f-number at a surface of the subject of interest (e.g., a target bone) for apertures formed by the first and the second set of transducer elements.

Example 56 includes energizing a third set of transducer elements to transmit another acoustic signal and receiving at least a portion of an acoustic signal that is produced due to interaction of the acoustic signal produced by the third set of transducer elements with the subject of interest.

Example 57 includes iteratively energizing different sets of transducer elements and receiving acoustic signals produced as a result of interaction of acoustic waves with the subject of interest until all of the plurality of transducer elements have been energized at least once.

Example 58 relates to a scenario in which, in each iteration, different sets of transducer elements are selected in a random selection pattern.

Example 59 relates to a scenario in which, in each iteration, different sets of contiguous transducer elements are selected.

Example 60 relates to a scenario in which, in each iteration, different sets of non-contiguous transducer elements are selected.

Example 61 relates to a scenario in which each iteration includes transmission of two or more acoustic signals that are separated in time from one another, followed by reception of two or more acoustic signals that are separated in time.

Example 62 includes the device of example 43 that comprises one transmit channel addressable to all transducer elements and one receive channel addressable to all transducer elements.

Example 63 relates to example 62 in which the transmit element is selected from the plurality of elements and the receive element is selected to be the same as the transmit element for a given transmission.

Example 64 includes the device of example 43 that comprises one transmit channel addressable to all transducer elements and two receive channels addressable to all transducer elements.

Example 65 relates to example 64 in which the transmit element is selected from the plurality of transducer elements and one receive element is selected to be the same as the transmit element for a given transmission and the second receive element is selected to be a neighboring element with no elements in between.

Example 66 relates to example 64 in which the transducer elements are successively indexed and one receive channel is addressable to even transducer element indices and the other receive channel is addressable to odd transducer element indices.

Specific Example of an OTS System

The disclosed acoustic orthopedic tracking system (OTS) can be used to augment a surgical system, e.g., such as a robotic arm for interactive orthopedic surgery, by providing accurate, timely, 6 DoF bone positions before and during orthopedic surgical operations. The disclosed acoustic OTS technology can provide non-imaging data (e.g., range Doppler measurement), and can additionally or alternatively provide imaging data. It is envisioned that, due to the advantages proffered by the disclosed acoustic OTS, the disclosed system will replace, at least in part, current tracking systems which typically utilizes LED electro-optical trackers pinned to the patient's femur and tibia.

In some implementations, the disclosed acoustic OTS can provide a third party surgical navigation system (3PSNS) with relative positional data intra-operatively for human femur and tibia bone targets. This example implementation of the disclosed acoustic OTS is applicable to human femur and tibia bones, and the system is also engineered to characterize other orthopedic anatomical features and structures, e.g., adaptation to other human or animal bone targets.

In some embodiments, for example, the disclosed acoustic OTS includes an array of ultrasound transducers at locations and angular positions that can transmit and receive ultrasound signal data and be concurrently tracked by a 3D position tracking system, e.g., such as an electro-optical SNS. Positional data can be referenced to a coordinate system that is registered to 3D models of the bones to be tracked for robotic assisted orthopedic surgeries. In some implementations, for example, the 3D bone models can be prepared prior to the surgical operation by CT scan or other 3D imaging modality as part of the surgical planning process.

Figure 9:
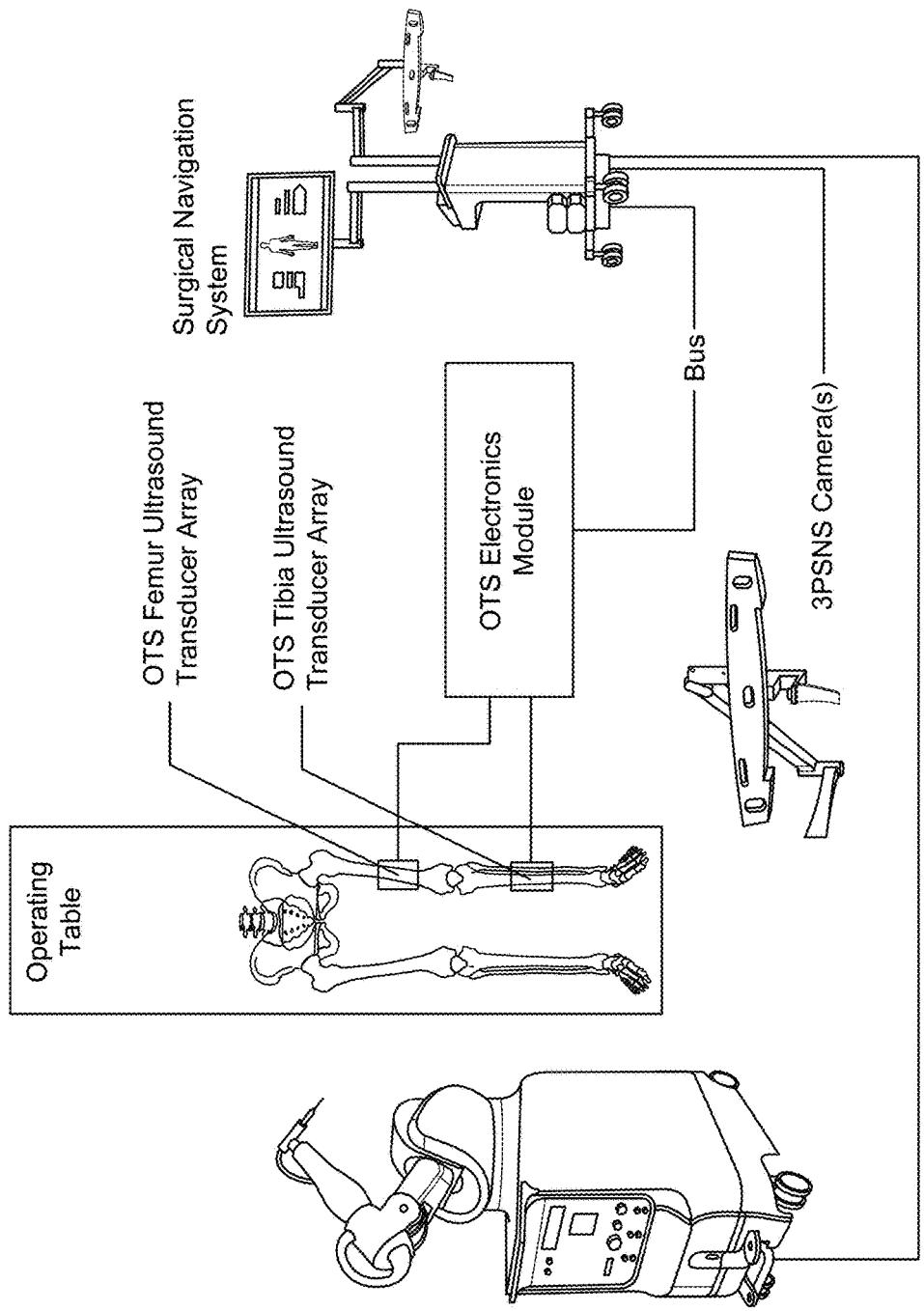
FIG. 9 shows an example system in which the acoustic OTS system is integrated with a third party surgical navigation system (3PSNS).

FIG. 9 shows the disclosed acoustic OTS system integrated with example 3PSNS system components. In the example shown in FIG. 9, the exemplary OTS Ultrasound transducer arrays are attached to the patient's external leg skin surfaces to monitor the position of the patient's bones. The OTS provides positional and angular reference data to the example electro-optical SNS allowing the 3PSNS to determine the position of the 3PSNS optical arrays with respect to the patient's bone coordinate system.

Figure 10A:
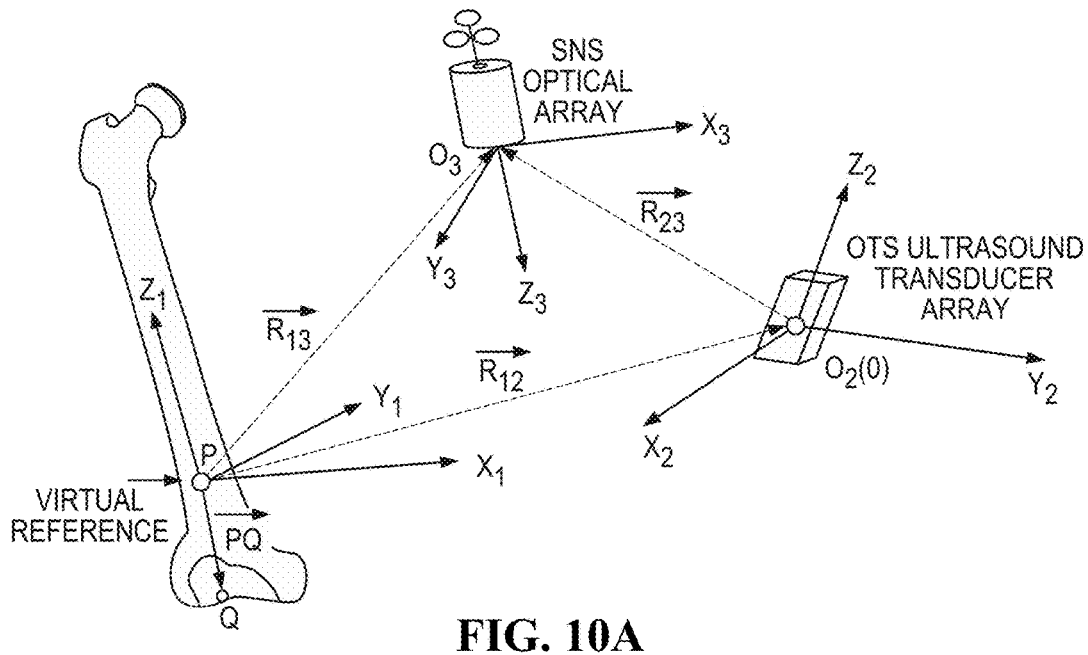
FIG. 10A shows the relationship between the patient's bone coordinate system, the OTS ultrasound transducer array coordinate system and the 3PSNS optical array coordinate system.

FIG. 10A shows the relationship between the patient's bone coordinate system ($x_1$, $y_1$, $z_1$), the example OTS ultrasound transducer array coordinate system ($x_2$, $y_2$ and $z_2$) and the example 3PSNS optical array coordinate system ($x_3$, $y_3$ and $z_3$) at time t=0, when the OTS acquires the arbitrary point, P, and its associated coordinate system ($x_1$, $y_1$, $z_1$).

For example, with the SNS optical array knowing the relative position of the reference point, P, with respect to the SNS frame of reference, the SNS can register the positional relationship between point P and the "known" navigational points, Q, of the patient's bone surface.

Figure 10B:
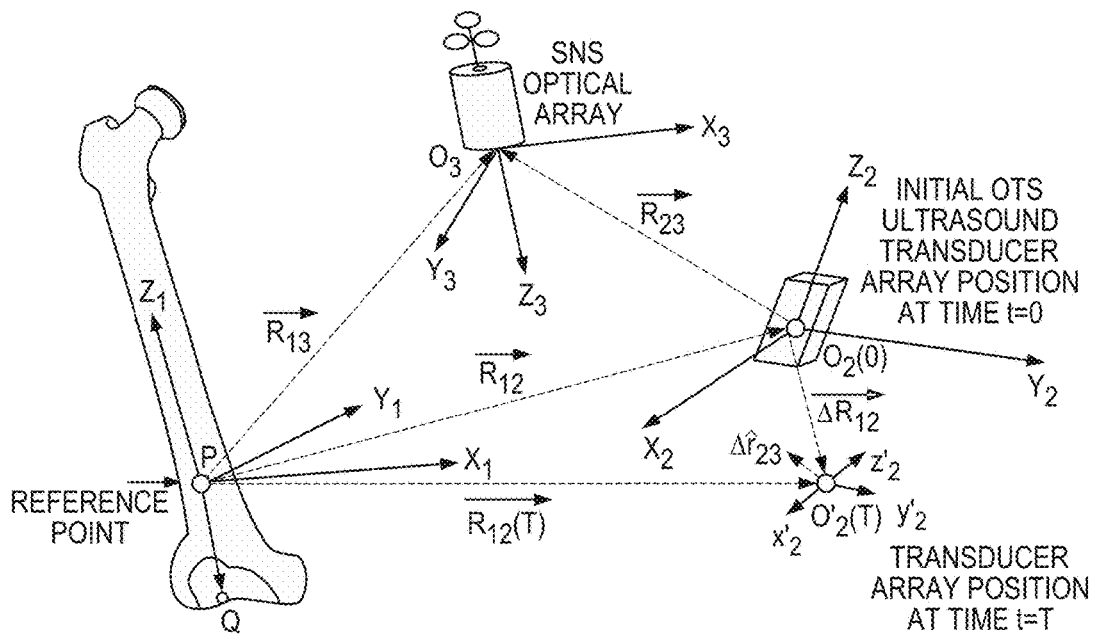
FIG. 10B illustrates a bone tracking coordinate system similar to FIG. 10A but showing ultrasound array displacement at future time t=T.

Using a software 3D solid model of the bone prepared from CT scan data, for example, the received ultrasound signals are matched to the bone model to continuously determine the positional relationship of OTS ultrasound array coordinate system ($x'_2$, $y'_2$, $z'_2$) to the bone coordinate system ($x_1$, $y_1$, $z_1$) at any future time t=T after initial acquisition. As the array is not fixed to the patient's bone, any movement of the array relative to the bone is measured and reported to the 3PSNS system as a relative position ($x'_2$, $y'_2$, $z'_2$) including angular changes for full 6 DoF tracking, as illustrated in FIG. 10B. FIG. 10B shows a diagram depicting a bone tracking coordinate system showing ultrasound array displacement at future time t=T.

The example acoustic OTS provides both translational data $\Delta R_{12}(T)$, plus transducer coordinate rotational information as 3×3 directional cosine matrix elements, or in any other mutually agreed format, for the transducer array coordinate system ($x'_2$, $y'_2$, $z'_2$) for all sample times, T, after acquisition. If for any reason a "track lost" condition occurs, the OTS will go in an acquisition mode to reacquire the original virtual Reference Point, P, and associated coordinate system and set a digital "track lost" flag. In some implementations, for example, the only anticipated condition where the OTS would not automatically reacquire point P would be if the OTS Transducer Array for some reason became detached from the patient's skin.

Figure 11:
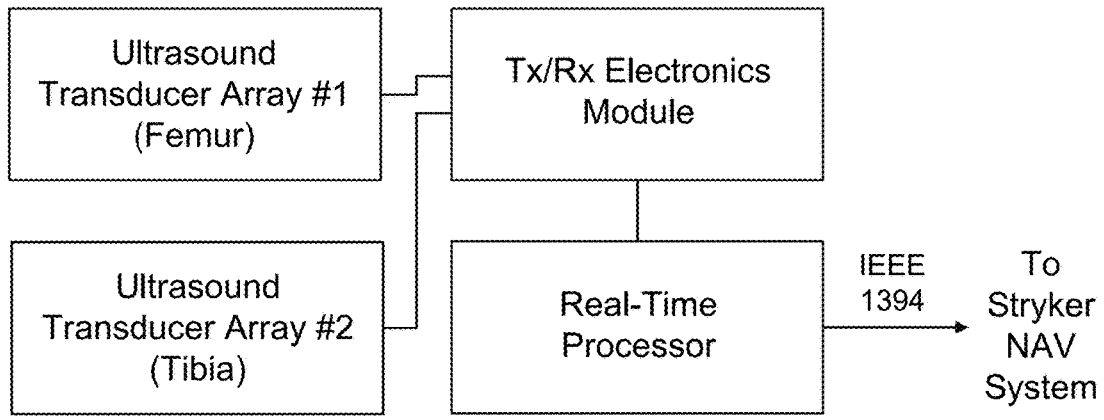
FIG. 11 shows an example hardware block diagram for the OTS.

An example hardware block diagram for the OTS is shown in FIG. 11. In some embodiments of the system, for example, the OTS hardware subsystems can include the following elements: Ultrasound Transducer Arrays #1 and #2: transmit and receive ultrasound signals reflected from the bone surfaces; Tx/Rx Electronics: include the ultrasound Transmitter circuitry and Receiver preamplifiers and A/D converters. RF signals are transferred to and from the transducer arrays. The received signals are digitized, filtered and fed into the real time processor.

Figure 12:
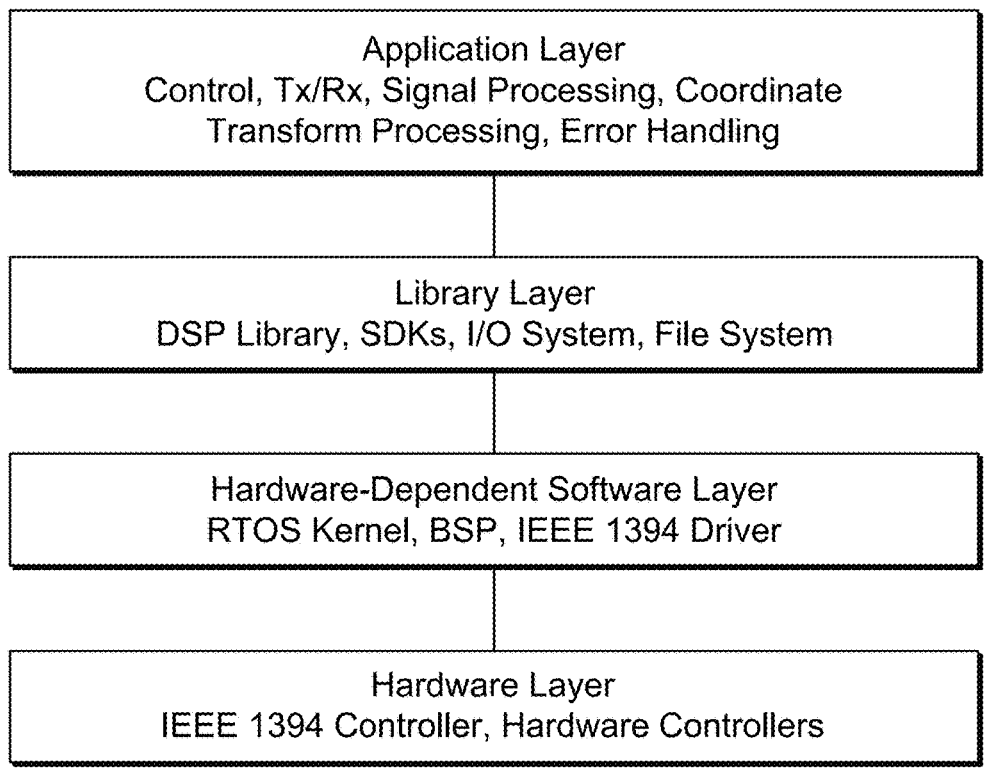
FIG. 12 shows a block diagram of an example OTS software architecture.

Real-time Data Processor: a block diagram of an example OTS software architecture is shown in FIG. 12.

System Operations: The following sections are described as an example of a system of the present technology's operational modes, parameters, and procedures. Other operational modes, parameters, and procedures may also be implemented using the system of the present technology.

Example Modes

Setup Mode: Setup mode allows a 3rd party host system operator to load 3D bone solid models, and to perform other maintenance tasks including array calibration. Setup mode can be the default mode when 3D solid models have not yet been loaded into the system.

Self-test Mode: Self-test may be programmed to automatically test major hardware functions including arrays, Tx/Rx functions, processor and I/O interfaces. Self-test returns a pass/fail indication including a detailed status message containing the results of each test performed. Status messages are transmitted to either the host system or an attached console, if used, for maintenance.

Manual Test Mode: Manual test allows an operator to perform each of tests performed in self-test individually and obtain lower-level status information for troubleshooting. Manual test can be programmed to provide measurement data that can be observed from a test dashboard that includes charts showing the returned signals from each of the transducer elements as well as 6 DoF data in a numeric or graphical format.

Run Mode: The Run mode includes two sub-modes; Acquire and Track, which are described as follows.

Acquire Mode: When commanded to the Run mode, the example acoustic OTS will begin the Acquire sub-mode, whereby it is searching for a bone cross-section match to the 3D solid model and thus not yet providing valid positional data to the STS. During this mode, messages will be continuously sent to the STS, e.g., via the IEEE 1394 interface, indicating current mode and health status of the acoustic OTS. When the acoustic OTS determines it has an acceptable match to the solid model, the Acquire Mode is completed and the OTS is registered to the 3D solid model.

Track Mode: Once the OTS software determines a sufficient match to the 3D solid model, it automatically transitions to Track mode and begins reporting 6 DoF positional data to the STS via the IEEE 1394 serial interface. The message stream includes a health status word with each frame indicating the validity of the measurement of the of the bone positions relative to the arrays. This message may include an error estimate based on correlation of the received ultrasound signals with the 3D reference models. If for any reason the OTS software senses a bone cross-section that does not adequately match the 3D solid model, it will automatically return to the Acquire mode and re-register the OTS to the 3D solid model.

Array and Mode Selection and Array Identification: The acoustic OTS can be programmed to automatically detect the type of array(s) connected to the system. Codes for the detected array type can be included in the status messages sent to the host system.

System or Subsystem Functional Operational Parameters

6 DoF Tracking: The acoustic OTS can be programmed to be used as a subsystem of a 3PSNS system to provide for 6 DoF tracking of ultrasound transducer arrays with respect to predefined coordinate systems registered to patients' bones for robotic assisted orthopedic surgery.

6DOF Tracking Sample Frequency: The acoustic OTS tracking sample frequency can be programmed to be 1 kHz or more.

6 DoF Tracking Latency: The acoustic OTS tracking latency can be programmed to be less than 3 ms.

6 DoF Tracking Latency Jitter: The acoustic OTS tracking latency jitter can be programmed to be not more than a negligible amount.

Relative Target Tracking Speed: The acoustic OTS can be programmed to track relative position of the transducer array with respect to the bone at linear speeds up to 50 mm/s.

Target Tracking Range: The acoustic OTS can be programmed to track relative position of the transducer array with respect to the bone over a range of movement +/−25 mm from the initialized starting position.

Anatomical Targets: The acoustic OTS can be programmed to be capable of tracking transducer array positions with respect to the following anatomical targets, for example, Human femur and Human tibia.

Human Patient Population: The OTS can support orthopedic surgery procedures on male and female human patients between 5th and 95th percentile calf and mid-thigh dimensions as specified in Table 1 below.

TABLE 1

Human Patient Population Characteristics

| Patient Parameter | Minimum (5th Percentile) | Maximum (95th Percentile) |
|---|---|---|
| Age, years | Over 20 | |
| Sex | male and female | |
| Calf Circumference[1], cm | 29.8 | 48.0 |
| Mid-Thigh Circumference[1], cm | 38.2 | 75.0 |
| Weight[1], lb | 102 | 275 |

The OTS system may be used on patients younger than age 20 if their limbs are within the size range specified in Table 1.

6 DoF Data Output Parameters: The OTS is able to output 6 DoF position and angle parameters, e.g., such as those defined in Table 2 below.

TABLE 2

Figure 13:
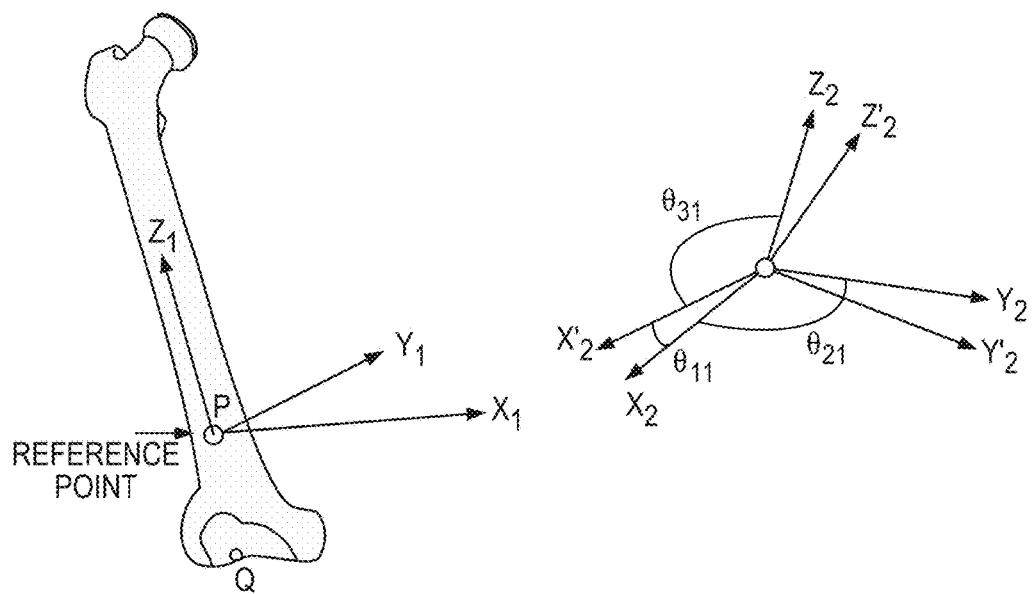
FIG. 13 shows a Femur six degrees of freedom (6 DoF) coordinate system at time T.

| 6DoF Parameters | | | |
|---|---|---|---|
| Parameter | Definition | Units | Range |
| Coordinate Translation | Origin O'$_2$ Position with respect to O$_2$ at time sample T | | |
| $\Delta X_2$ | $x_2 \cdot \Delta R_{12}$ | meters | −1 to 1 |
| $\Delta Y_2$ | $y_2 \cdot \Delta R_{12}$ | meters | −1 to 1 |
| $\Delta Z_2$ | $z_2 \cdot \Delta R_{12}$ | meters | −1 to 1 |
| Coordinate Rotation | O'$_2$ Coordinate Rotation with respect to O$_2$ at time sample T | | |
| $\cos(\theta_{11})$ | $x_2 \cdot x'_2$ | unitless | −1 to +1 |
| $\cos(\theta_{12})$ | $x_2 \cdot y'_2$ | unitless | −1 to +1 |
| $\cos(\theta_{13})$ | $x_2 \cdot z'_2$ | unitless | −1 to +1 |
| $\cos(\theta_{21})$ | $y_2 \cdot x'_2$ | unitless | −1 to +1 |
| $\cos(\theta_{22})$ | $y_2 \cdot y'_2$ | unitless | −1 to +1 |
| $\cos(\theta_{23})$ | $y_2 \cdot z'_2$ | unitless | −1 to +1 |
| $\cos(\theta_{31})$ | $z_2 \cdot x'_2$ | unitless | −1 to +1 |
| $\cos(\theta_{32})$ | $z_2 \cdot y'_2$ | unitless | −1 to +1 |
| $\cos(\theta_{33})$ | $z_2 \cdot x'_2$ | unitless | −1 to +1 |

Where $x_2$ is the unit vector in $X_2$ direction, and $x'_2$ is the unit vector in $X'_2$ direction, etc., and $\cos(\theta_{ij})$ are the elements of the direction cosine matrix describing the angular movement of the transducer array at time T as illustrated in the equation (A) below and shown in FIG. 13.

$$\begin{pmatrix} X'_2 \\ Y'_2 \\ Z'_2 \end{pmatrix} = \begin{pmatrix} \cos(\theta_{11}) & \cos(\theta_{12}) & \cos(\theta_{13}) \\ \cos(\theta_{21}) & \cos(\theta_{22}) & \cos(\theta_{23}) \\ \cos(\theta_{31}) & \cos(\theta_{32}) & \cos(\theta_{33}) \end{pmatrix} \begin{pmatrix} X_2 \\ Y_2 \\ Z_2 \end{pmatrix} \quad (A)$$

In Equation (A) above, $(X_2, Y_2, Z_2)$ is the OTS transducer coordinate reference at time t=0, when the system was initialized, and $(X'_2, Y'_2, Z'_2)$ is the new transducer angular position due to the movement of the transducer relative to the bone at a subsequent time t=T. Parameters x, y and z are measurements of the transducer's translation with respect to the bone reference frame at time t=T. FIG. 13 shows a Femur 6 DoF Coordinate System at Time T.

Operational Sequence: The acoustic OTS can be operated in the following activity sequence (e.g., knee arthroscopy, for example).

Example Pre-operative Planning: (1) Prepare 3D solid models of the patient's femur and tibia from CT scan (or other 3D tomographic) imagery; (2) Assign an orthogonal right-hand sided reference frame registered to point P on the 3D solid model (as shown in FIG. 13); (3) Verify/calibrate the OTS ultrasound arrays to appropriate 3D bone phantoms.

Example Day of Operation Planning: (1) Attach the acoustic OTS transducer arrays to patient thigh and calf at the appropriate distances from the patella; (2) Activate the acoustic OTS system electronics and monitor status including the TIB and MI output display indices via the example 3PSNS console; (3) Initialize the OTS with the transducers in their nominal positions to begin tracking via the example 3PSNS console; (4) Register the 3PSNS system to spatial fiducial points on the ultrasound arrays; (5) Register the 3PSNS system with the acoustic OTS bone tracking to appropriate reference locations on the cortical surfaces of the femur and tibia; (6) Proceed with robotic assisted orthopedic surgical procedure.

Transducer Arrays: The acoustic OTS transducer arrays can be configured so that they are suitable for use over the range of anatomical dimensions.

Femur Array(s)

Femur Array Position: The OTS femur array(s) can be configured so that they are able to map femur cortical surfaces between 6 and 12 cm from the knee joint.

Femur Array Scan Area: The OTS femur array(s) can be configured so that they are capable of scanning thigh areas between 35 and 75 cm in circumference (11.1 to 23.9 cm diameter).

Tibia Array(s)

Tibia Array Position: The OTS femur array(s) can be configured so that they are able to map tibia cortical surfaces between 6 and 12 cm from the knee joint.

Tibia Array Scan Area: The OTS femur array(s) can be configured so that they are capable of scanning calf areas between 28 and 48 cm in circumference (8.9 to 15.3 cm diameter).

Other Array(s): The disclosed technology can be used to implement arrays for other human bones, e.g., such as the hip, spine and ankle.

Output Display Standard: The OTS ultrasound system can produce an output in conformance with the Output Display Standard (NEMA UD 3-2004), as an FDA Track 3 device.

Bone Thermal Index: The OTS ultrasound system can be configured so that it provides real-time reporting of the acoustic output bone thermal index (TIB) at all times ultrasound is being transmitted. The TIB value is an estimate of the number of degrees, C, temperature rise above the ambient body temperature. TIB can be included in the data message transmitted to the 3PSNS.

Mechanical Index: The OTS ultrasound system can be configured so that it provides real-time reporting of the acoustic output Mechanical Index (MI) at all times ultrasound is being transmitted. MI can be included in the data messages transmitted to the 3PSNS.

Transducer Array Cleaning Materials: The OTS transducer arrays can be configured so that they are compatible with one or more of the following cleaning materials, for example: 75% IPA, Cidex Plus 28 Day, Cidex OPA, Cidezyme, Klenzyme or Omnicide.

Implementations of the subject matter and the functional operations described in this patent document and attached appendices can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document and attached appendices.

What is claimed is:

1. An acoustic orthopedic tracking system, comprising:
an acoustic probe device structured to include a support frame having a curved shape to interface a body part of a biological subject, and an array of transducer elements arranged on the curved support frame and operable to transmit acoustic waveforms toward a target volume of an orthopedic structure in the body part and to receive returned acoustic waveforms that return from at least part of the target volume of the orthopedic structure;
an acoustic coupling component coupled to the array of transducer elements and operable to conduct the acoustic waveforms between the at least some of the transducer elements of the array and the body part of the biological subject when in contact with the acoustic coupling component, wherein the acoustic coupling component includes a hydrogel structured to directly contact and conform to an outer surface of the body part, such that, when the acoustic coupling component is in contact with the outer surface of the body part, the acoustic coupling component provides an acoustic signal transmission path between the receiving medium and the array of transducer elements;

a signal generation and processing device in communication with the acoustic probe device and structured to include (i) a transmit and receive electronics (TRE) unit, and (ii) a data processing unit including a memory to store data and a processor coupled to the memory to process data, wherein the TRE unit includes a waveform generator in communication with the data processing unit and one or more waveform synthesizers in communication with the waveform generator to generate one or more waveforms according to waveform information provided by the data processing unit via the waveform generator, wherein the transmittable acoustic waveforms correspond to the one or more waveforms generated by the signal generation and processing device; and a position tracking device in communication with the signal generation and processing device and operable to track the position of the array of transducer elements of the acoustic probe device, wherein the data processing unit is configured to process the received returned acoustic waveforms with the tracked position of the array of transducer elements to determine (i) motion of the orthopedic structure of the body part and (ii) at least one of location coordinates or orientation of the orthopedic structure of the body part in a six degrees of freedom (6 DoF) coordinate space with respect to the tracked position of the array of transducer elements by processing position data and vector data associated with movement of the orthopedic structure with respect to the tracked position of the array of transducer elements.

2. The system of claim 1, wherein the data processing unit is configured to produce a data set that includes the determined motion and the at least one of location coordinates or orientation of the orthopedic structure of the body part, and wherein the data processing unit is in communication with a surgical system and configured to transfer the produced data set to the surgical system such that the surgical system can perform an operation or procedure on the orthopedic structure based on information including the determined motion and the at least one of location coordinates or orientation of the orthopedic structure of the body part contained in the data set.

3. The system of claim 1, wherein the position tracking device includes an optical sensor including one or more of a camera, an image sensor including a charge-coupled device (CCD), or a light emitting diode (LED).

4. The system of claim 1, wherein the hydrogel includes one or more polymerizable materials that form a network structured to entrap an aqueous fluid inside the hydrogel, wherein, when the acoustic coupling component is in contact with the outer surface of the body part, the acoustic coupling component provides an acoustic impedance matching between the receiving medium and the array of transducer elements.

5. The system of claim 1, wherein the hydrogel is structured to conform to the body part in complete contact with the surface, without packets of air or voids formed between acoustic coupling component and the body part.

6. The system of claim 1, wherein the TRE unit includes:

an array of analog to digital (A/D) converters to convert the received returned acoustic waveforms received by the array of transducer elements of the acoustic probe device from analog format to digital format as a received waveform that includes information of at least part of the target volume, one or more amplifiers in communication with the one or more waveform synthesizers to modify the waveforms provided to the acoustic probe device for transmission, and one or more pre-amplifiers in communication with the acoustic probe device and the array of A/D converters to modify the received returned acoustic waveforms provided to the A/D converters.

7. The system of claim 1, wherein the acoustic probe device includes a signal interface module connectable to the TRE unit of the signal generation and processing device, the signal interface module including a multiplexing unit in communication with the array of transducer elements to select one or more transducing elements of the array to transduce the waveforms into the corresponding acoustic waveforms, and to select one or more transducing elements of the array to receive the returned acoustic waveforms.

8. The system of claim 1, wherein the signal generation and processing device is operable to generate arbitrary waveforms, wherein the arbitrary waveforms include an arbitrary waveform describable mathematically.

9. The system of claim 8, wherein the arbitrary waveforms include one or more of rectangular pulses, triangular pulses, impulse pulses, Gaussian pulses, sinusoidal pulses, sinc pulses, Mexican hat wavelet pulses, Haar wavelet pulses, linear FM chirped pulses, hyperbolic FM chirped pulses, coded pulses, binary coded pulses, ternary coded pulses, phase coded pulses, complementary binary coded pulses, amplitude coded pulses, phase and amplitude coded pulses, frequency coded pulses, stepped sine wave pulses, shaped spectrum pulses, or combinations thereof.

10. The system of claim 8, wherein the signal generation and processing device is operable to beamform and steer the arbitrary waveforms.

11. The system of claim 1, wherein the signal generation and processing device is operable to generate a composite waveform comprising two or more of individual orthogonal coded waveforms corresponding to one or more frequency bands that are generated by the one or more waveform synthesizers according to the waveform information, wherein the individual orthogonal coded waveforms are mutually orthogonal to each other and correspond to different frequency bands, such that each of the individual orthogonal coded waveforms includes a unique frequency with a corresponding phase.

12. The system of claim 11, wherein each of the individual orthogonal coded waveforms includes a plurality of amplitudes and a plurality of phases that are individually amplitude weighted and individually phase weighted, respectively.

13. The system of claim 11, wherein the signal generation and processing device is operable to determine a frequency band, an amplitude, a time-bandwidth product parameter, and a phase parameter of each individual orthogonal coded waveform.

14. The system of claim 13, wherein the phase parameter is determined from a set of a pseudo-random numbers or from a set of deterministic numbers.

15. The system of claim 1, wherein the transmittable acoustic waveforms are transmitted sequentially one-at-a-time, simultaneously, or in a time-staggered or time-delayed pattern, and wherein the target volume includes a tissue structure of the biological subject, and the shaped section of the probe device is in contact with the body part of the biological subject.

16. The system of claim 15, wherein the body part includes an abdomen, a thorax, a neck including the throat, an arm, a leg, a knee joint, a hip joint, an ankle joint, an elbow joint, a shoulder joint, a wrist joint, a breast, a genital, or a head including the cranium.

17. The system of claim 15, wherein the biological structure includes a cancerous or noncancerous tumor, an internal legion, a connective tissue sprain, a tissue tear, or a bone.

18. The system of claim 1, wherein the data processing unit is configured to process the received returned acoustic waveforms with the tracked position of the array of transducer elements in real-time to determine (i) the motion and (ii) the at least one of location coordinates or orientation of the orthopedic structure of the body part.

19. The system of claim 1, wherein the data processing unit is configured to process the position data and the vector data associated with movement of the orthopedic structure with respect to the tracked position of the array of transducer elements by:
   determining a plurality of three-dimensional coordinate points of the orthopedic structure, wherein the coordinate points are associated with a frame of reference of the array of transducer elements; and
   translating the three-dimensional coordinate points to an external frame of reference associated with the position tracking device.

20. The system of claim 1, wherein the data processing unit is configured to direct a transmitted acoustic waveform at a focal point corresponding to a determined location coordinate of the orthopedic structure of the body part in the 6 DoF coordinate space.

* * * * *